(12) United States Patent
Hayes et al.

(10) Patent No.: US 10,196,687 B2
(45) Date of Patent: Feb. 5, 2019

(54) MOLECULAR DIAGNOSIS AND TYPING OF LUNG CANCER VARIANTS

(71) Applicants: The University of North Carolina at Chapel Hill, Chapel Hill, NC (US); University of Utah Research Foundation, Salt Lake City, UT (US)

(72) Inventors: David N. Hayes, Chapel Hill, NC (US); Charles M. Perou, Chapel Hill, NC (US); Philip Bernard, Salt Lake City, UT (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/358,622

(22) Filed: Nov. 22, 2016

(65) Prior Publication Data

US 2017/0298414 A1 Oct. 19, 2017

Related U.S. Application Data

(63) Continuation of application No. 14/334,855, filed on Jul. 18, 2014, now abandoned, which is a continuation of application No. 12/602,649, filed as application No. PCT/US2008/065489 on Jun. 2, 2008, now Pat. No. 8,822,153.

(60) Provisional application No. 60/941,520, filed on Jun. 1, 2007.

(51) Int. Cl.
| | |
|---|---|
| *C12Q 1/68* | (2018.01) |
| *C12Q 1/686* | (2018.01) |
| *C12Q 1/6886* | (2018.01) |
| *G01N 33/574* | (2006.01) |

(52) U.S. Cl.
CPC .......... *C12Q 1/686* (2013.01); *C12Q 1/6886* (2013.01); *G01N 33/57423* (2013.01); *C12Q 2600/106* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2005/0119196 A1* | 6/2005 | Noguchi | ............. | A61K 31/337 514/34 |
| 2006/0024692 A1* | 2/2006 | Nakamura | ........... | C12Q 1/6886 435/6.12 |
| 2006/0194229 A1* | 8/2006 | North | ................. | C12N 15/1135 435/6.14 |
| 2008/0045471 A1* | 2/2008 | North | ................. | C12N 15/1135 514/44 R |
| 2009/0061454 A1* | 3/2009 | Brody | ................. | C12Q 1/6886 435/6.14 |
| 2010/0009357 A1* | 1/2010 | Nevins | ................ | C12Q 1/6886 435/6.12 |

FOREIGN PATENT DOCUMENTS

| | | |
|---|---|---|
| EP | 1743947 A2 | 9/2003 |
| WO | 0194629 A2 | 12/2001 |

OTHER PUBLICATIONS

Graff L, Castrop F, Bauer M, Höfler H, Gratzl M. Expression of vesicular monoamine transporters, synaptosomal-associated protein 25 and syntaxin1: a signature of human small cell lung carcinoma. Cancer Res. Mar. 1, 2001;61(5):2138-44.*
Raponi M, Zhang Y, Yu J, Chen G, Lee G, Taylor JM, Macdonald J, Thomas D, Moskaluk C, Wang Y, Beer DG. Gene expression signatures for predicting prognosis of squamous cell and adenocarcinomas of the lung. Cancer Res. Aug. 1, 2006;66(15):7466-72.*
Arneson N, Moreno J, Iakovlev V, Ghazani A, Warren K, McCready D, Jurisica I, Done SJ. Comparison of whole genome amplification methods for analysis of DNA extracted from microdissected early breast lesions in formalin-fixed paraffin-embedded tissue. ISRN Oncol. 2012; 2012:710692. Epub Mar. 14, 2012. (Year: 2012).*
Hawthorn L, Stein L, Panzarella J, Loewen GM, Baumann H. Characterization of cell-type specific profiles in tissues and isolated cells from squamous cell carcinomas of the lung. Lung Cancer. Aug. 2006; 53(2):129-42. (Year: 2006).*
Hosono S, Faruqi AF, Dean FB, Du Y, Sun Z, Wu X, Du J, Kingsmore SF, Egholm M, Lasken RS. Unbiased whole-genome amplification directly from clinical samples. Genome Res. May 2003; 13(5):954-64. Epub Apr. 14, 2003. (Year: 2003).*
Vandesompele J, De Preter K, Pattyn F, Poppe B, Van Roy N, De Paepe A, Speleman F. Accurate normalization of real-time quantitative RT-PCR data by geometric averaging of multiple internal control genes. Genome Biol. Jun. 18, 2002; 3(7): pp. 1-12. (Year: 2002).*
Au, NHC et al., "Evaluation of immunohistochemical markers in non-small cell lung cancer by unsupervised hierarchical clustering analysis: a tissue microarray study of 284 cases and 18 markers" J Pathol. 2004. 204(1):pp. 101-109.
Beer, D. G. et al., "Gene-expression profiles predict survival of patients with lung adenocarcinoma" Nat Med. Aug. 2002; 8(8): pp. 816-824. Epub Jul. 15, 2002.

(Continued)

*Primary Examiner* — Aaron A Priest
*Assistant Examiner* — Olayinka A Oyeyemi
(74) *Attorney, Agent, or Firm* — Olive Law Group, PLLC; Nathan P. Letts

(57) ABSTRACT

Compositions and methods useful in determining the major morphological types of lung cancer are provided. The methods include detecting expression of at least one gene or biomarker in a sample at the protein or nucleic level. The expression of the gene or biomarker can be indicative of the lung tumor subtype as well as prognostic and predictive for therapeutic response. The compositions and methods provided herein are suited for analysis of gene or biomarker expression at the protein or nucleic acid level in paraffin-embedded tissues.

12 Claims, 14 Drawing Sheets
Specification includes a Sequence Listing.

(56) References Cited

OTHER PUBLICATIONS

Bhattacharjee A. et al., "Classification of human lung carcinomas by mRNA expression profiling reveals distinct adenocarcinoma subclasses" PNAS Nov. 20, 2001;98(24): pp. 13790-13795. Epub Nov. 13, 2001.

Bibikova, M. et al., "Quantitative Gene Expression Profiling in Formalin-Fixed, Paraffin-Embedded Tissues Using Universal Bead Arrays" American Journal of Pathology, Nov. 2004, pp. 1799-1807, vol. 165, No. 5.

Bloom G. et al., "Multi-platform, multi-site, microarray-based human tumor classification" Am J Pathol. Jan. 2004;164(1): pp. 9-16.

Borczuk et al., "Molecular signatures in biopsy specimens of lung cancer" Am J Respir Crit Care Med. Jul. 15, 2004;170(2): pp. 167-174. Epub Apr. 15, 2004.

Botling J. et al., "Biomarker discovery in non-small cell lung cancer: integrating gene expression profiling, meta-analysis, and tissue microarray validation" Clin Cancer Res. Jan. 1, 2003;19(19): pp. 194-204.

Enard W. et al., "Intra-and interspecific variation in primate gene expression patterns" Science. Apr. 12, 2002;296(5566): pp. 340-343.

Garber M. E. et al., "Diversity of gene expression in adenocarcinoma of the lung" PNAS 2001. 98(24): pp. 13784-13789.

Graff L. et al,. "Expression of vesicular monoamine transporters, synaptosomal-associated protein 25 and syntazin1: a signature of human small cell lung carcinoma" Cancer Res, 2001. 61(5): pp. 2138-2144.

Hayes, D. N. et al., "Gene expression profiling reveals Reproducible Human Lung Adenocarcinoma Subtypes in Multiple independent Patient Cohorts," Journal of Clinical Oncology, Nov. 1, 2008, pp. 5079-5090, vol. 24, No. 31.

Inamura K. et al., "Two subclasses of lung squamous cell carcinoma with different gene expression profiles and prognosis identified by hierarchical clustering and non-negative matrix factorization" Oncogene. 2005. 24(47): pp. 7105-7113.

Kerr K. M., "Classification of lung cancer: proposals for change?" Arch Pathol Lab Med. Oct. 2012;136(10): pp. 1190-1193.

Parmigiani G. et al., "A cross-study comparison of gene expression studies for the molecular classification of lung cancer" Clin Cancer Res. 2004. 10(9): pp. 2922-2927.

Porebska, I. et al., "Apoptotic markers p53, Bcl-2 and Bax in Primary Lung Cancer," in Vivo, Sep. 2006, pp. 599-604, vol. 20. No. 5.

Ramaswamy S. et al., "Multiclass cancer diagnosis using tumor gene expression signatures" PNAS; 2001; 98(26): pp. 15149-15154.

Ranganathan P. et al,. "Expression profiling of genes regulated by TGF-beta: differential regulation in normal and tumor cells" BMC Genomics. Apr. 11, 2007; 8:98.

Raponi et al,. Cancer Res 2006. 66(15):7466-72. Supplemental Supporting Information.

Smirnov D. A. et al., "Global Gene Expression Profiling of Circulating Endothelial Cells in Patients with Metastatic Carcinomas," Cancer Research, Mar. 15, 2006. pp. 2918-2922, vol. 66, No. 6.

Stearman RS. et al,. "Analysis of orthologous gene expression between human pulmonary adenocarcinoma and a carcinogen-induced murine model" Am J Pathol. Dec. 2005; 167(6): pp. 1763-1775.

Takeuchi T. et al,. "Expression profile-defined classification of lung adenocarcinoma shows close relationship with underlying major genetic changes and clinicopathologic behaviors" J Clin Oncol. Apr. 10; 24(11): pp. 1679-1688. Epub Mar. 20, 2006.

Tomida S. et al., "Gene expression-based, individualized outcome prediction for surgically treated lung cancer patients" Oncogene. 2004. 23(31): pp. 5360-5370.

Nhitehead A. et al., "Variation in tissue-specific gene expression among natural populations" Genome Biol. 2005;6(2):R13. Epub 2005 26.

Wu, M., et al., "Cytology Applications of p63 and TTF-1 Immunostaining in Differential Diagnosis of Lung Cancers," Diagnostic Cytopathology, Oct. 2005, pp. 223-227 vol. 33 No. 4.

Zhu C. et al., "Understanding prognostic gene expression signature in lung cancer" Clin Lung Cancer. Sep. 10, 2009 (5): pp. 331-340.

* cited by examiner

|  | AD | CARCINOID | NORMAL | SCC | SCLC |
|---|---|---|---|---|---|
| AD | 79 | 0 | 1 | 4 | 0 |
| CARCINOID | 0 | 16 | 1 | 0 | 0 |
| NORMAL | 0 | 0 | 8 | 0 | 0 |
| SCC | 4 | 0 | 1 | 41 | 0 |
| SCLC | 0 | 0 | 0 | 0 | 2 |

True Morphology (rows) / Predicted Morphology (columns)

FIGURE 11

SEQUENCE LISTING

<160> NUMBER OF SEQ ID NOS: 114

<210> SEQ ID NO 1
<211> LENGTH: 22
<212> TYPE: DNA
<213> ORGANISM: Artificial Sequence
<220> FEATURE:
<223> OTHER INFORMATION: Synthetic sequence

<400> SEQUENCE: 1

-continued

```
aagagagatt ggatttggaa cc                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence

<400> SEQUENCE: 2
ccagaagccc aagaagattg ta                                              22

<210> SEQ ID NO 3
<211> LENGTH: 19
<212> TYPE: DNA
<213> ORGANISM: Artificial Sequence
<220> FEATURE:
<223> OTHER INFORMATION: Synthetic sequence

<400> SEQUENCE: 3
aatcctggtg tcaaggaag                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic sequence

<400> SEQUENCE: 4
ggaccgattt taccgatcc                                                  19

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
acagtccaga tagtcgtatg t                                               21

<210> SEQ ID NO 6
<211> LENGTH: 17
<212> TYPE: DNA
<213> ORGANISM: Artificial Sequence
<220> FEATURE:
<223> OTHER INFORMATION: Synthetic sequence

<400> SEQUENCE: 6
gtctccgcca tccctat                                                    17

<210> SEQ ID NO 7
<211> LENGTH: 19
<212> TYPE: DNA
<213> ORGANISM: Artificial Sequence
<220> FEATURE:
<223> OTHER INFORMATION: Synthetic sequence

<400> SEQUENCE: 7
actggtgtaa caggaacat                                                  19

<210> SEQ ID NO 8
<211> LENGTH: 17
<212> TYPE: DNA
```

```
<213> ORGANISM: Artificial Sequence
<220> FEATURE:
<223> OTHER INFORMATION: Synthetic sequence

<400> SEQUENCE: 8
tttggaagga ctgcgct                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic sequence

<400> SEQUENCE: 9
cacgtcatct cccgttc                                                    17

<210> SEQ ID NO 10
<211> LENGTH: 18
<212> TYPE: DNA
<213> ORGANISM: Artificial Sequence
<220> FEATURE:
<223> OTHER INFORMATION: Synthetic sequence

<400> SEQUENCE: 10
attgaacttc ccacacga                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic sequence

<400> SEQUENCE: 11
ggaacagact gtcaccat                                                   18

<210> SEQ ID NO 12
<211> LENGTH: 17
<212> TYPE: DNA
<213> ORGANISM: Artificial Sequence
<220> FEATURE:
<223> OTHER INFORMATION: Synthetic sequence

<400> SEQUENCE: 12
tcagagtgtg gtcaggc                                                    17

<210> SEQ ID NO 13
<211> LENGTH: 17
<212> TYPE: DNA
<213> ORGANISM: Artificial Sequence
<220> FEATURE:
<223> OTHER INFORMATION: Synthetic sequence

<400> SEQUENCE: 13
gggacagctt caacact                                                    17

<210> SEQ ID NO 14
<211> LENGTH: 18
<212> TYPE: DNA
<213> ORGANISM: Artificial Sequence
<220> FEATURE:
<223> OTHER INFORMATION: Synthetic sequence

<400> SEQUENCE: 14
cctgtgaaca gccctatg                                                   18
```

<210> SEQ ID NO 15
<211> LENGTH: 17
<212> TYPE: DNA
<213> ORGANISM: Artificial Sequence
<220> FEATURE:
<223> OTHER INFORMATION: Synthetic sequence

<400> SEQUENCE: 15
ttctgggcac ggtgaag                                                  17

<210> SEQ ID NO 16
<211> LENGTH: 21
<212> TYPE: DNA
<213> ORGANISM: Artificial Sequence
<220> FEATURE:
<223> OTHER INFORMATION: Synthetic sequence

<400> SEQUENCE: 16
ggccaaacta gagcacgaat a                                             21

<210> SEQ ID NO 17
<211> LENGTH: 19
<212> TYPE: DNA
<213> ORGANISM: Artificial Sequence
<220> FEATURE:
<223> OTHER INFORMATION: Synthetic sequence

<400> SEQUENCE: 17
tcagcaagaa ggagatgcc                                                19

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence

<400> SEQUENCE: 18
gtgctccctc tccattaagt a                                             21

<210> SEQ ID NO 19
<211> LENGTH: 20
<212> TYPE: DNA
<213> ORGANISM: Artificial Sequence
<220> FEATURE:
<223> OTHER INFORMATION: Synthetic sequence

<400> SEQUENCE: 19
caagttcagg agaactcgac                                               20

<210> SEQ ID NO 20
<211> LENGTH: 19
<212> TYPE: DNA
<213> ORGANISM: Artificial Sequence
<220> FEATURE:
<223> OTHER INFORMATION: Synthetic sequence

<400> SEQUENCE: 20
ggctgtggtt atgcgatag                                                19

<210> SEQ ID NO 21
<211> LENGTH: 18
<212> TYPE: DNA
<213> ORGANISM: Artificial Sequence
<220> FEATURE:

<223> OTHER INFORMATION: Synthetic sequence

<400> SEQUENCE: 21
acccgaggaa caacctta                                          18

<210> SEQ ID NO 22
<211> LENGTH: 18
<212> TYPE: DNA
<213> ORGANISM: Artificial Sequence
<220> FEATURE:
<223> OTHER INFORMATION: Synthetic sequence

<400> SEQUENCE: 22
ccctctccat tccctaca                                          18

<210> SEQ ID NO 23
<211> LENGTH: 17
<212> TYPE: DNA
<213> ORGANISM: Artificial Sequence
<220> FEATURE:
<223> OTHER INFORMATION: Synthetic sequence

<400> SEQUENCE: 23
cagagcgcca ggcatta                                           17

<210> SEQ ID NO 24
<211> LENGTH: 18
<212> TYPE: DNA
<213> ORGANISM: Artificial Sequence
<220> FEATURE:
<223> OTHER INFORMATION: Synthetic sequence

<400> SEQUENCE: 24
ccactggctg aggtgtta                                          18

<210> SEQ ID NO 25
<211> LENGTH: 17
<212> TYPE: DNA
<213> ORGANISM: Artificial Sequence
<220> FEATURE:
<223> OTHER INFORMATION: Synthetic sequence

<400> SEQUENCE: 25
tgggcgagtc tacgatg                                           17

<210> SEQ ID NO 26
<211> LENGTH: 18
<212> TYPE: DNA
<213> ORGANISM: Artificial Sequence
<220> FEATURE:
<223> OTHER INFORMATION: Synthetic sequence

<400> SEQUENCE: 26
ctttctgccc tggagatg                                          18

<210> SEQ ID NO 27
<211> LENGTH: 19
<212> TYPE: DNA
<213> ORGANISM: Artificial Sequence
<220> FEATURE:
<223> OTHER INFORMATION: Synthetic sequence

<400> SEQUENCE: 27
gcgccatttg ctagagata                                         19

```
<210> SEQ ID NO 28
<211> LENGTH: 19
<212> TYPE: DNA
<213> ORGANISM: Artificial Sequence
<220> FEATURE:
<223> OTHER INFORMATION: Synthetic sequence

<400> SEQUENCE: 28
agagaagatg ggcagaaag                                                  19

<210> SEQ ID NO 29
<211> LENGTH: 17
<212> TYPE: DNA
<213> ORGANISM: Artificial Sequence
<220> FEATURE:
<223> OTHER INFORMATION: Synthetic sequence

<400> SEQUENCE: 29
gcccagatca tccgtca                                                    17

<210> SEQ ID NO 30
<211> LENGTH: 17
<212> TYPE: DNA
<213> ORGANISM: Artificial Sequence
<220> FEATURE:
<223> OTHER INFORMATION: Synthetic sequence

<400> SEQUENCE: 30
accacaagga cttcgac                                                    17

<210> SEQ ID NO 31
<211> LENGTH: 17
<212> TYPE: DNA
<213> ORGANISM: Artificial Sequence
<220> FEATURE:
<223> OTHER INFORMATION: Synthetic sequence

<400> SEQUENCE: 31
gctccgctgc tatcttt                                                    17

<210> SEQ ID NO 32
<211> LENGTH: 17
<212> TYPE: DNA
<213> ORGANISM: Artificial Sequence
<220> FEATURE:
<223> OTHER INFORMATION: Synthetic sequence

<400> SEQUENCE: 32
agcggccagg tggatta                                                    17

<210> SEQ ID NO 33
<211> LENGTH: 18
<212> TYPE: DNA
<213> ORGANISM: Artificial Sequence
<220> FEATURE:
<223> OTHER INFORMATION: Synthetic sequence

<400> SEQUENCE: 33
atgggctttg ggagcata                                                   18

<210> SEQ ID NO 34
<211> LENGTH: 18
<212> TYPE: DNA
<213> ORGANISM: Artificial Sequence
<220> FEATURE:
<223> OTHER INFORMATION: Synthetic sequence
```

<400> SEQUENCE: 34
gacctggatg ccaagcta                                              18

<210> SEQ ID NO 35
<211> LENGTH: 17
<212> TYPE: DNA
<213> ORGANISM: Artificial Sequence
<220> FEATURE:
<223> OTHER INFORMATION: Synthetic sequence

<400> SEQUENCE: 35
ccggctcttg gaagttg                                               17

<210> SEQ ID NO 36
<211> LENGTH: 20
<212> TYPE: DNA
<213> ORGANISM: Artificial Sequence
<220> FEATURE:
<223> OTHER INFORMATION: Synthetic sequence

<400> SEQUENCE: 36
acgcggatcg agtttgataa                                            20

<210> SEQ ID NO 37
<211> LENGTH: 17
<212> TYPE: DNA
<213> ORGANISM: Artificial Sequence
<220> FEATURE:
<223> OTHER INFORMATION: Synthetic sequence

<400> SEQUENCE: 37
cgcaagtccc agaagat                                               17

<210> SEQ ID NO 38
<211> LENGTH: 17
<212> TYPE: DNA
<213> ORGANISM: Artificial Sequence
<220> FEATURE:
<223> OTHER INFORMATION: Synthetic sequence

<400> SEQUENCE: 38
cgcggatacg atgtcac                                               17

<210> SEQ ID NO 39
<211> LENGTH: 17
<212> TYPE: DNA
<213> ORGANISM: Artificial Sequence
<220> FEATURE:
<223> OTHER INFORMATION: Synthetic sequence

<400> SEQUENCE: 39
gaactcggcc tatcgct                                               17

<210> SEQ ID NO 40
<211> LENGTH: 20
<212> TYPE: DNA
<213> ORGANISM: Artificial Sequence
<220> FEATURE:
<223> OTHER INFORMATION: Synthetic sequence

<400> SEQUENCE: 40
tctgacctca tcatcggcaa                                            20

<210> SEQ ID NO 41
<211> LENGTH: 20

```
<212> TYPE: DNA
<213> ORGANISM: Artificial Sequence
<220> FEATURE:
<223> OTHER INFORMATION: Synthetic sequence

<400> SEQUENCE: 41
gaggtgaagc aaactacgga                                               20

<210> SEQ ID NO 42
<211> LENGTH: 17
<212> TYPE: DNA
<213> ORGANISM: Artificial Sequence
<220> FEATURE:
<223> OTHER INFORMATION: Synthetic sequence

<400> SEQUENCE: 42
actctccaca aagctcg                                                  17

<210> SEQ ID NO 43
<211> LENGTH: 22
<212> TYPE: DNA
<213> ORGANISM: Artificial Sequence
<220> FEATURE:
<223> OTHER INFORMATION: Synthetic sequence

<400> SEQUENCE: 43
ggatttcagc taccagttac tt                                            22

<210> SEQ ID NO 44
<211> LENGTH: 17
<212> TYPE: DNA
<213> ORGANISM: Artificial Sequence
<220> FEATURE:
<223> OTHER INFORMATION: Synthetic sequence

<400> SEQUENCE: 44
ttcgtcctgg tggatcg                                                  17

<210> SEQ ID NO 45
<211> LENGTH: 22
<212> TYPE: DNA
<213> ORGANISM: Artificial Sequence
<220> FEATURE:
<223> OTHER INFORMATION: Synthetic sequence

<400> SEQUENCE: 45
agtgattgat gtgtttgcta tg                                            22

<210> SEQ ID NO 46
<211> LENGTH: 20
<212> TYPE: DNA
<213> ORGANISM: Artificial Sequence
<220> FEATURE:
<223> OTHER INFORMATION: Synthetic sequence

<400> SEQUENCE: 46
caaagccaag ccactcactc                                               20

<210> SEQ ID NO 47
<211> LENGTH: 17
<212> TYPE: DNA
<213> ORGANISM: Artificial Sequence
<220> FEATURE:
<223> OTHER INFORMATION: Synthetic sequence

<400> SEQUENCE: 47
```
ctcggcagtc ctgtttc    17

<210> SEQ ID NO 48
<211> LENGTH: 18
<212> TYPE: DNA
<213> ORGANISM: Artificial Sequence
<220> FEATURE:
<223> OTHER INFORMATION: Synthetic sequence

<400> SEQUENCE: 48
acacctggta cgtcagaa    18

<210> SEQ ID NO 49
<211> LENGTH: 20
<212> TYPE: DNA
<213> ORGANISM: Artificial Sequence
<220> FEATURE:
<223> OTHER INFORMATION: Synthetic sequence

<400> SEQUENCE: 49
atgcccaaga gaatcgtaaa    20

<210> SEQ ID NO 50
<211> LENGTH: 19
<212> TYPE: DNA
<213> ORGANISM: Artificial Sequence
<220> FEATURE:
<223> OTHER INFORMATION: Synthetic sequence

<400> SEQUENCE: 50
atgagtccaa agcacacga    19

<210> SEQ ID NO 51
<211> LENGTH: 22
<212> TYPE: DNA
<213> ORGANISM: Artificial Sequence
<220> FEATURE:
<223> OTHER INFORMATION: Synthetic sequence

<400> SEQUENCE: 51
tgagattgag gatgaagctg ag    22

<210> SEQ ID NO 52
<211> LENGTH: 17
<212> TYPE: DNA
<213> ORGANISM: Artificial Sequence
<220> FEATURE:
<223> OTHER INFORMATION: Synthetic sequence

<400> SEQUENCE: 52
ccgactcaac gtgagac    17

<210> SEQ ID NO 53
<211> LENGTH: 17
<212> TYPE: DNA
<213> ORGANISM: Artificial Sequence
<220> FEATURE:
<223> OTHER INFORMATION: Synthetic sequence

<400> SEQUENCE: 53
gtgccctctc cttttcg    17

<210> SEQ ID NO 54
<211> LENGTH: 18
<212> TYPE: DNA
<213> ORGANISM: Artificial Sequence

```
<220> FEATURE:
<223> OTHER INFORMATION: Synthetic sequence

<400> SEQUENCE: 54
cgttcttttt cgcaacgg                                                   18

<210> SEQ ID NO 55
<211> LENGTH: 17
<212> TYPE: DNA
<213> ORGANISM: Artificial Sequence
<220> FEATURE:
<223> OTHER INFORMATION: Synthetic sequence

<400> SEQUENCE: 55
ggtgtgccac tgaagat                                                    17

<210> SEQ ID NO 56
<211> LENGTH: 17
<212> TYPE: DNA
<213> ORGANISM: Artificial Sequence
<220> FEATURE:
<223> OTHER INFORMATION: Synthetic sequence

<400> SEQUENCE: 56
gtgtcgtggt ggtcatt                                                    17

<210> SEQ ID NO 57
<211> LENGTH: 17
<212> TYPE: DNA
<213> ORGANISM: Artificial Sequence
<220> FEATURE:
<223> OTHER INFORMATION: Synthetic sequence

<400> SEQUENCE: 57
gcatgaagac agtggct                                                    17

<210> SEQ ID NO 58
<211> LENGTH: 17
<212> TYPE: DNA
<213> ORGANISM: Artificial Sequence
<220> FEATURE:
<223> OTHER INFORMATION: Synthetic sequence

<400> SEQUENCE: 58
ttcttgcgac tcacgct                                                    17

<210> SEQ ID NO 59
<211> LENGTH: 24
<212> TYPE: DNA
<213> ORGANISM: Artificial Sequence
<220> FEATURE:
<223> OTHER INFORMATION: Synthetic sequence

<400> SEQUENCE: 59
gctcctcaaa catctttgtg ttca                                            24

<210> SEQ ID NO 60
<211> LENGTH: 20
<212> TYPE: DNA
<213> ORGANISM: Artificial Sequence
<220> FEATURE:
<223> OTHER INFORMATION: Synthetic sequence

<400> SEQUENCE: 60
gaccactgtg ggtcattatt                                                 20
```

```
<210> SEQ ID NO 61
<211> LENGTH: 17
<212> TYPE: DNA
<213> ORGANISM: Artificial Sequence
<220> FEATURE:
<223> OTHER INFORMATION: Synthetic sequence

<400> SEQUENCE: 61
gaaatctctg gccgctc                                                    17

<210> SEQ ID NO 62
<211> LENGTH: 21
<212> TYPE: DNA
<213> ORGANISM: Artificial Sequence
<220> FEATURE:
<223> OTHER INFORMATION: Synthetic sequence

<400> SEQUENCE: 62
actgggcatc ataagaaatc c                                               21

<210> SEQ ID NO 63
<211> LENGTH: 19
<212> TYPE: DNA
<213> ORGANISM: Artificial Sequence
<220> FEATURE:
<223> OTHER INFORMATION: Synthetic sequence

<400> SEQUENCE: 63
actgaacaga agacttcgt                                                  19

<210> SEQ ID NO 64
<211> LENGTH: 20
<212> TYPE: DNA
<213> ORGANISM: Artificial Sequence
<220> FEATURE:
<223> OTHER INFORMATION: Synthetic sequence

<400> SEQUENCE: 64
aacctccaag tggaaattct                                                 20

<210> SEQ ID NO 65
<211> LENGTH: 22
<212> TYPE: DNA
<213> ORGANISM: Artificial Sequence
<220> FEATURE:
<223> OTHER INFORMATION: Synthetic sequence

<400> SEQUENCE: 65
tcggtctttc aaatcgggat ta                                              22

<210> SEQ ID NO 66
<211> LENGTH: 18
<212> TYPE: DNA
<213> ORGANISM: Artificial Sequence
<220> FEATURE:
<223> OTHER INFORMATION: Synthetic sequence

<400> SEQUENCE: 66
ctgctgtcac aggacaat                                                   18

<210> SEQ ID NO 67
<211> LENGTH: 19
<212> TYPE: DNA
<213> ORGANISM: Artificial Sequence
<220> FEATURE:
<223> OTHER INFORMATION: Synthetic sequence
```

<400> SEQUENCE: 67
aaggtaaagc cagactcca                                            19

<210> SEQ ID NO 68
<211> LENGTH: 17
<212> TYPE: DNA
<213> ORGANISM: Artificial Sequence
<220> FEATURE:
<223> OTHER INFORMATION: Synthetic sequence

<400> SEQUENCE: 68
gggagcgtag ggttaag                                              17

<210> SEQ ID NO 69
<211> LENGTH: 22
<212> TYPE: DNA
<213> ORGANISM: Artificial Sequence
<220> FEATURE:
<223> OTHER INFORMATION: Synthetic sequence

<400> SEQUENCE: 69
cagtgtattc tgcacaatca ac                                        22

<210> SEQ ID NO 70
<211> LENGTH: 21
<212> TYPE: DNA
<213> ORGANISM: Artificial Sequence
<220> FEATURE:
<223> OTHER INFORMATION: Synthetic sequence

<400> SEQUENCE: 70
gttccaggat gttggacttt c                                         21

<210> SEQ ID NO 71
<211> LENGTH: 18
<212> TYPE: DNA
<213> ORGANISM: Artificial Sequence
<220> FEATURE:
<223> OTHER INFORMATION: Synthetic sequence

<400> SEQUENCE: 71
ggaaagtgtg tcggagat                                             18

<210> SEQ ID NO 72
<211> LENGTH: 18
<212> TYPE: DNA
<213> ORGANISM: Artificial Sequence
<220> FEATURE:
<223> OTHER INFORMATION: Synthetic sequence

<400> SEQUENCE: 72
aggcaacatc attccctc                                             18

<210> SEQ ID NO 73
<211> LENGTH: 22
<212> TYPE: DNA
<213> ORGANISM: Artificial Sequence
<220> FEATURE:
<223> OTHER INFORMATION: Synthetic sequence

<400> SEQUENCE: 73
gtcaacaccc atcttcttga aa                                        22

<210> SEQ ID NO 74

```
<211> LENGTH: 18
<212> TYPE: DNA
<213> ORGANISM: Artificial Sequence
<220> FEATURE:
<223> OTHER INFORMATION: Synthetic sequence

<400> SEQUENCE: 74
cgtagtggaa gacggaaa                                                  18

<210> SEQ ID NO 75
<211> LENGTH: 23
<212> TYPE: DNA
<213> ORGANISM: Artificial Sequence
<220> FEATURE:
<223> OTHER INFORMATION: Synthetic sequence

<400> SEQUENCE: 75
ctggtgtaga attaggagac gta                                            23

<210> SEQ ID NO 76
<211> LENGTH: 17
<212> TYPE: DNA
<213> ORGANISM: Artificial Sequence
<220> FEATURE:
<223> OTHER INFORMATION: Synthetic sequence

<400> SEQUENCE: 76
ggcatcaaga gagaggc                                                   17

<210> SEQ ID NO 77
<211> LENGTH: 24
<212> TYPE: DNA
<213> ORGANISM: Artificial Sequence
<220> FEATURE:
<223> OTHER INFORMATION: Synthetic sequence

<400> SEQUENCE: 77
gataaagagt tacaagctcc tctg                                           24

<210> SEQ ID NO 78
<211> LENGTH: 17
<212> TYPE: DNA
<213> ORGANISM: Artificial Sequence
<220> FEATURE:
<223> OTHER INFORMATION: Synthetic sequence

<400> SEQUENCE: 78
tctaggcctt gacggat                                                   17

<210> SEQ ID NO 79
<211> LENGTH: 19
<212> TYPE: DNA
<213> ORGANISM: Artificial Sequence
<220> FEATURE:
<223> OTHER INFORMATION: Synthetic sequence

<400> SEQUENCE: 79
tttgggcaaa cctcggtaa                                                 19

<210> SEQ ID NO 80
<211> LENGTH: 17
<212> TYPE: DNA
<213> ORGANISM: Artificial Sequence
<220> FEATURE:
<223> OTHER INFORMATION: Synthetic sequence

<400> SEQUENCE: 80
```

```
gcacagcaaa tgccact                                                    17

<210> SEQ ID NO 81
<211> LENGTH: 23
<212> TYPE: DNA
<213> ORGANISM: Artificial Sequence
<220> FEATURE:
<223> OTHER INFORMATION: Synthetic sequence

<400> SEQUENCE: 81
cttgtctttc cctactgtct tac                                             23

<210> SEQ ID NO 82
<211> LENGTH: 18
<212> TYPE: DNA
<213> ORGANISM: Artificial Sequence
<220> FEATURE:
<223> OTHER INFORMATION: Synthetic sequence

<400> SEQUENCE: 82
cttgttccag cagaacct                                                   18

<210> SEQ ID NO 83
<211> LENGTH: 18
<212> TYPE: DNA
<213> ORGANISM: Artificial Sequence
<220> FEATURE:
<223> OTHER INFORMATION: Synthetic sequence

<400> SEQUENCE: 83
cagtcctctg caccgtta                                                   18

<210> SEQ ID NO 84
<211> LENGTH: 18
<212> TYPE: DNA
<213> ORGANISM: Artificial Sequence
<220> FEATURE:
<223> OTHER INFORMATION: Synthetic sequence

<400> SEQUENCE: 84
catccagatc cctcacat                                                   18

<210> SEQ ID NO 85
<211> LENGTH: 19
<212> TYPE: DNA
<213> ORGANISM: Artificial Sequence
<220> FEATURE:
<223> OTHER INFORMATION: Synthetic sequence

<400> SEQUENCE: 85
ccaagacaca gccagtaat                                                  19

<210> SEQ ID NO 86
<211> LENGTH: 18
<212> TYPE: DNA
<213> ORGANISM: Artificial Sequence
<220> FEATURE:
<223> OTHER INFORMATION: Synthetic sequence

<400> SEQUENCE: 86
tttccagccc tcgtagtc                                                   18

<210> SEQ ID NO 87
<211> LENGTH: 17
<212> TYPE: DNA
```

```
<213> ORGANISM: Artificial Sequence
<220> FEATURE:
<223> OTHER INFORMATION: Synthetic sequence

<400> SEQUENCE: 87
gggacacagg gaagaac                                                 17

<210> SEQ ID NO 88
<211> LENGTH: 17
<212> TYPE: DNA
<213> ORGANISM: Artificial Sequence
<220> FEATURE:
<223> OTHER INFORMATION: Synthetic sequence

<400> SEQUENCE: 88
gtctgccact ctgcaac                                                 17

<210> SEQ ID NO 89
<211> LENGTH: 17
<212> TYPE: DNA
<213> ORGANISM: Artificial Sequence
<220> FEATURE:
<223> OTHER INFORMATION: Synthetic sequence

<400> SEQUENCE: 89
gtcggctgac gctttga                                                 17

<210> SEQ ID NO 90
<211> LENGTH: 23
<212> TYPE: DNA
<213> ORGANISM: Artificial Sequence
<220> FEATURE:
<223> OTHER INFORMATION: Synthetic sequence

<400> SEQUENCE: 90
gaacaagtca gtctagggaa tac                                          23

<210> SEQ ID NO 91
<211> LENGTH: 21
<212> TYPE: DNA
<213> ORGANISM: Artificial Sequence
<220> FEATURE:
<223> OTHER INFORMATION: Synthetic sequence

<400> SEQUENCE: 91
tgctttcgat aagtccagac a                                            21

<210> SEQ ID NO 92
<211> LENGTH: 18
<212> TYPE: DNA
<213> ORGANISM: Artificial Sequence
<220> FEATURE:
<223> OTHER INFORMATION: Synthetic sequence

<400> SEQUENCE: 92
cctctgaggc tggaaaca                                                18

<210> SEQ ID NO 93
<211> LENGTH: 19
<212> TYPE: DNA
<213> ORGANISM: Artificial Sequence
<220> FEATURE:
<223> OTHER INFORMATION: Synthetic sequence

<400> SEQUENCE: 93
atccactgat cttccttgc                                               19
```

<210> SEQ ID NO 94
<211> LENGTH: 19
<212> TYPE: DNA
<213> ORGANISM: Artificial Sequence
<220> FEATURE:
<223> OTHER INFORMATION: Synthetic sequence

<400> SEQUENCE: 94
cagtgctgct tcagacaca                                                    19

<210> SEQ ID NO 95
<211> LENGTH: 21
<212> TYPE: DNA
<213> ORGANISM: Artificial Sequence
<220> FEATURE:
<223> OTHER INFORMATION: Synthetic sequence

<400> SEQUENCE: 95
cctttcttca agggtaaagg c                                                 21

<210> SEQ ID NO 96
<211> LENGTH: 20
<212> TYPE: DNA
<213> ORGANISM: Artificial Sequence
<220> FEATURE:
<223> OTHER INFORMATION: Synthetic sequence

<400> SEQUENCE: 96
tcgaatttct ctcctcccat                                                   20

<210> SEQ ID NO 97
<211> LENGTH: 18
<212> TYPE: DNA
<213> ORGANISM: Artificial Sequence
<220> FEATURE:
<223> OTHER INFORMATION: Synthetic sequence

<400> SEQUENCE: 97
ctgagtccac acaggttt                                                     18

<210> SEQ ID NO 98
<211> LENGTH: 23
<212> TYPE: DNA
<213> ORGANISM: Artificial Sequence
<220> FEATURE:
<223> OTHER INFORMATION: Synthetic sequence

<400> SEQUENCE: 98
cccatacttg ttgatggcaa tta                                               23

<210> SEQ ID NO 99
<211> LENGTH: 18
<212> TYPE: DNA
<213> ORGANISM: Artificial Sequence
<220> FEATURE:
<223> OTHER INFORMATION: Synthetic sequence

<400> SEQUENCE: 99
tcctgcgtgt gttctact                                                     18

<210> SEQ ID NO 100
<211> LENGTH: 19
<212> TYPE: DNA
<213> ORGANISM: Artificial Sequence
<220> FEATURE:

```
<223> OTHER INFORMATION: Synthetic sequence

<400> SEQUENCE: 100
agtcatcatg tacccagca                                                    19

<210> SEQ ID NO 101
<211> LENGTH: 20
<212> TYPE: DNA
<213> ORGANISM: Artificial Sequence
<220> FEATURE:
<223> OTHER INFORMATION: Synthetic sequence

<400> SEQUENCE: 101
cccaggatac tctcttcctt                                                   20

<210> SEQ ID NO 102
<211> LENGTH: 18
<212> TYPE: DNA
<213> ORGANISM: Artificial Sequence
<220> FEATURE:
<223> OTHER INFORMATION: Synthetic sequence

<400> SEQUENCE: 102
cactggatca actgcctc                                                     18

<210> SEQ ID NO 103
<211> LENGTH: 19
<212> TYPE: DNA
<213> ORGANISM: Artificial Sequence
<220> FEATURE:
<223> OTHER INFORMATION: Synthetic sequence

<400> SEQUENCE: 103
cagctgtcac acccagagc                                                    19

<210> SEQ ID NO 104
<211> LENGTH: 17
<212> TYPE: DNA
<213> ORGANISM: Artificial Sequence
<220> FEATURE:
<223> OTHER INFORMATION: Synthetic sequence

<400> SEQUENCE: 104
cgtatggtgc agggtca                                                      17

<210> SEQ ID NO 105
<211> LENGTH: 20
<212> TYPE: DNA
<213> ORGANISM: Artificial Sequence
<220> FEATURE:
<223> OTHER INFORMATION: Synthetic sequence

<400> SEQUENCE: 105
tctggactgt ctggttgaat                                                   20

<210> SEQ ID NO 106
<211> LENGTH: 19
<212> TYPE: DNA
<213> ORGANISM: Artificial Sequence
<220> FEATURE:
<223> OTHER INFORMATION: Synthetic sequence

<400> SEQUENCE: 106
cctgtacacc aagcttcat                                                    19
```

```
<210> SEQ ID NO 107
<211> LENGTH: 19
<212> TYPE: DNA
<213> ORGANISM: Artificial Sequence
<220> FEATURE:
<223> OTHER INFORMATION: Synthetic sequence

<400> SEQUENCE: 107
ccatgcccac tttcttgta                                                    19

<210> SEQ ID NO 108
<211> LENGTH: 20
<212> TYPE: DNA
<213> ORGANISM: Artificial Sequence
<220> FEATURE:
<223> OTHER INFORMATION: Synthetic sequence

<400> SEQUENCE: 108
cattggtggt gaagctcttg                                                   20

<210> SEQ ID NO 109
<211> LENGTH: 18
<212> TYPE: DNA
<213> ORGANISM: Artificial Sequence
<220> FEATURE:
<223> OTHER INFORMATION: Synthetic sequence

<400> SEQUENCE: 109
cgtggactga gatgcatt                                                     18

<210> SEQ ID NO 110
<211> LENGTH: 21
<212> TYPE: DNA
<213> ORGANISM: Artificial Sequence
<220> FEATURE:
<223> OTHER INFORMATION: Synthetic sequence

<400> SEQUENCE: 110
ttcatgtcgt tgaacacctt g                                                 21

<210> SEQ ID NO 111
<211> LENGTH: 21
<212> TYPE: DNA
<213> ORGANISM: Artificial Sequence
<220> FEATURE:
<223> OTHER INFORMATION: Synthetic sequence

<400> SEQUENCE: 111
cattttggct tttaggggta g                                                 21

<210> SEQ ID NO 112
<211> LENGTH: 17
<212> TYPE: DNA
<213> ORGANISM: Artificial Sequence
<220> FEATURE:
<223> OTHER INFORMATION: Synthetic sequence

<400> SEQUENCE: 112
ggcagaagcg agacttt                                                      17

<210> SEQ ID NO 113
<211> LENGTH: 17
<212> TYPE: DNA
<213> ORGANISM: Artificial Sequence
<220> FEATURE:
<223> OTHER INFORMATION: Synthetic sequence
```

```
<400> SEQUENCE: 113
gcacatagga ggtggca                                                  17

<210> SEQ ID NO 114
<211> LENGTH: 17
<212> TYPE: DNA
<213> ORGANISM: Artificial Sequence
<220> FEATURE:
<223> OTHER INFORMATION: Synthetic sequence

<400> SEQUENCE: 114
gcggacttta ccgtgac                                                  17
```

MOLECULAR DIAGNOSIS AND TYPING OF LUNG CANCER VARIANTS

CROSS REFERENCE TO RELATED APPLICATIONS

This application is a continuation of U.S. Ser. No. 14/334,855, filed Jul. 18, 2014 which is a continuation of U.S. Ser. No. 12/602,640, filed Feb. 16, 2010 which is a § 371 U.S. National Stage of International Application PCT/US2008/065489, filed Jun. 2, 2008, which claims the benefit of U.S. Provisional Appn. 60/941,520, filed Jun. 1, 2007, the contents of which are hereby incorporated by reference in their entirety.

SEQUENCE LISTING

Incorporation-by-Reference of Material Submitted Electronically

This application contains a sequence listing, please enter the sequence listing into the application. It has been submitted electronically via EFS-Web as an ASCII text file entitled "150-9-CON2_SEQ_ST25.txt". The sequence listing is 22,346 bytes in size, and was created on Jun. 30, 2017. It is hereby incorporated by reference in its entirety.

STATEMENT REGARDING FEDERALLY SPONSORED RESEARCH OR DEVELOPMENT

This invention was made with government support under Grant Number RR023248 awarded by the National Institutes of Health. The government has certain rights in the invention.

FIELD OF THE INVENTION

The present invention relates to methods for characterizing lung cancer subtypes and for evaluating the prognosis of a subject inflicted with lung cancer.

BACKGROUND OF THE INVENTION

Lung cancer is the leading cause of cancer deaths both in the United States and worldwide. Despite many classification schemes and ongoing clinical trials, there has been overall disappointing progress in the field of clinical diagnostics and therapeutics. Approximately 172,000 tumors of the lung were diagnosed in 2005 with an estimated 163,000 deaths, more than colon, breast, and prostate combined. At least 75% of patients present with locally advanced disease. Although there has been much effort to improve screening using technology such as high-resolution CT, these methods often produce false positive results and usually do not change outcome. Thus, even small tumors detected early present a significant threat to patients with postoperative 5-year survival rates for stage I lung cancer estimated between 47 to 63 percent. For patients with advanced disease the prognosis is worse with median survivals well under a year. In general, palliative therapy is effective but not sustainable and the average impact on overall survival is approximately 3 months. At the population level the underlying cause of lung cancer is clearly tobacco use, with 90% of all lung cancers attributed directly to smoking. Smoking is so tightly correlated with lung cancer that it confounds definitive association with most other risk factors; although asbestos, radon, and a number of lung irritants are generally accepted as lung cancer risk factors. A genetic association is strongly suspected, however, the exact mechanism remains to be determined outside of a select group of rare Mendelian cancer syndromes.

SUMMARY OF THE INVENTION

Compositions and methods useful in determining the major morphological types of lung cancer are provided. The methods comprise detecting expression of at least one gene or biomarker in a sample. The expression of the gene or biomarker is indicative of the lung tumor subtype. The compositions comprise subsets of genes that are monitored for gene expression. The gene expression is capable of distinguishing between normal lung parenchyma and the major morphological types of lung cancer. The gene expression and somatic mutation data are useful in developing a complete classification of lung cancer that is prognostic and predictive for therapeutic response. The methods are suited for analysis of paraffin-embedded tissues.

Methods of the invention include means for monitoring gene or biomarker expression including PCR and antibody-based detection. The biomarkers of the invention are genes and/or proteins that are selectively expressed at a high or low level in certain tumor subtypes. Biomarker expression can be assessed at the protein or nucleic acid level. In some embodiments, immunocytochemistry techniques are provided that utilize antibodies to detect the expression of biomarker proteins in samples. In this aspect of the invention, at least one antibody directed to a specific biomarker of interest is used. Expression can also be detected by nucleic acid-based techniques, including, for example, hybridization and RT-PCR. Kits comprising reagents for practicing the methods of the invention are further provided.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 1:
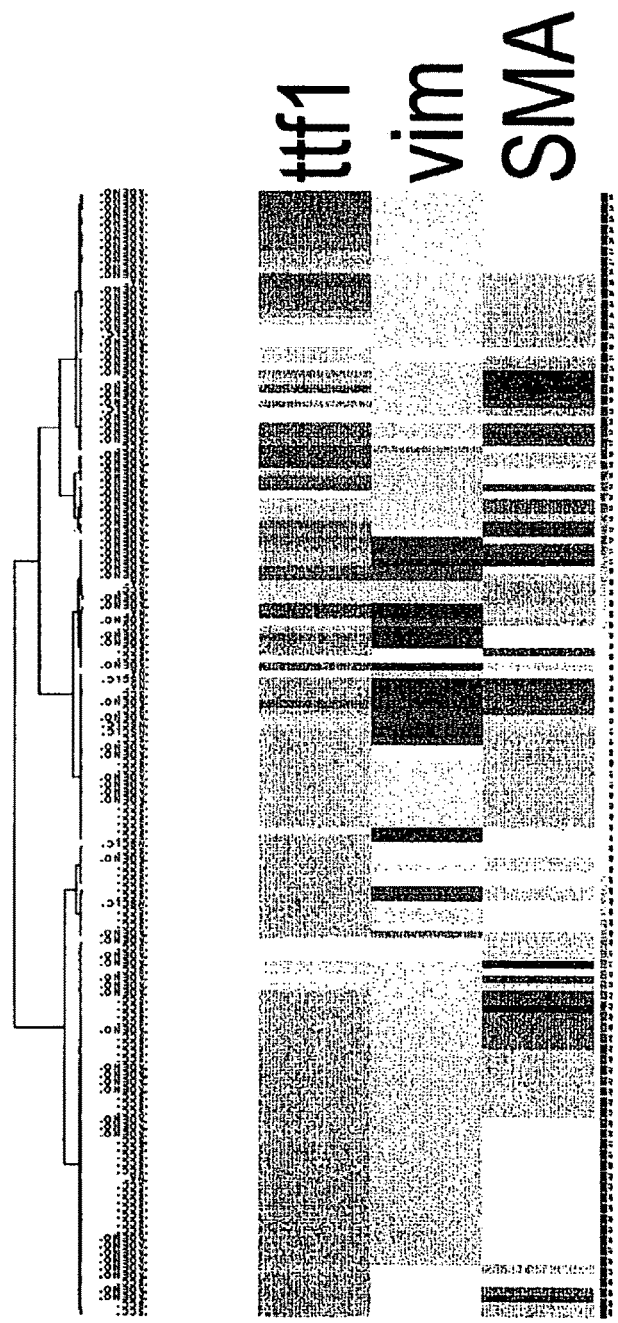
FIG. 1 shows protein clustering of the entire set of 152 evaluable NSCLC.
Figure 4:
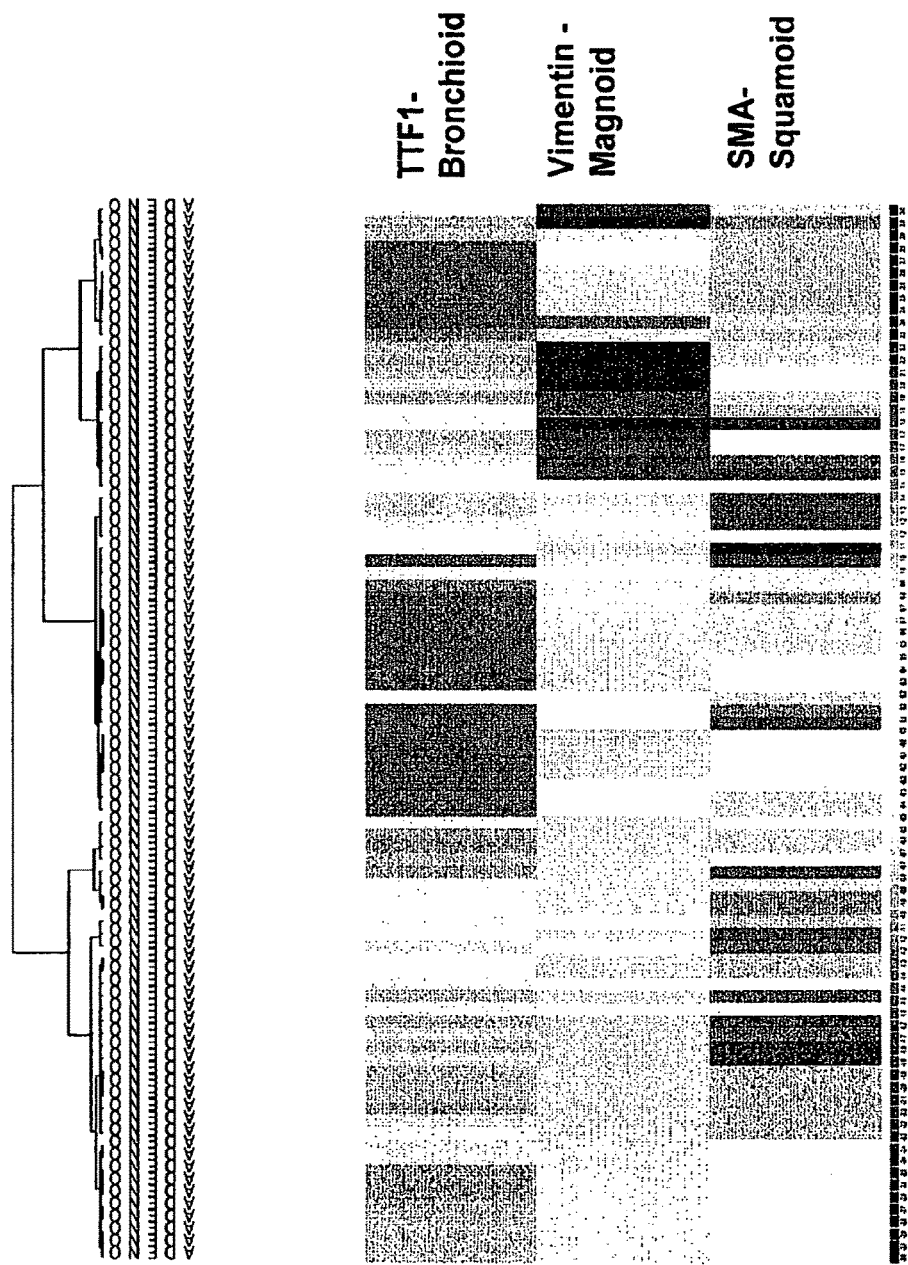

FIG. 4 shows protein clustering of the adenocarcinoma subset (n=85). 152 of 187 samples were evaluable. 16 samples were excluded because the tumor or the core was absent, and 19 were excluded due to <10% cells staining for the marker. Of the 152 evaluable samples, 85 were adenocarcinoma. The staining patterns of the 85 samples are ordered by hierarchical agglomerative clustering, and show distinct clustering into three groups (FIG. 1). The Chi square test p value for this distribution of staining is $p<2.2\times10^{-16}$.

Figure 5:
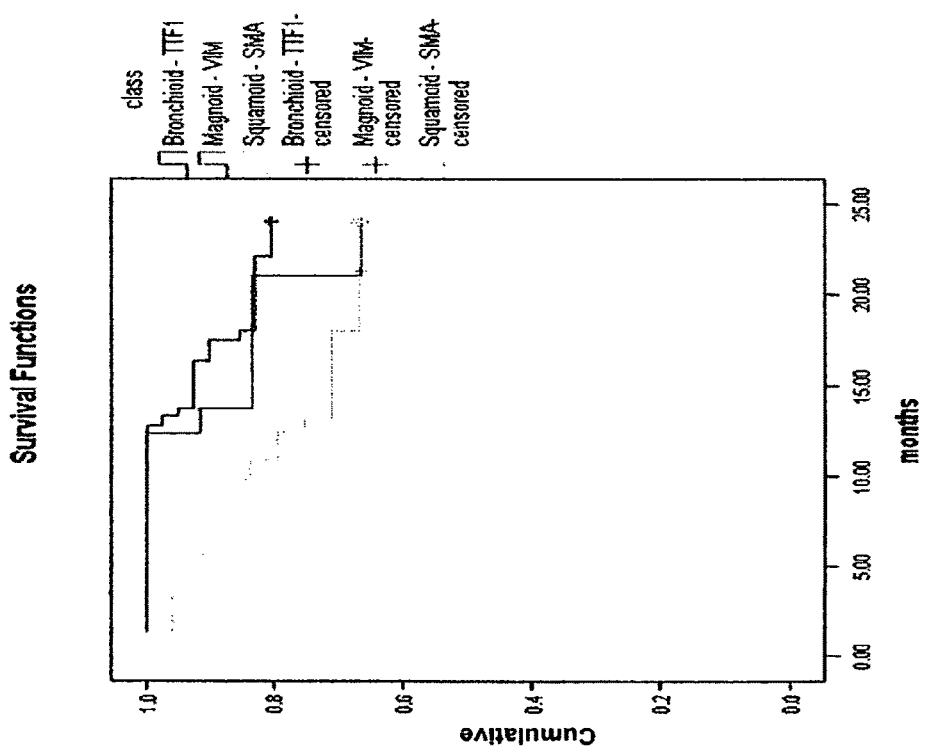

FIG. 5 shows survival by tumor subtype. The clinical phenotype associated with the 3 molecular subtypes of lung adenocarcinoma reproduces previous work. Most notably, there are clear differences in the frequency and pattern of recurrence (table 1) by tumor subtype and survival.

Figure 6:
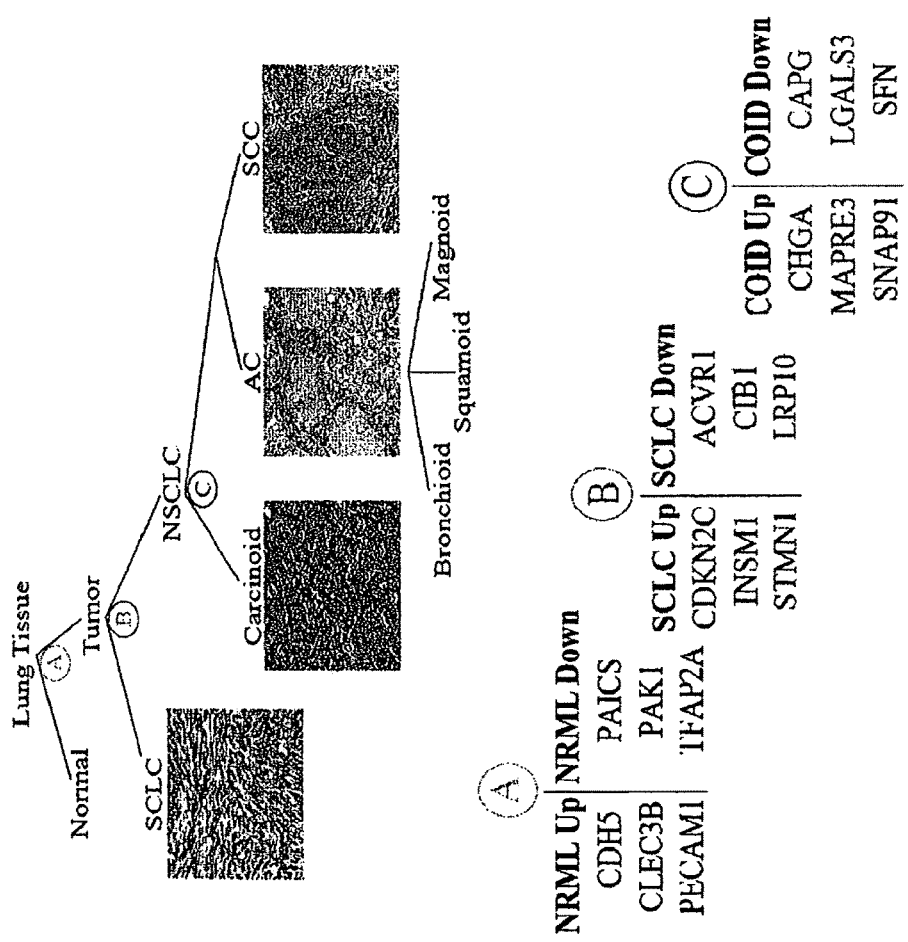

FIG. 6 shows the classification of lung cancer using a minimized qRT-PCR assay. 52-classifier genes were identified to determine histological and molecular subtypes of lung cancer. Up-regulated and down-regulated genes were selected for determining histological subtypes (A-C), and additional molecular subtypes of AC comprised of bronchioid, squamoid, and magnoid.

Figure 7:
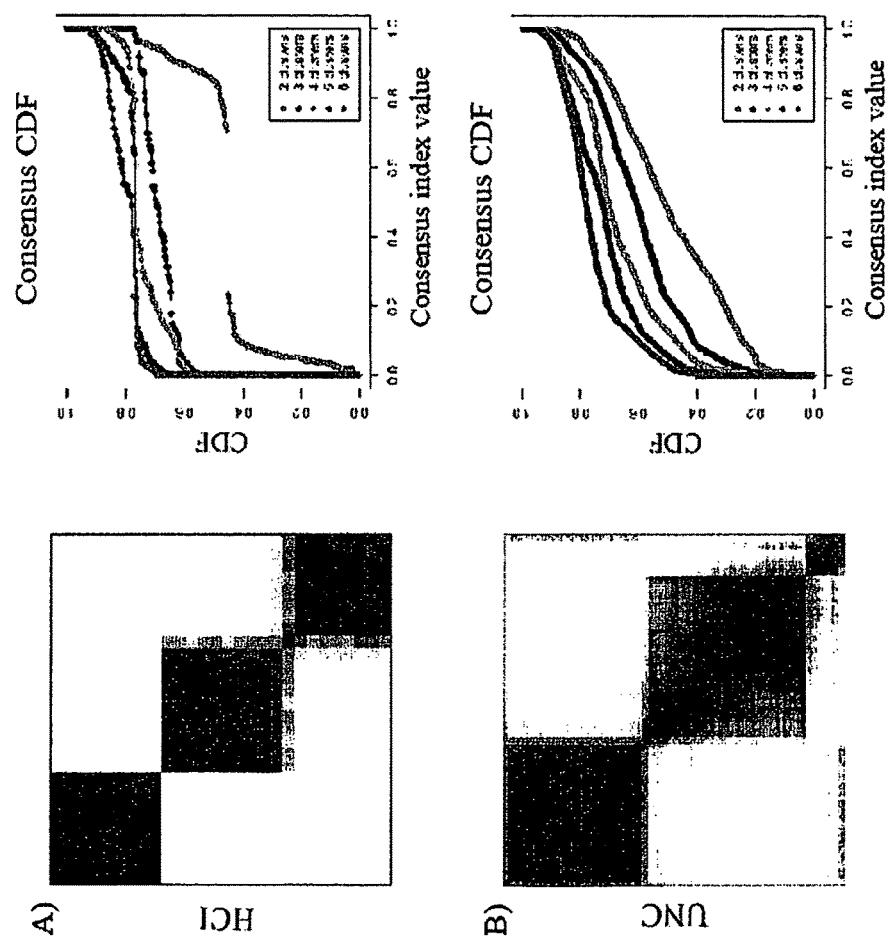

FIG. 7 shows a consensus clustering for the HCI (A) and UNC (B) adenocarcinoma samples. The adjacent CDF curves demonstrate the largest change in area under the curve from two to three clusters, indicating three as the optimal number of clusters. This parallels clustering results from microarray data.

Figure 8:
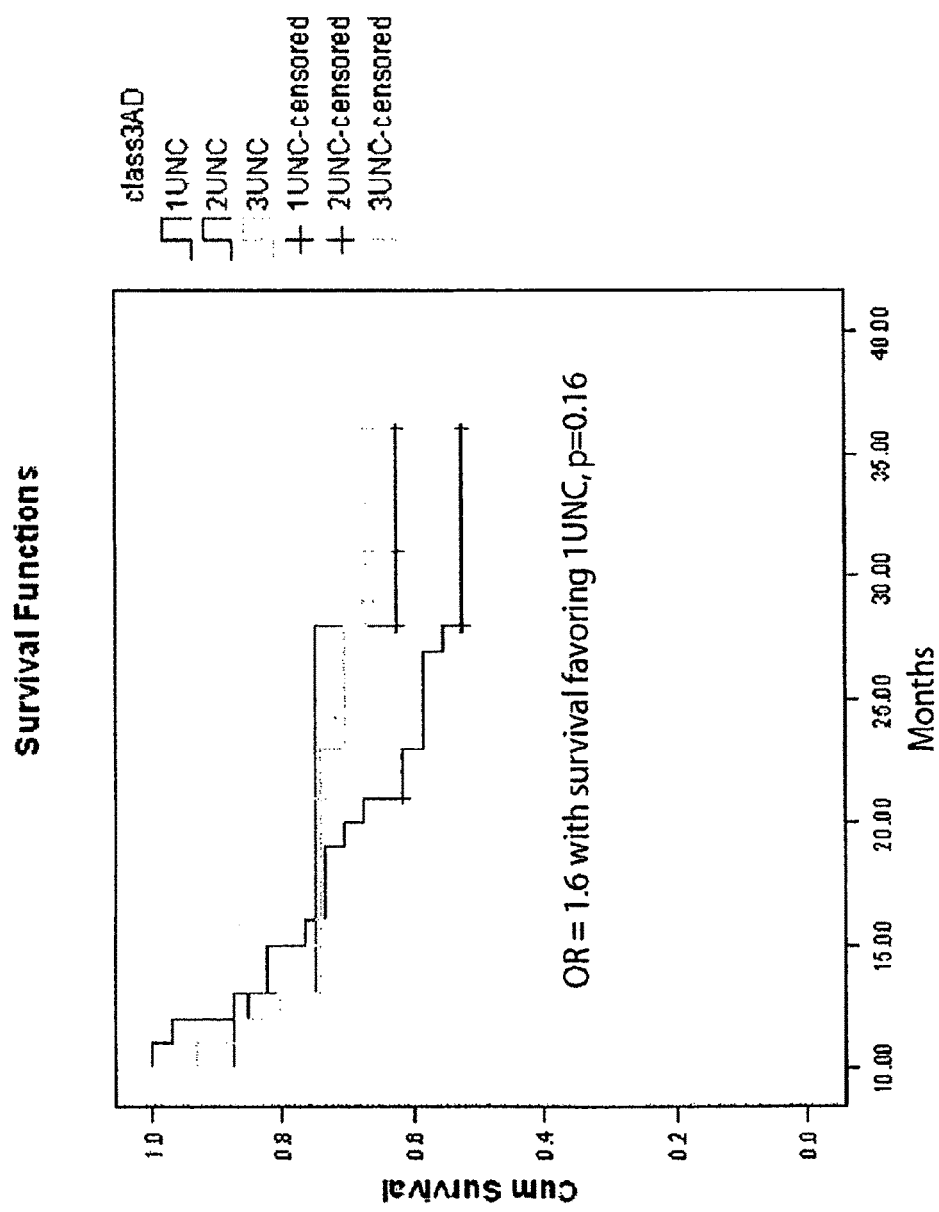

FIG. 8 shows survival by adenocarcinoma subtype. The clinical phenotype associated with the 3 molecular subtypes of lung adenocarcinoma reproduces previous work.

Figure 9:
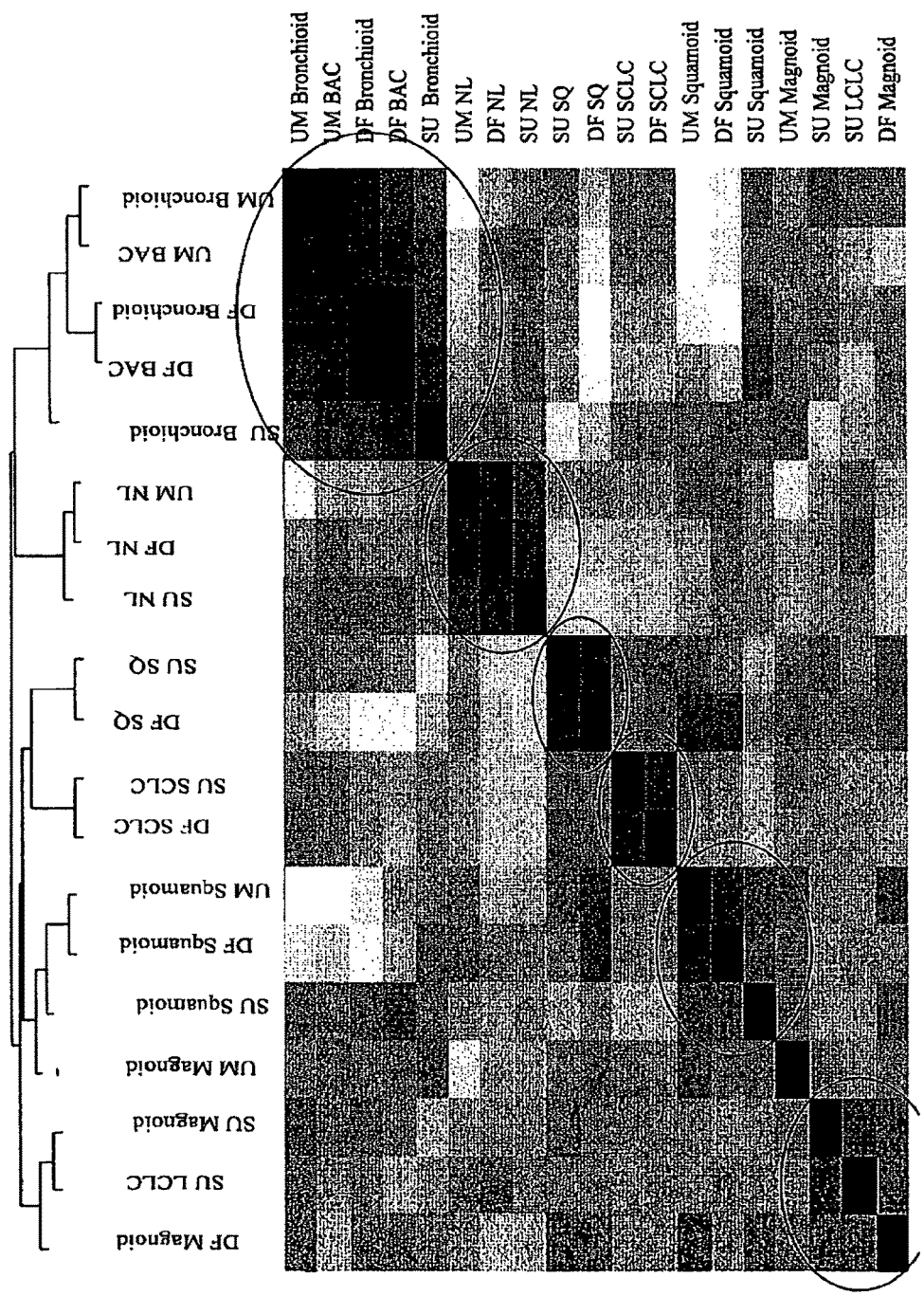

FIG. 9 shows the classification of bronchoid, squamoid and magnoid subtypes. Each sample was assigned uniquely to one of 3 adenocarcinoma subtypes as described in the text. Nine centroids were prepared from these data (3 tumor subtypes×3 studies). Additional centroids were prepared for the major tumor histologies present in the cohorts for a total of 19 centroids. Hierarchical agglomerative clustering was performed using a distance measure of 1-pearsons correlation across all reliable 2553 gene correlations. The results of clustering are shown as the branched tree dendrogram at the top of the figure. Below the dendrogram, the pair-wise relationships between each of the centroids are displayed graphically as a series of shaded pixels. Each pixel represents a pair-wise correlation between centroids named by the row and column with darker shading corresponding to higher correlation. The figure shows that the tightest correlations are between histologic groups, indicated by groups of circled pixels. Correlations of similar strength are indicated between adenocarcinoma subtypes in essentially every case. Additionally, the figure demonstrates interesting patterns of low centroid correlation. The squamoid and bronchioid subtypes have low pair-wises correlations, and in fact the squamoid subtype is more correlated with centroids derived from squamous cell carcinoma. The single centroid with an overall ambiguous set of pair-wise correlations is the Magnoid centroid derived from the Michigan cohort which nonetheless was grouped at a position intermediated to the Magnoids and squamoids in the dendrogram. Abbreviations: DF=Dana Farber, SU=Stanford University, UM=University of Michigan.

Figure 10:
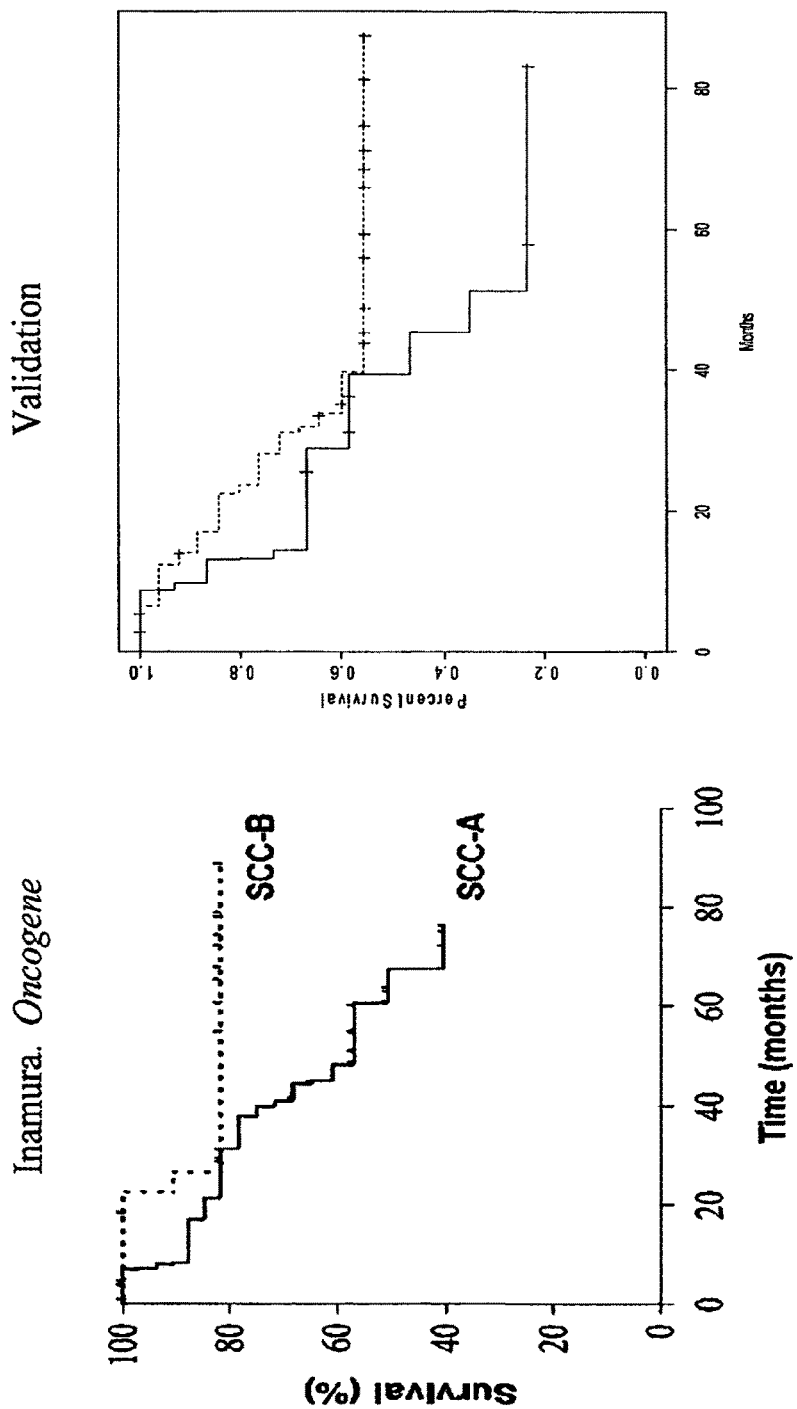

FIG. 10 shows survival by SCC subtype in two independent cohorts of lung cancer patients.

FIG. 11 shows the correlation of tumor morphology as determined by light microscopy compared to that determined by gene expression profiling from FFPE samples.

Figure 12:
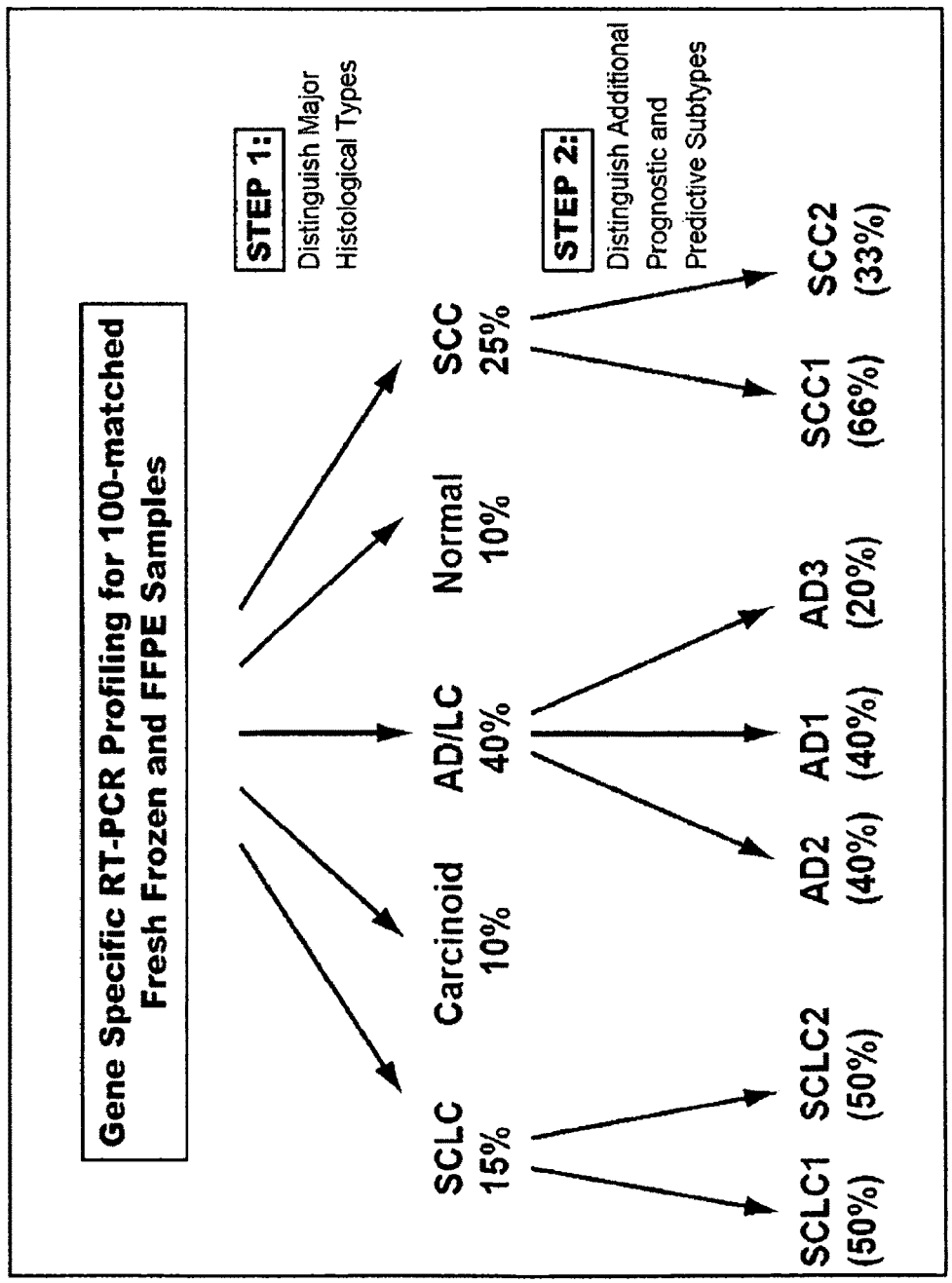

FIG. 12 is a Diagnostic Decision Tree for Lung Cancer. The Calibrated Classifier (CC), derived from the 500 gene set (PDC), is used in the qRT-PCR assay to first distinguish the major histological types of lung cancer and then further subtype based on the molecular classification. The numbers next to each histological type show the distribution of samples, with the expected frequencies of subtypes within each class provided below in parentheses.

Figure 13:
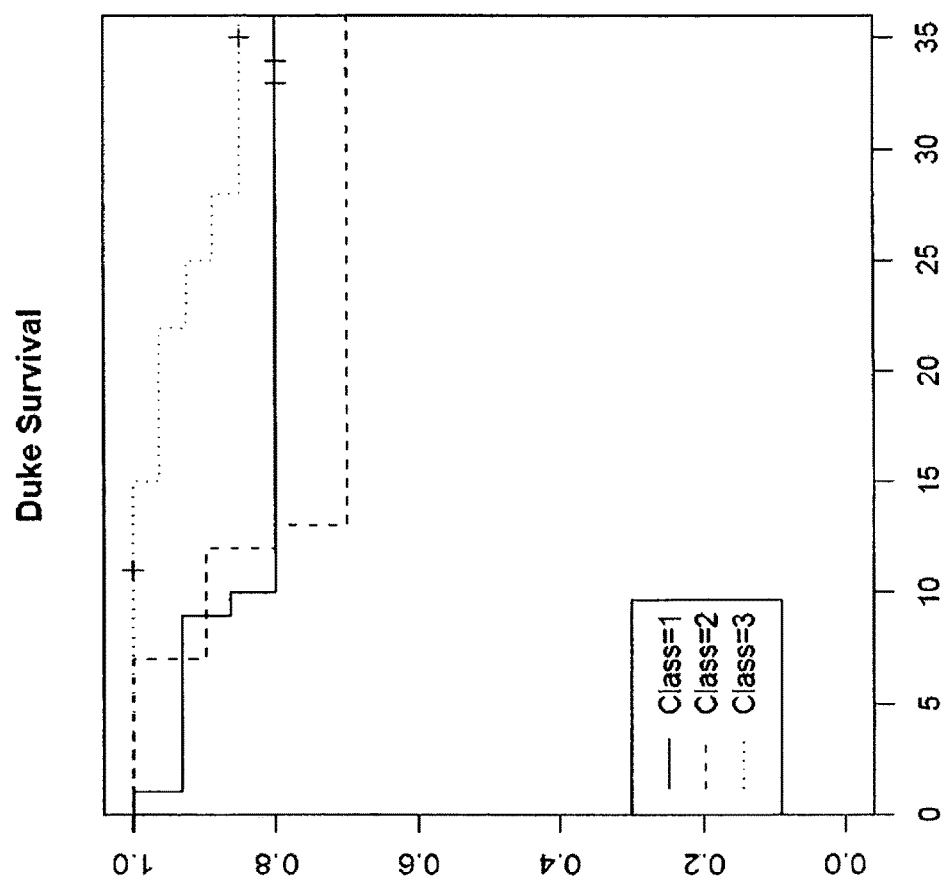

FIG. 13 shows a survival plot for Class I, Class II, and Class III in the Duke samples.

Figure 14:
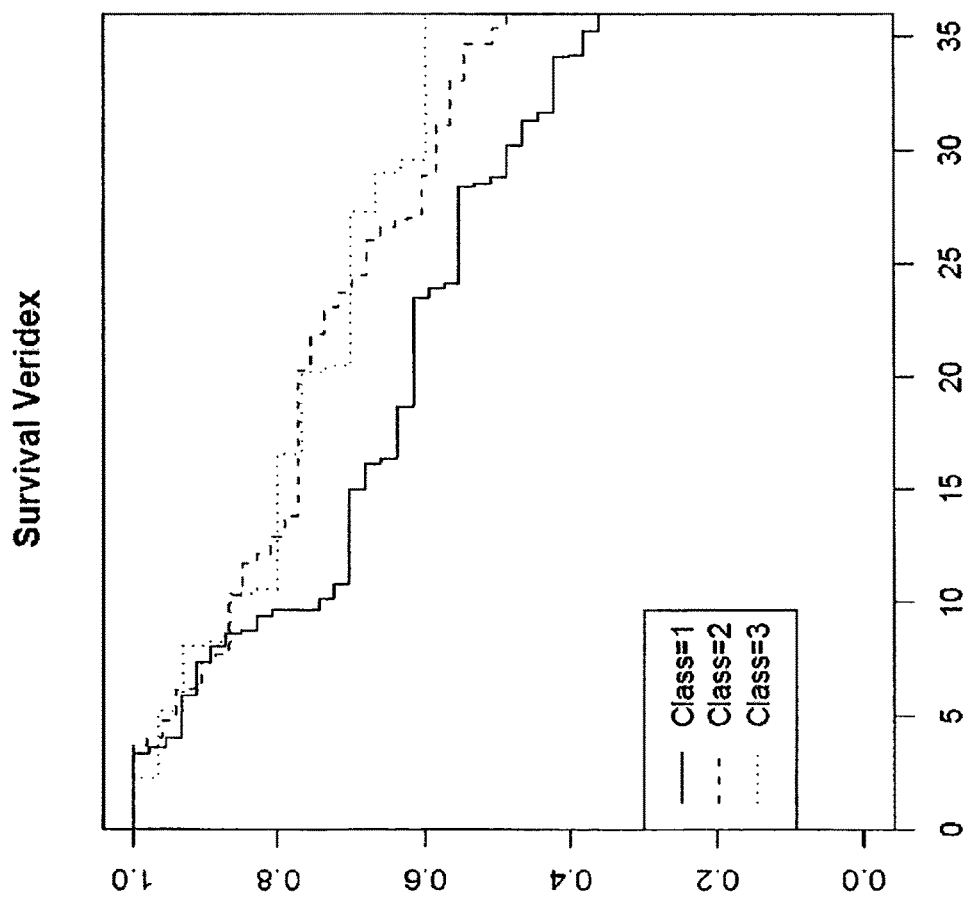

FIG. 14 shows a survival plot for Class I, Class II, and Class III in the Veridex samples.

DETAILED DESCRIPTION OF THE INVENTION

The present invention provides compositions and methods for identifying or diagnosing lung cancer. That is, the methods are useful for molecularly defining subsets of lung cancer. The methods provide a classification of lung cancer that is prognostic and predictive for therapeutic response. While a useful term for epidemiologic purposes, "lung cancer" does not refer to a specific disease, but rather represents a heterogeneous collection of tumors of the lung, bronchus, and pleura. For practical purposes, lung cancer is generally divided into two histological subtypes—small cell lung cancer (SCLC) and non-small cell lung cancer (NSCLC). These main tumor types present at different frequencies, different anatomic locations, have different predilections for metastasis, respond differently to therapy, and are likely derived from different cell progenitors. For instance, SCLC often presents near the central bronchus, has neuroendocrine features, and responds initially to therapy but often recurs. Most lung cancers are classified as NSCLC (>85%), which is a diverse group with subtypes occurring throughout the respiratory tract. Adenocarcinoma (AD) and squamous cell carcinomas (SCC), the 2 main subtypes of NSCLC, are diagnosed at near equal frequency but are often found at different locations with SCC occurring more centrally. The 6th edition of the consensus classification of lung cancers developed by the World Health Organization (WHO) describes no fewer than 90 malignant morphologic classes and variants. There is often heterogeneity, especially in larger tumors>1.5 cm, making morphological classification more difficult and leading to designations such as adeno-squamous carcinoma. The methods of the invention provide a means for determining the cellular and molecular origins of lung cancer and thus, provide for more accurate diagnoses and treatments.

In one embodiment, the expression profile associated with the gene cassettes described herein is useful for distinguishing between normal and tumor samples. In another embodiment, the expression profile can distinguish between small cell lung carcinoma (SCLC) and non-small cell lung carcinoma (NSCLC). In another embodiment, NSCLC can be further classified as carcinoid, adenocarcinoma, or squamous cell carcinoma. In yet another embodiment, adenocarcinomas can be characterized as bronchoid, squamoid, or magnoid. The characterization of bronchoid, squamoid, and magnoid adenocarcinomas using tumor biopsy tissue has been described in Hayes et al. (2006) *J. Clin Oncol.* 24(31):5079-90.

"Diagnosing lung tumor subtypes" or "determining subsets of lung cancer" is intended to include, for example, diagnosing or detecting the presence and type of lung cancer, monitoring the progression of the disease, and identifying or detecting cells or samples that are indicative of subtypes. The terms diagnosing, detecting, and identifying lung cancer subtypes are used interchangeably herein.

The methods of the invention also find use in predicting response to chemotherapy, particularly first-line chemotherapy. Chemotherapeutic response is improved by more accurately assigning tumor subtypes. Likewise, treatment regimens can be formulated based on the tumor subtype. For example, clinical trials have shown convincing evidence that the VEGF inhibitor, bevacizumab, is effective in the treatment of NSCLC. The drug carries a concerning toxicity of tumor necrosis and associated fatal pulmonary hemorrhage, an event overwhelmingly associated with tumors of squamous cell histology. Accordingly, there has been an active attempt to exclude such patients from treatment with the drug. As drugs of this class increasingly enter clinical practice, the methods of the invention will be useful to more accurately diagnose squamous cell carcinoma even from limited tissue samples.

Overview

Expression profiles using the discriminative genes disclosed herein provide valuable molecular tools for specifically classifying lung cancer types and subtypes, and for evaluating therapeutic efficacy in treating lung cancer.

Accordingly, the invention provides methods for screening a subject for lung cancer (diagnostic) including classification into molecular subtypes, methods for monitoring the progression of lung cancer in a subject, and methods for monitoring the efficacy of certain therapeutic treatments for lung cancer.

In some instances, a single discriminating gene is capable of classifying types and subtypes of lung cancer with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, whereas, in other instances, a combination of predictive genes is used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

In some instances, a single predictive gene is capable of classifying lung cancer types or subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, whereas, in other instances, a combination or plurality of discriminative genes is used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

The present invention also encompasses a system capable of classifying subjects according to lung cancer status, including distinguishing between various subtypes of lung cancer not detectable using current methods. This system is capable of processing a large number of subjects and subject variables such as expression profiles and other diagnostic criteria. The methods described herein can also be used for "pharmacometabonomics," in analogy to pharmacogenomics, e.g., predictive of response to therapy. In this embodiment, subjects could be divided into "responders" and "nonresponders" using the expression profile as evidence of "response," and features of the expression profile could then be used to target future subjects who would likely respond to a particular therapeutic course.

The methods are also useful for evaluating clinical response to therapy, as well as for endpoints in clinical trials for efficacy of new therapies. The extent to which sequential diagnostic expression profiles move towards normal can be used as one measure of the efficacy of the candidate therapy.

The expression profile can be used in combination with other diagnostic methods including histochemical, immunohistochemical, cytologic, immunocytologic, and visual diagnostic methods including histologic or morphometric evaluation of lung tissue.

Expression Profiling

In one embodiment of the present invention, lung cancer status is assessed through the evaluation of expression patterns, or profiles, of a plurality of discriminative genes or biomarkers in one or more subject samples. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the invention. Accordingly, a subject can be diagnosed with lung cancer (including various types, subtypes, or grades thereof), can present with one or more symptoms of lung cancer, or a predisposing factor, such as a family (genetic) or medical history (medical) factor, for lung cancer, can be undergoing treatment or therapy for lung cancer, or the like. Alternatively, a subject can be healthy with respect to any of the aforementioned factors or criteria. It will be appreciated that the term "healthy" as used herein, is relative to lung cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more other cancers.

As used herein, an "expression profile" comprises one or more values corresponding to a measurement of the relative abundance, presence, or absence of expression of a discriminative gene. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject.

In various embodiments of the present invention, the expression profile derived from a subject is compared to a reference expression profile. A "reference expression profile" can be a profile derived from the subject prior to treatment or therapy; can be a profile produced from the subject sample at a particular time point (usually prior to or following treatment or therapy, but can also include a particular time point prior to or following diagnosis of lung cancer); or can be derived from a healthy individual or a pooled reference from healthy individuals. A reference expression profile can be generic for lung cancer, or can be specific to different types or subtypes of lung cancer.

The reference expression profile can be compared to a test expression profile. A "test expression profile" can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from the same subject or to a profile obtained from a healthy individual.

The biomarkers of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include any expression product or portion thereof of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

A "biomarker" is any gene or protein whose level of expression in a tissue or cell is altered compared to that of a normal or healthy cell or tissue. The detection, and in some cases the level, of the biomarkers of the invention permits the differentiation of samples.

The biomarkers of the invention include any gene or protein that is selectively expressed in lung cancer cells, as defined herein above. Sample biomarker genes are listed in Table 1, below. The first portion of the table represents the gene lists for distinguishing types and subtypes. The middle portion of the table represents genes that are useful for distinguishing the three subtypes of squamous cell carcinoma, as well as the relative "up" or "down" levels of expression for each gene. The last portion of the table lists the same genes as the first portion, but with the relative "up" or "down" indications for expression levels. The comparisons are depicted in FIG. 6. Thus, the level of expression of (for example) CAPG is said to be "down" relative to the expression of CAPG in ACC/SCC lung cancer types. Although the methods of the invention require the detection of at least one biomarker in a patient sample, 2, 3, 4, 5, 6, 7, 8, 9, 10 or more biomarkers may be used to practice the present invention.

TABLE 1

Classification, Housekeeping Genes, Corresponding Primer Sets, and Relative Expression Levels

| Gene symbol | Gene name | Forward primer | SEQ ID | Reverse primer | SEQ ID |
|---|---|---|---|---|---|
| Normal classifier gene list | | | | | |
| CDH5 | cadherin 5, type 2, VE-cadherin (vascular epithelium) | AAGAGAGATTG GATTTGGAACC | 1 | TTCTTGCGACTC ACGCT | 58 |
| CLEC3B | C-type lectin domain family 3, member B | CCAGAAGCCCA AGAAGATTGTA | 2 | GCTCCTCAAACA TCTTTGTGTTCA | 59 |
| PAICS | phosphoribosylami noimidazole carboxylase, phosphoribosylami noimidazole succinocarboxamide synthetase | AATCCTGGTGT CAAGGAAG | 3 | GACCACTGTGGG TCATTATT | 60 |
| PAK1 | p21/Cdc42/Rac1- activated kinase 1 (STE20 homolog, yeast) | GGACCGATTTT ACCGATCC | 4 | GAAATCTCTGGC CGCTC | 61 |
| PECAM1 | platelet/endothelial cell adhesion molecule (CD31 antigen) | ACAGTCCAGAT AGTCGTATGT | 5 | ACTGGGCATCAT AAGAAATCC | 62 |
| TFAP2A | transcription factor AP-2 alpha (activating enhancer binding protein 2 alpha) | GTCTCCGCCAT CCCTAT | 6 | ACTGAACAGAAG ACTTCGT | 63 |
| SCLC classifier gene list | | | | | |
| ACVR1 | activin A receptor, type I | ACTGGTGTAAC AGGAACAT | 7 | AACCTCCAAGTG GAAATTCT | 64 |
| CDKN2C | cyclin-dependent kinase inhibitor 2C (p18, inhibits CDK4) | TTTGGAAGGAC TGCGCT | 8 | TCGGTCTTTCAA ATCGGGATTA | 65 |
| CIB1 | calcium and integrin binding 1 (calmyrin) | CACGTCATCTC CCGTTC | 9 | CTGCTGTCACAG GACAAT | 66 |
| INSM1 | insulinoma- associated 1 | ATTGAACTTCC CACACGA | 10 | AAGGTAAAGCCA GACTCCA | 67 |
| LRP10 | low density lipoprotein receptor-related protein 10 | GGAACAGACTG TCACCAT | 11 | GGGAGCGTAGGG TTAAG | 68 |

TABLE 1-continued

Classification, Housekeeping Genes, Corresponding
Primer Sets, and Relative Expression Levels

| | | | | | |
|---|---|---|---|---|---|
| STMN1 | stathmin 1/ oncoprotein 18 | TCAGAGTGTGG TCAGGC | 12 | CAGTGTATTCTG CACAATCAAC | 69 |

Carcinoid classifiers gene list

| | | | | | |
|---|---|---|---|---|---|
| CAPG | capping protein (actin filament), gelsolin-like | GGGACAGCTTC AACACT | 13 | GTTCCAGGATGT TGGACTTTC | 70 |
| CHGA | chromogranin A (parathyroid secretory protein 1) | CCTGTGAACAG CCCTATG | 14 | GGAAAGTGTGTC GGAGAT | 71 |
| LGALS3 | lectin, galactoside-binding, soluble, 3 (galectin 3) | TTCTGGGCACG GTGAAG | 15 | AGGCAACATCAT TCCCTC | 72 |
| MAPRE3 | microtubule-associated protein, RP/EB family, member 3 | GGCCAAACTAG AGCACGAATA | 16 | GTCAACACCCAT CTTCTTGAAA | 73 |
| SFN | stratifin | TCAGCAAGAAG GAGATGCC | 17 | CGTAGTGGAAGA CGGAAA | 74 |
| SNAP91 | synaptosomal-associated protein, 91 kDa homolog (mouse) | GTGCTCCCTCT CCATTAAGTA | 18 | CTGGTGTAGAAT TAGGAGACGTA | 75 |

AC/SCC classifier gene list

| | | | | | |
|---|---|---|---|---|---|
| ABCC5 | ATP-binding cassette, sub-family C (CFTR/MRP), member 5 | CAAGTTCAGGA GAACTCGAC | 19 | GGCATCAAGAGA GAGGC | 76 |
| ALDH3B1 | aldehyde dehydrogenase 3 family, member B1 | GGCTGTGGTTA TGCGATAG | 20 | GATAAAGAGTTA CAAGCTCCTCTG | 77 |
| ANTXR1 | anthrax toxin receptor 1 | ACCCGAGGAAC AACCTTA | 21 | TCTAGGCCTTGA CGGAT | 78 |
| BMP7 | bone morphogenetic protein 7 (osteogenic protein 1) | CCCTCTCCATT CCCTACA | 22 | TTTGGGCAAACC TCGGTAA | 79 |
| CACNB1 | calcium channel, voltage-dependent, beta 1 subunit | CAGAGCGCCAG GCATTA | 23 | GCACAGCAAATG CCACT | 80 |
| CBX1 | chromobox homolog 1 (HP1 beta homolog Drosophila) | CCACTGGCTGA GGTGTTA | 24 | CTTGTCTTTCCC TACTGTCTTAC | 81 |
| CYB5B | cytochrome b5 type B (outer mitochondrial membrane) | TGGGCGAGTCT ACGATG | 25 | CTTGTTCCAGCA GAACCT | 82 |
| DOK1 | docking protein 1, 62 kDa (downstream of tyrosine kinase 1) | CTTTCTGCCCT GGAGATG | 26 | CAGTCCTCTGCA CCGTTA | 83 |
| DSC3 | desmocollin 3 | GCGCCATTTGC TAGAGATA | 27 | CATCCAGATCCC TCACAT | 84 |
| FEN1 | flap structure-specific endonuclease 1 | AGAGAAGATGG GCAGAAAG | 28 | CCAAGACACAGC CAGTAAT | 85 |

TABLE 1-continued

Classification, Housekeeping Genes, Corresponding
Primer Sets, and Relative Expression Levels

| Gene | Description | Forward Primer | SEQ ID | Reverse Primer | SEQ ID |
|---|---|---|---|---|---|
| FOXH1 | forkhead box H1 | GCCCAGATCAT CCGTCA | 29 | TTTCCAGCCCTC GTAGTC | 86 |
| GJB2 | gap junction protein, beta 5 connexin 31.1) | ACCACAAGGAC TTCGAC | 30 | GGGACACAGGGA AGAAC | 87 |
| HOXD1 | homeobox D1 | GCTCCGCTGCT ATCTTT | 31 | GTCTGCCACTCT GCAAC | 88 |
| HPN | hepsin (transmembrane protease, serine 1) | AGCGGCCAGGT GGATTA | 32 | GTCGGCTGACGC TTTGA | 89 |
| HYAL2 | hyaluronoglucosam inidase 2 | ATGGGCTTTGG GAGCATA | 33 | GAACAAGTCAGT CTAGGGAATAC | 90 |
| ICA1 | islet cell autoantigen 1, 69 kDa | GACCTGGATGC CAAGCTA | 34 | TGCTTTCGATAA GTCCAGACA | 91 |
| ICAM5 | intercellular adhesion molecule 5, telencephalin | CCGGCTCTTGG AAGTTG | 35 | CCTCTGAGGCTG GAAACA | 92 |
| ITGA6 | integrin, alpha 6 | ACGCGGATCGA GTTTGATAA | 36 | ATCCACTGATCT TCCTTGC | 93 |
| LIPE | lipase, hormone-sensitive | CGCAAGTCCCA GAAGAT | 37 | CAGTGCTGCTTC AGACACA | 94 |
| ME3 | malic enzyme 3, NADP(+)-dependent, mitochondrial | CGCGGATACGA TGTCAC | 38 | CCTTTCTTCAAG GGTAAAGGC | 95 |
| MGRN1 | mahogunin, ring finger 1 | GAACTCGGCCT ATCGCT | 39 | TCGAATTTCTCT CCTCCCAT | 96 |
| MYBPH | myosin binding protein H | TCTGACCTCAT CATCGGCAA | 40 | CTGAGTCCACAC AGGTTT | 97 |
| MYO7A | myosin VIIA | GAGGTGAAGCA AACTACGGA | 41 | CCCATACTTGTT GATGGCAATTA | 98 |
| NFIL3 | nuclear factor, interleukin 3 regulated | ACTCTCCACAA AGCTCG | 42 | TCCTGCGTGTGT TCTACT | 99 |
| PIK3C2A | phosphoinositide-3-kinase, class 2, alpha polypeptide | GGATTTCAGCT ACCAGTTACTT | 43 | AGTCATCATGTA CCCAGCA | 100 |
| PLEKHA6 | pleckstrin homology domain containing, family A member 6 | TTCGTCCTGGT GGATCG | 44 | CCCAGGATACTC TCTTCCTT | 101 |
| PSMD14 | proteasome (prosome, macropain) 26 S subunit, non-ATPase, 14 | AGTGATTGATG TGTTTGCTATG | 45 | CACTGGATCAAC TGCCTC | 102 |
| SCD5 | stearoyl-CoA desaturase 5 | CAAAGCCAAGC CACTCACTC | 46 | CAGCTGTCACAC CCAGAGC | 103 |
| SIAH2 | seven in absentia homolog 2 (Drosophila) | CTCGGCAGTCC TGTTTC | 47 | CGTATGGTGCAG GGTCA | 104 |
| TCF2 | transcription factor 2, hepatic; LF-B3; variant hepatic nuclear factor | ACACCTGGTAC GTCAGAA | 48 | TCTGGACTGTCT GGTTGAAT | 105 |

TABLE 1-continued

Classification, Housekeeping Genes, Corresponding Primer Sets, and Relative Expression Levels

| | | | | | |
|---|---|---|---|---|---|
| TCP1 | t-complex 1 | ATGCCCAAGAG AATCGTAAA | 49 | CCTGTACACCAA GCTTCAT | 106 |
| TTF1 | thyroid transcription factor 1 | ATGAGTCCAAA GCACACGA | 50 | CCATGCCCACTT TCTTGTA | 107 |
| TRIM29 | tripartite motif-containing 29 | TGAGATTGAGG ATGAAGCTGAG | 51 | CATTGGTGGTGA AGCTCTTG | 108 |
| TUBA1 | tubulin, alpha 1 | CCGACTCAACG TGAGAC | 52 | CGTGGACTGAGA TGCATT | 109 |

Housekeeper gene list

| | | | | | |
|---|---|---|---|---|---|
| CFL1 | cofilin 1 (non-muscle) | GTGCCCTCTCC TTTTCG | 53 | TTCATGTCGTTG AACACCTTG | 110 |
| EEF1A1 | eukaryotic translation elongation factor 1 alpha 1 | CGTTCTTTTTC GCAACGG | 54 | CATTTTGGCTTT TAGGGGTAG | 111 |
| RPL10 | ribosomal protein L10 | GGTGTGCCACT GAAGAT | 55 | GGCAGAAGCGAG ACTTT | 112 |
| RPL28 | ribosomal protein L28 | GTGTCGTGGTG GTCATT | 56 | GCACATAGGAGG TGGCA | 113 |
| RPL37A | ribosomal protein L37a | GCATGAAGACA GTGGCT | 57 | GCGGACTTTACC GTGAC | 114 |

SCC subtype genes

| Gene Symbol | Gene Name | "Group Identified" and Level of Expression |
|---|---|---|
| CYP4F11 | cytochrome P450, family 4, subfamily F, polypeptide 11 | "Keratin"- High |
| UPK1B | uroplakin 1B | "Keratin"- High |
| NRXN3 | neurexin 3 | "Keratin"- High |
| RHCG | Rh family, C glycoprotein | "Keratin"- High |
| PADI3 | peptidyl arginine deiminase, type III | "Keratin"- High |
| IL32 | interleukin 32 | "Keratin"- High |
| PRRX2 | paired related homeobox 2 | "Keratin"- High |
| RAB6B | RAB6B, member RAS oncogene family | "Keratin"- High |
| CALB1 | calbindin 1, 28kDa | "Keratin"- High |
| G6PD | glucose-6-phosphate dehydrogenase | "Keratin"- High |
| PITX1 | paired-like homeodomain 1 | "Keratin"- Low |
| SERPINB5 | serpin peptidase inhibitor, clade B (ovalbumin), member 5 | "Keratin"- Low |
| KRT6B | keratin 6B | "Keratin"- Low |
| KRT17 | keratin 17 | "Keratin"- Low |
| DSG3 | desmoglein 3 (pemphigus vulgaris antigen) | "Keratin"- Low |
| TRIM29 | tripartite motif-containing 29 | "Keratin"- Low |
| CALML3 | calmodulin-like 3 | "Keratin"- Low |
| PTPRZ1 | protein tyrosine phosphatase, receptor-type, Z polypeptide 1 | "Keratin"- Low |
| KRT19 | keratin 19 | "Keratin"- Low |

TABLE 1-continued

Classification, Housekeeping Genes, Corresponding Primer Sets, and Relative Expression Levels

| Gene | Description | Classification |
|---|---|---|
| CD3G | CD3g molecule, gamma (CD3-TCR complex) | "Keratin"- Low |
| S100A2 | S100 calcium binding protein A2 | "RAS-High"- High |
| KRT17 | keratin 17 | "RAS-High"- High |
| RAB6B | RAB6B, member RAS oncogene family | "RAS-High"- High |
| CYP4F11 | cytochrome P450, family 4, subfamily F, polypeptide 11 | "RAS-High"- High |
| SYT17 | synaptotagmin XVII | "RAS-High"- High |
| KRT19 | keratin 19 | "RAS-High"- High |
| CCL19 | chemokine (C-C motif) ligand 19 | "RAS-High"- High |
| MS4A4A | membrane-spanning 4-domains, subfamily A, member 4 | "RAS-High"- High |
| TRIM29 | tripartite motif-containing 29 | "RAS-High"- High |
| FXYD3 | FXYD domain containing ion transport regulator 3 | "RAS-High"- High |
| PADI3 | peptidyl arginine deiminase, type III | "RAS-High"- Low |
| CXCL6 | chemokine (C-X-C motif) ligand 6 (granulocyte chemotactic protein 2) | "RAS-High"- Low |
| UPK1B | uroplakin 1B | "RAS-High"- Low |
| SLC6A15 | solute carrier family 6, member 15 | "RAS-High"- Low |
| PLAT | plasminogen activator, tissue | "RAS-High"- Low |
| MMP10 | matrix metallopeptidase 10 (stromelysin 2) | "RAS-High"- Low |
| TTC9 | tetratricopeptide repeat domain 9 | "RAS-High"- Low |
| CXCL1 | chemokine (C-X-C motif) ligand 1 (melanoma growth stimulating activity, alpha) | "RAS-High"- Low |
| LAMC2 | laminin, gamma 2 | "RAS-High"- Low |
| MMP13 | matrix metallopeptidase 13 (collagenase 3) | "RAS-High"- Low |
| MUC16 | mucin 16, cell surface associated | "Mucin-High"- High |
| TTC9 | tetratricopeptide repeat domain 9 | "Mucin-High"- High |
| CD3G | CD3g molecule, gamma (CD3-TCR complex) | "Mucin-High"- High |
| PITX1 | paired-like homeodomain 1 | "Mucin-High"- High |
| PTPRZ1 | protein tyrosine phosphatase, receptor-type, Z polypeptide 1 | "Mucin-High"- High |
| CLCA2 | chloride channel. calcium activated, family member 2 | "Mucin-High"- High |
| PLAU | plasminogen activator, urokinase | "Mucin-High"- High |
| ICAM1 | intercellular adhesion molecule 1 (CD54), human rhinovirus receptor | "Mucin-High"- High |
| ABCC6 | ATP-binding cassette, sub-family C (CFTR/MRP), member 6 | "Mucin-High"- High |
| WISP2 | WNT1 inducible signaling pathway protein 2 | "Mucin-High"- High |
| CYP4F11 | cytochrome P450, family 4, subfamily F, polypeptide 11 | "Mucin-High"- Low |
| RAB6B | RAB6B, member RAS oncogene family | "Mucin-High"- Low |

TABLE 1-continued

Classification, Housekeeping Genes, Corresponding
Primer Sets, and Relative Expression Levels

| | | |
|---|---|---|
| IL32 | interleukin 32 | "Mucin-High"- Low |
| CALB1 | calbindin 1, 28 kDa | "Mucin-High"- Low |
| ODC1 | ornithine decarboxylase 1 | "Mucin-High"- Low |
| ADAM23 | ADAM metallopeptidase domain 23 | "Mucin-High"- Low |
| NRXN3 | neurexin 3 | "Mucin-High"- Low |
| PRKX | protein kinase, X-linked | "Mucin-High"- Low |
| MYO1F | myosin 1F | "Mucin-High"- Low |
| NINJ2 | ninjurin 2 | "Mucin-High"- Low |

Lung Cancer Gene List excluding Squamous Cell subtypes

| GENE SYMBOL | GENE NAME | "Distinguisher" and Level of Expression |
|---|---|---|
| SFN | stratifin | "CARC vs ALL"- down |
| LGALS3 | lectin, galactoside-binding, soluble, 3 (galectin 3) | "CARC vs ALL"- down |
| CAPG | capping protein (actin filament), gelsolin-like | "CARC vs ALL"- down |
| CHGA | chromogranin A (parathyroid secretory protein 1) | "CARC vs ALL"- up |
| MAPRE3 | microtubule-associated protein, RP/EB family, member 3 | "CARC vs ALL"- up |
| SNAP91 | synaptosomal-associated protein, 91 kDa homolog (mouse) | "CARC vs ALL"- up |
| PSMD14 | proteasome (prosome, macropain) 26 S subunit, non-ATPase, 14 | "FOUR"- down |
| CBX1 | chromobox homolog 1 (HP1 beta homolog Drosophila) | "FOUR"- down |
| NFIL3 | nuclear factor, interleukin 3 regulated | "FOUR"- down |
| SCD5 | stearoyl-CoA desaturase 5 | "FOUR"- up |
| HOXD1 | homeobox D1 | "FOUR"- up |
| ICAM5 | intercellular adhesion molecule 5, telencephalin | "FOUR"- up |
| FOXH1 | forkhead box H1 | "FOUR"- down |
| CACNB1 | calcium channel, voltage-dependent, beta 1 subunit | "FOUR"- down |
| TCF2 | transcription factor 2, hepatic | "FOUR"- down |
| TCP1 | t-complex 1 | "FOUR"- up |
| FEN1 | flap structure-specific endonuclease 1 | "FOUR"- up |
| TUBA1 | tubulin, alpha 1 (testis specific) | "FOUR"- up |
| CYB5B | cytochrome b5 type B (outer mitochondrial membrane) | "FOUR"- down |
| PIK3C2A | phosphoinositide-3-kinase, class 2, alpha polypeptide | "FOUR"- down |
| ANTXR1 | anthrax toxin receptor 1 | "FOUR"- down |
| LIPE | lipase, hormone-sensitive | "FOUR"- up |
| MYBPH | myosin binding protein H | "FOUR"- up |

TABLE 1-continued

Classification, Housekeeping Genes, Corresponding
Primer Sets, and Relative Expression Levels

| | | |
|---|---|---|
| DOK1 | docking protein 1, 62 kDa (downstream of tyrosine kinase 1) | "FOUR"- up |
| SIAH2 | seven in absentia homolog 2 (Drosophila) | "FOUR"- down |
| ITGA6 | integrin, alpha 6 | "FOUR"- down |
| ICA1 | islet cell autoantigen 1, 69 kDa | "FOUR"- up |
| TITF1 | thyroid transcription factor 1 | "FOUR"- up |
| HPN | hepsin (transmembrane protease, serine 1) | "FOUR"- up |
| TRIM29 | tripartite motif-containing 29 | "FOUR"- down |
| DSC3 | desmocollin 3 | "FOUR"- down |
| BMP7 | bone morphogenetic protein 7 (osteogenic protein 1) | "FOUR"- down |
| MGRN1 | mahogunin, ring finger 1 | "FOUR"- up |
| HYAL2 | hyaluronoglucosaminidase 2 | "FOUR"- up |
| MYO7A | myosin VIIA | "FOUR"- up |
| ABCC5 | ATP-binding cassette, sub-family C (CFTR/MRP), member 5 | "FOUR"- down |
| GJB5 | gap junction protein, beta 5 (connexin 31.1) | "FOUR"- down |
| PLEKHA6 | pleckstrin homology domain containing, family A member 6 | "FOUR"- up |
| ME3 | malic enzyme 3, NADP(+)- dependent, mitochondrial | "FOUR"- up |
| ALDH3B1 | aldehyde dehydrogenase 3 family, member B1 | "FOUR"- up |
| RPL10 | ribosomal protein L10 | "HK"- NA |
| RPL28 | ribosomal protein L28 | "HK"- NA |
| RNU3IP2 | RNA, U3 small nucleolar interacting protein 2 | "HK"- NA |
| RPL37A | ribosomal protein L37a | "HK"- NA |
| CFL1 | cofilin 1 (non-muscle) | "HK"- NA |
| MED6 | mediator of RNA polymerase II transcription, subunit 6 homolog (yeast) | "HK"- NA |
| ST5 | suppression of tumorigenicity 5 | "HK"- NA |
| EEF1A1 | eukaryotic translation elongation factor 1 alpha 1 | "HK"- NA |
| CIB1 | calcium and integrin binding 1 (calmyrin) | "SCLC vs ALL"- down |
| LRP10 | low density lipoprotein receptor-related protein 10 | "SCLC vs ALL"- down |
| ACVR1 | activin A receptor, type 1 | "SCLC vs ALL"- down |
| STMN1 | stathmin 1/oncoprotein 18 | "SCLC vs ALL"- up |
| INSM1 | insulinoma-associated 1 | "SCLC vs ALL"- up |
| CDKN2C | cyclin-dependent kinase inhibitor 2C (p18, inhibits CDK4) | "SCLC vs ALL"- up |
| PAK1 | p21/Cdc42/Rac1- activated kinase 1 (STE20 homolog, yeast) | "TUMOR vs NML"- down |

TABLE 1-continued

Classification, Housekeeping Genes, Corresponding
Primer Sets, and Relative Expression Levels

| | | |
|---|---|---|
| TFAP2A | transcription factor AP-2 alpha (activating enhancer binding protein 2 alpha) | "TUMOR vs NML"- down |
| PAICS | phosphoribosylaminoimidazole carboxylase, phosphoribosylaminoimidazole succinocarboxamide synthetase | "TUMOR vs NML"- down |
| CLEC3B | C-type lectin domain family 3, member B | "TUMOR vs NML"- up |
| CDH5 | cadherin 5, type 2, VE-cadherin (vascular epithelium) | "TUMOR vs NML"- up |
| PECAM1 | platelet/endothelial cell adhesion molecule (CD31 antigen) | "TUMOR vs NML"- up |

HK = Housekeeping
SCLC = Small cell lung carcinoma distinguishers
NML = normal distinguishers
CARC = Carcinoid distinguishers
FOUR = AC/SCC subtype distinguishers It is recognized that additional genes/proteins can be used in the practice of the invention. For example, vimentin, a member of the intermediate filament family of proteins can be used to identify the adenocarcinoma subtype magnoid, and SMA can be used to identify squamoid subtype. In general, genes useful in classifying various classes, subclasses, and grades of lung cancer include those that are independently capable of distinguishing between normal versus tumor, or between different classes or grades of lung cancer. A gene is considered to be capable of reliably distinguishing between classes if the area under the receiver operator characteristic (ROC) curve is approximately 1.

A gene capable of reliable classification (herein referred to as a "discriminating gene") may be one that is upregulated (e.g., expression is increased) or downregulated (e.g., expression is decreased) relative to the control. The expression values of genes that are upregulated in a particular class or grade of lung cancer can be pooled into one gene cassette, and the expression values of genes that are downregulated in a particular class or grade of lung cancer can be pooled into a separate gene cassette. The overall expression level in each gene cassette is referred to herein as the "expression profile" and is used to classify a test sample according to class, subclass, or grade of lung cancer. However, it is understood that independent evaluation of expression for each of the genes disclosed herein can be used to classify tumor types without the need to group upregulated and downregulated genes into one or more gene cassettes.

In one embodiment, genes useful in classifying different types and subtypes of lung cancer are set forth in Table 1. It is understood that the expression level of any gene that is capable of reliable classification of different subtypes can be utilized in the methods described herein.

Measurement of Gene Expression

In one embodiment, the expression profile can comprise values representing the measurement of the transcriptional state. The transcriptional state of a sample includes the identities and relative abundance of the RNA species encoded by the discriminative genes disclosed herein. The transcriptional state can be conveniently determined by measuring transcript presence or absence by any of several existing gene expression technologies such as reverse transcription-polymerase chain reaction (RT-PCR), particularly quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art.

This PCR-based analysis is suitable for use on paraffin embedded tissues. Such tissues can be analyzed by molecular diagnosis of lung cancer by gene expression. The method comprises a novel and high-throughput approach to independently validate the genes. The method utilizes a robust novel self-normalizing method of classification which allows for a modular predictor. In the methods of the invention predictions are made in two ways, using a one versus all and all pairwise approach such that many classes can be predicted using small gene cassettes. Since each of the gene cassettes is independent, new cassettes can be added to the existing predictor without changing the overall method of prediction. This allows for the addition of new classes as needed. For example, the current predictor distinguishes a total of 9 classes and subclasses of lung cancer. As new groups of lung cancer are described or as new features of tumor behavior are identified, these can be added to the current predictor as cassettes without changing the existing structure of the classifier.

Gene selection for gene cassettes that are indicative of lung cancer subtypes is performed in the following manner. A set of gene expression cohorts are selected from among all published reports of lung cancers assayed by gene expression data due to their relatively large size and inclusion of a representative spectrum of tumor variants. Expression datasets are transformed using genomic meta-analysis methods that have been previously reported. Briefly, all arrays are evaluated for the quality of the scanned image. Probes are mapped to genes using Unigene identifiers. In cases where multiple probes map to the same Unigene identifier, these are averaged. Genes are evaluated for cross-platform reliability using integrative correlations. Genes with integrative correlations twice that observed by random chance are considered reliable and retained across datasets. Reliable genes are then ranked for each gene for its ability to distinguish each of the morphologic variants in both the 1 versus all (i.e., tumor versus normal) and the all-pairwise (i.e., normal versus small cell carcinoma) case. The statistic used for the ranking is the area under the receiver operator characteristic (ROC) curve (a plot of sensitivity versus (1-specificity)). Although genes are evaluated for reliability across datasets, the independent sample sets are not combined for the purposes of the ROC ranking. As a result, multiple independent analyses are performed and multiple independent rankings are obtained for each gene's ability to distinguish groups of interest. A gene is considered reliable if its area under the ROC curve is close to 1 for each of the independent datasets. In cases where a gene's ROC is close to 1 in some but not all datasets, the genes overall reliability is considered as measured by integrative correlations. In one embodiment, the genes are limited to approximately 100 genes. See example 4 for more details.

Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real-time fluorescence measurement capabilities, for example, SMARTCYCLER® (Cepheid, Sunnyvale, Calif.), ABI PRISM 7700® (Applied Biosystems, Foster City, Calif.), ROTOR-GENET™ (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.).

Quantitative RT-PCR (qRT-PCR) (also referred as real-time RT-PCR) is preferred under some circumstances because it provides not only a quantitative measurement, but also reduced time and contamination. As used herein, "quantitative PCR (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A labeled probe can be used to detect the extension product generated by PCR amplification. Any probe format utilizing a labeled probe comprising the sequences of the invention may be used, e.g., such as SCORPIONS™ probes, sunrise probes, TAQMAN® probes, or molecular beacon probes as is known in the art or described elsewhere herein.

Methods for setting up a PCR reaction are well known to those skilled in the art. The reaction mixture minimally comprises template nucleic acid (except in the case of a negative control as described below) and oligonucleotide primers and/or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template until synthesis terminates. An appropriate concentration includes one which catalyzes this reaction in the presently described methods. Known DNA polymerases include, for example, E. coli DNA polymerase I, T7 DNA polymerase, Thermus thermophilus (Tth) DNA polymerase, Bacillus stearothermophilus DNA polymerase, Thermococcus litoralis DNA polymerase, Thermus aquaticus (Taq) DNA polymerase and Pyrococcus furiosus (Pfu) DNA polymerase.

Usually the reaction mixture will further comprise four different types of dNTPs corresponding to the four-naturally occurring nucleoside bases, i.e., dATP, dTTP, dCTP and dGTP. In the subject methods, each dNTP will typically be present in an amount ranging from about 10 to 5000 µM, usually from about 20 to 1000 µM, about 100 to 800 µM, or about 300 to 600 µM.

The reaction mixture prepared in the first step of the subject methods further includes an aqueous buffer medium that includes a source of monovalent ions, a source of divalent cations, and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc and the like, where the cation will typically be magnesium. Any convenient source of magnesium cation may be employed, including magnesium chloride, magnesium acetate, and the like. The amount of magnesium present in the buffer may range from 0.5 to 10 mM, but will preferably range from about 1 to about 6 mM, or about 3 to about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA and the like.

In preparing the reaction mixture, the various constituent components may be combined in any convenient order. For example, the buffer may be combined with primer, polymerase and then template nucleic acid, or all of the various constituent components may be combined at the same time to produce the reaction mixture.

Alternatively, commercially available premixed reagents can be utilized in the methods of the invention according to the manufacturer's instructions, or modified to improve reaction conditions (e.g., modification of buffer concentration, cation concentration, or dNTP concentration, as necessary), including, for example, TAQMAN® Universal PCR Master Mix (Applied Biosystems), OMNIMIX® or SMARTMIX® (Cepheid), IQ™ Supermix (Bio-Rad Laboratories), LIGHTCYCLER® FastStart (Roche Applied Science, Indianapolis, Ind.), or BRILLIANT® qRT-PCR Master Mix (Stratagene, La Jolla, Calif.).

Following preparation of the reaction mixture, the reaction mixture is subjected to primer extension reaction conditions ("conditions sufficient to provide polymerase-based nucleic acid amplification products"), i.e., conditions that permit for polymerase mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98° C. and more usually from about 93 to 96° C., for a period of time ranging from about 3 to 120 sec, usually from about 5 to 30 sec.

Following denaturation, the reaction mixture will be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. The temperature to which the reaction mixture is lowered to achieve these conditions will usually be chosen to provide optimal efficiency and specificity, and will generally range from about 50 to 75, usually from about 55 to 70 and more usually from about 60 to 68° C., more particularly around 62° C. Annealing conditions will be maintained for a period of time ranging from about 15 sec to 30 min, usually from about 20 sec to 5 min, or about 30 sec to 1 minute, or about 43 seconds.

This step can optionally comprise one of each of an annealing step and an extension step with variation and optimization of the temperature and length of time for each step. In a 2-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described elsewhere herein as well as in U.S. Pat. Nos. 5,612,473; 5,602,756; 5,538,871; and 5,475,610, the disclosures of which are herein incorporated by reference.

The methods of the invention can also be used in non-PCR based applications to detect a target nucleic acid sequence, where such target that may be immobilized on a solid support. Methods of immobilizing a nucleic acid sequence on a solid support are known in the art and are described in Ausubel et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenune, and for other supports useful according to the invention, CPG, Inc.

The person skilled in the art of nucleic acid amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al, 1993. Diagnostic Molecular Microbiology: Principles and Applications, American Society for Microbiology, Washington, D.C.). The scope of this invention is not limited to the use of amplification by PCR, but rather includes the use of any rapid nucleic acid amplification methods or any other procedures which may be useful with the sequences of the invention for the detection and/or quantification of expression of one or more of the discriminative genes disclosed herein.

Further, variations on the exact amounts of the various reagents and on the conditions for the PCR or other suitable amplification procedure (e.g., buffer conditions, cycling times, etc.) that lead to similar amplification or detection/quantification results are known to those of skill in the art and are considered to be equivalents. In one embodiment, the subject qRT-PCR detection has a sensitivity of detecting fewer than 50 copies (preferably fewer than 25 copies, more preferably fewer than 15 copies, still more preferably fewer than 10 copies) of target nucleic acid (e.g., genomic or cDNA) in a sample. In one embodiment, a hot-start PCR reaction is performed (e.g., using a hot start Taq DNA polymerase) so as to improve PCR reaction by decreasing background from non-specific amplification and to increase amplification of the desired extension product.

Evaluation of Protein Expression

In one embodiment, lung cancer status is evaluated using levels of protein expression of one or more of the discriminative genes listed in Table 1. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In one embodiment, antibodies specific for biomarker proteins are utilized to detect the expression of a biomarker protein in a body sample. The method comprises obtaining a body sample from a patient, contacting the body sample with at least one antibody directed to a biomarker that is selectively expressed in lung cancer cells, and detecting antibody binding to determine if the biomarker is expressed in the patient sample. A preferred aspect of the present invention provides an immunocytochemistry technique for diagnosing lung cancer subtypes. One of skill in the art will recognize that the immunocytochemistry method described herein below may be performed manually or in an automated fashion.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Polyclonal antibodies can be prepared by immunizing a suitable subject (e.g., rabbit, goat, mouse, or other mammal) with a biomarker protein immunogen. The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550-52; Kenneth (1980) in *Monoclonal Antibodies: A New Dimension In Biological Analyses* (Plenum Publishing Corp., NY); and Lerner (1981) *Yale J. Biol. Med.,* 54:387-402).

Alternative to preparing monoclonal antibody-secreting hybridomas, a monoclonal antibody can be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene *SurfZAP ∂ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J.* 12:725-734.

Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. In one method, antibody binding can be detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include horseradish peroxidase (HRP) and alkaline phosphatase (AP). Samples may be reviewed via automated microscopy or by personnel with the assistance of computer software that facilitates the identification of positive staining cells.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

In regard to detection of antibody staining in the immunocytochemistry methods of the invention, there also exist in the art, video-microscopy and software methods for the quantitative determination of an amount of multiple molecular species (e.g., biomarker proteins) in a biological sample wherein each molecular species present is indicated by a representative dye marker having a specific color. Such methods are also known in the art as a colorimetric analysis methods. In these methods, video-microscopy is used to provide an image of the biological sample after it has been stained to visually indicate the presence of a particular biomarker of interest. Some of these methods, such as those disclosed in U.S. patent application Ser. No. 09/957,446 to Marcelpoil et al. and U.S. patent application Ser. No. 10/057,729 to Marcelpoil et al., incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the biomarker proteins of interest. Methods for making antibodies and for selecting appropriate antibodies are known in the art. See, for example, Celis, ed. (in press) *Cell Biology & Laboratory Handbook,* 3rd edition (Academic Press, New York), which is herein incorporated in its entirety by reference. In some embodiments, commercial antibodies directed to specific biomarker proteins may be used to practice the invention.

Furthermore, one of skill in the art will recognize that the concentration of a particular antibody used to practice the methods of the invention will vary depending on such factors as time for binding, level of specificity of the antibody for the biomarker protein, and method of body sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

Monoclonal and polyclonal antibodies available in the art can be used in the practice of the invention. In particular, antibodies against any of the biomarkers in Table 1 can be used in the practice of the invention. Monoclonal and polyclonal antibodies have been developed against peptide hormones (ACTH, GGRP, chromogranin A, serotonin, etc), specific enzymes (NSE, CK-BB, chromogranin A), cell adhesion molecules (NCAM), altered sugar chains (mucin), and markers of proliferation (ki-67, PCNA). Many of these antibodies can be used to identify the different types of normal cells populating the respiratory tract based on their function. For instance, the distinction between SCLC and NSCLC can be defined relatively well with neuroendocrine markers, such as neuron-specific enolase (NSE), neural cell adhesion molecule (NCAM), and peptide hormones. Approximately 80% of SCLC will show a neuroendocrine feature, but these markers are not specific since they are also exhibited by carcinoid tumors and a small percent of adenocarcinomas. Carcinoid tumors are believed to arise from Kulchitsky's cells, which also have an endocrine function. Another example of exploiting the specialized functions of cells to diagnose lung tumors is in the use of antibodies against surfactant apoprotein. This antibody reacts with type II alveolar cells and with non-mucinous BAC, potentially due to a common progenitor. In contrast to using markers of neuronal differentiation to diagnose neuroendocrine tumors, surfactant apoprotein is specific for lung adenocarcinoma but has poor sensitivity with only 50% of adenocarcinomas staining positive. In some embodiments, surfactant expressing adenocarcinomas are a definable entity by genomics and this group has a distinct prognosis separate from other adenocarcinomas. In addition to standard molecular techniques in clinical pathology, tremendous effort has been devoted to the development of novel biomarkers to improve lung cancer diagnostics. Compared to other malignancies, particularly lymphoma and leukemia, little of this work has born fruit in terms of clinically useful tests. While numerous authors have documented that markers of poor prognosis can be reliably identified, these do not appear to have garnered much clinical interest (Gordon et al. (2003) Cancer Epidemiol Biomarkers Prev 12(9):905-10). Finally, markers associated with specific outcomes such as site-specific metastasis and response to treatment (with the exception of EGFR) have been too preliminary to be medically actionable.

Subjects

Lung cancer status can be assessed using the biomarker proteins described herein in human as well as in non-human subjects (e.g., non-human animals, such as laboratory animals, e.g., mice, rats, guinea pigs, rabbits; domesticated livestock, e.g., cows, horses, goats, sheep, chicken, etc.; and companion animals, e.g., dogs, cats, etc.). Suitable controls are usually selected on the basis of the subject under study, and the nature of the study (e.g., type of sample, type of spectra, etc.). Usually, controls are selected to represent the state of "normality." As described herein, deviations from normality (e.g., higher than normal, lower than normal) in test data, test samples, test subjects, etc. are used in classification, diagnosis, etc.

For example, in most cases, control subjects are the same species as the test subject and are chosen to be representative of the equivalent normal (e.g., healthy) subject. A control population is a population of control subjects. If appropriate, control subjects may have characteristics in common (e.g., sex, ethnicity, age group, etc.) with the test subject. If appropriate, control subjects may have characteristics (e.g., age group, etc.) which differ from those of the test subject. For example, it may be desirable to choose healthy 20-year olds of the same sex and ethnicity as the study subject as control subjects.

In most cases, control samples are taken from control subjects. Usually, control samples are of the same sample type (e.g., fresh biopsy, paraffin embedded tissue, cryogenically preserved tissue, etc.), and are collected and handled under the same or similar conditions as the sample under study. Likewise, control data (e.g., control values) are usually obtained from control samples which are taken from control subjects. Usually, control data are of the same type and are collected and handled (e.g., recorded, processed) under the same or similar conditions as the test data.

A control sample for use in the invention may be derived from non-malignant cells or tissue (including "normal" cells or tissue, or cells or tissue displaying benign lesions), or may be derived from cells or tissue displaying a different type or grade of lung cancer as the test sample.

Class Prediction

The present invention provides a method for classifying lung cancer classes and subclasses using gene expression analysis. In one embodiment, the method utilizes a classifier mechanism in which the expression profiles of each group (e.g., one versus all, such as tumor vs. normal, or each pairwise, such as normal vs. small cell, or small cell vs. non-small cell, etc.) are self-normalized. For each one versus all and each pairwise classification, the gene cassette includes genes which are expressed at high levels relative to the alternative class and low levels relative to the alternative class. It is the ratio of each that is then used to make the class distinction, as well as the gene expression values themselves.

The data obtained from the expression profiles, and optionally from demographic information, can be evaluated using one or more pattern recognition algorithms. In one embodiment, the expression of a plurality of genes listed in Table 1 is used to classify tumor types, subtypes, and class. It is to be understood that other genes and/or diagnostic criteria may be used in this invention. For example, the results of imaging tests or histological evaluation may optionally be combined with expression profiles generated using the genes disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Kowalski et al., 1986). The robustness of the predictive models can also be checked using cross-validation, by leaving out selected samples from the analysis.

Examples of supervised pattern recognition methods include the following: nearest centroid methods (Dabney (2005) *Bioinformatics* 21(22):4148-4154 and Tibshirani et al. (2002) *Proc. Natl. Acad. Sci USA* 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear descriminant analysis (LDA) (see, for example, Nillson, 1965); K-nearest neighbour analysis (KNN) (see, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, which is herein incorporated by reference in its entirety for its teachings regarding tumor classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centred and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the Internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker protein. Alternately, a separate device (e.g., a digital computer) may be used to compare the measured value(s) and the reference value(s). Automated devices for comparison may include stored reference values for the biomarker protein(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

FFPE

In one aspect of the invention, the analysis is performed on lung biopsies that are embedded in paraffin wax. This aspect of the invention provides a means to improve current diagnostics by accurately identifying the major histological types, even from small biopsies. The methods of the invention, including the RT-PCR methods, are sensitive, precise and have multianalyte capability for use with paraffin embedded samples. See, for example, Cronin et al. (2004) *Am. J Pathol.* 164(1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) *J Histochem Cytochem* 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein—nucleic acid and protein—protein crosslinks in vitro (Clark et al. (1986) *J Histochem Cytochem* 34:1509-1512; McGhee and von Hippel (1975) *Biochemistry* 14:1281-1296).

The ability to analyze gene expression patterns in these archived tissues would greatly facilitate retrospective studies to correlate gene expression patterns with given disease states, or histological and clinical phenotypes. This approach could be used to discover biomarkers for therapeutic decision making and also to develop clinical tests, as FFPE sample collection and storage is a routine practice in pathology laboratories.

Methods are known in the art for the isolation of RNA from FFPE tissue. In one embodiment, total RNA can be isolated from FFPE tissues as described by Bibikova et al. (2004) *American Journal of Pathology* 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

Kits

Kits for practicing the methods of the invention are further provided. By "kit" is intended any manufacture (e.g., a package or a container) comprising at least one reagent, e.g., an antibody, a nucleic acid probe or primer, etc., for specifically detecting the expression of a biomarker of the invention. The kit may be promoted, distributed, or sold as a unit for performing the methods of the present invention. Additionally, the kits may contain a package insert describing the kit and methods for its use.

In one embodiment, kits for practicing the methods of the invention are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the invention. The kits may comprise at least 2, at least 3, at least 4, at least 5, at least 6, at least 7, at least 8, at least 9, at least 10, or more antibodies for use in the methods of the invention.

The following examples are offered by way of illustration and not by way of limitation.

EXPERIMENTAL

Example 1. Immunohistochemical Detection of Gene Expression Subsets of Non-Small Cell Carcinoma Background:

Messenger RNA abundance studies using nucleic acid microarrays allow cluster separation of morphologically similar diseases into molecular subsets. Outcome studies in breast carcinomas and diffuse large cell lymphomas show the relevance of this approach. More recently, lung adenocarcinomas have been subdivided at the mRNA cluster level into magnoid, squamoid, and bronchioid types (1). The purpose of this project was to pick single representative loci from each cluster, and to screen for distinct clustering at the protein level within an unselected set of non-small cell lung carcinoma (NSCLC).

Design:

Duplicate-core tissue microarrays were manufactured from 187 surgically resected primary NSCLC. Cases were unselected for morphology, stage, demographics, risk factors, or outcomes. Screening loci were selected using a rational approach based on gene expression profiling. Loci had to segregate the 3 reported adenocarcinoma subtypes (bronchioid, magnoid, and squamoid), and had to be commercially available. Smooth muscle actin, vimentin, and TTF-1 were chosen. Paraffin immunostains were scored by one Pathologist for signal strength and carcinoma percent positivity. Sample data were included if cores stained for at least one of the 3 markers in at least 10% of cells in at least one of 2 replicate stains. If neither replicate sample stained for any of the 3 markers, it was excluded.

Results:

152 of 187 samples were evaluable. 16 samples were excluded because the tumor or the core was absent, and 19 were excluded due to <10% cells staining for the marker. The staining patterns of the 152 samples are ordered by hierarchical agglomerative clustering, and show distinct clustering into three groups. The Chi square test p value for this distribution of staining is p<2.2e-16.

Conclusions:

This study shows that molecular subsets exist within unselected NSCLC, and that these distinguish distinct clusters similar to those seen with mRNA abundance analyses. The RNA and protein expression in NSCLC is useful to correlate with recognized morphologic subgroups, and with treatment response and survival.

The study identified:

1) Representative markers from the adenocarcinoma mRNA clusters to distinguish histologically diagnostic types of NSCLC at the protein level.

2) Representative markers from the adenocarcinoma mRNA clusters to screen for the 3 subtypes of adenocarcinoma at the protein level.

Methods

Tissue microarrays were made from duplicate 1 mm cores taken from 187 unselected UNC non-small cell lung carcinoma (NSCLC) resection specimens.

To select markers distinguishing reported tumor subtypes, the following approach was used. A list of all commercially available antibodies for which protocols are established was prepared (approximately 120). The gene targets of these antibodies were identified using data provided by the NCBI and Genbank. Existing gene expression data from the published record (1) were reviewed for those genes which distinguish established lung adenocarcinoma subtypes, and cross-referenced with the available antibody list. Approximately 50 genes with antibodies readily available were also statistically associated with one or more of the adenocarcinoma subtypes. Three were selected, one for each of the subtypes, accounting for experience with the antibodies to aid in those most likely to be useful. TTF-1 was chosen to represent the "bronchioid" cluster, and was detected with Ventana clone 867G34-1 after EDTA pH8 HIER. SMA was chosen to represent the "squamoid" cluster, and was detected with Ventana clone 1A4 after EDTA pH8 HIER. Vimentin was chosen to represent the "magnoid" cluster, and was detected with Ventana clone V9 after EDTA pH8 HIER. Stained sections were scored for average signal strength (0-3+) and percentage of tumor cells which were positive to any degree. Data from each of two cores were collated, and the % positivity data were averaged. Sample data were included if cores stained for at least one of the markers in >10% of the tumor cells.

Results

Of the 187 samples, 152 were evaluable. 16 samples were excluded because of mechanical core loss in the stained TMA section, and 19 samples were excluded because of <10% staining for each of the three markers. Of the 152 evaluable cases, 85 (56%) were adenocarcinoma, 53 (35%) were squamous carcinoma, and 14 (9%) were NSCLC, subtype not specified.

Immunoreactivities for each of the three proteins were clustered for the total set of 152 cases, and show three major clusters (FIG. 1). These clusters are distinct by chi-square analysis (p<2.2e-16).

Figure 2:
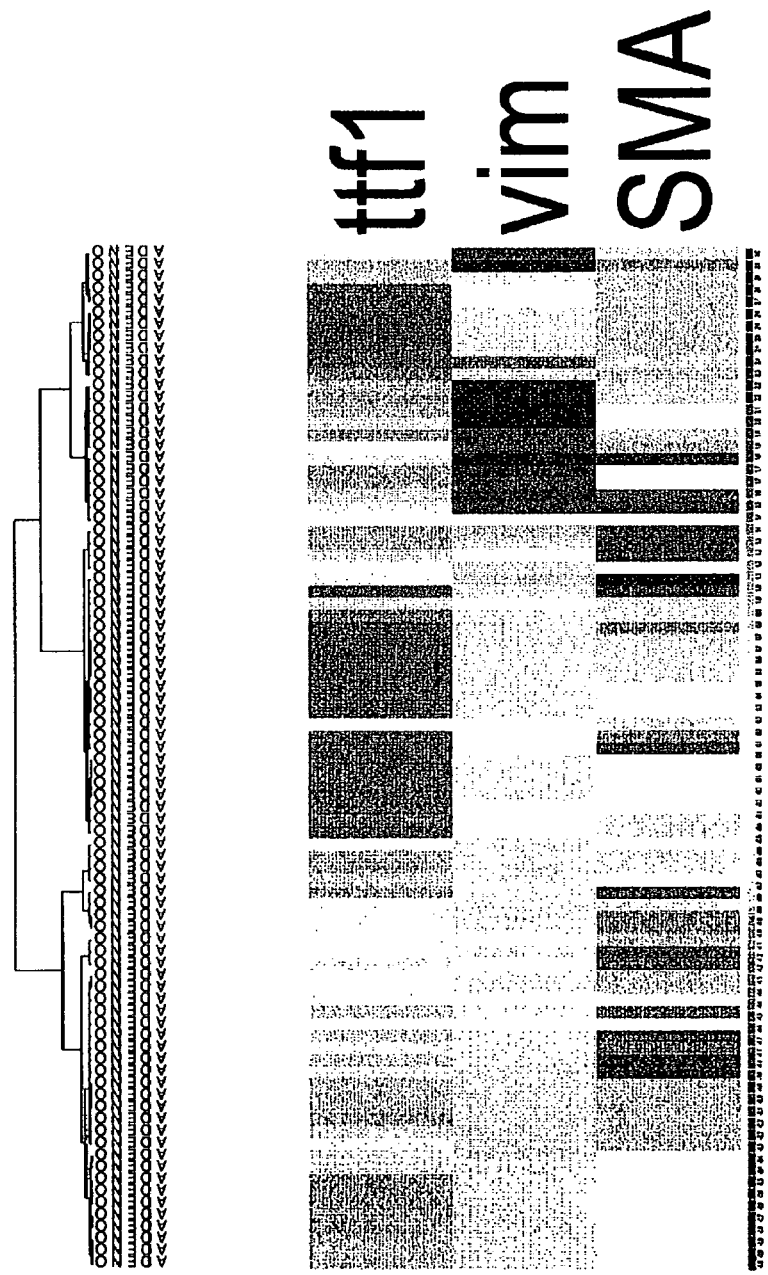
FIG. 2 shows protein clustering of the adenocarcinoma subset (n=85).

Immunoreactivities for each of the three proteins were clustered for the histologically diagnosed adenocarcinomas (n=85), and show three major clusters (FIG. 2).

Figure 3:
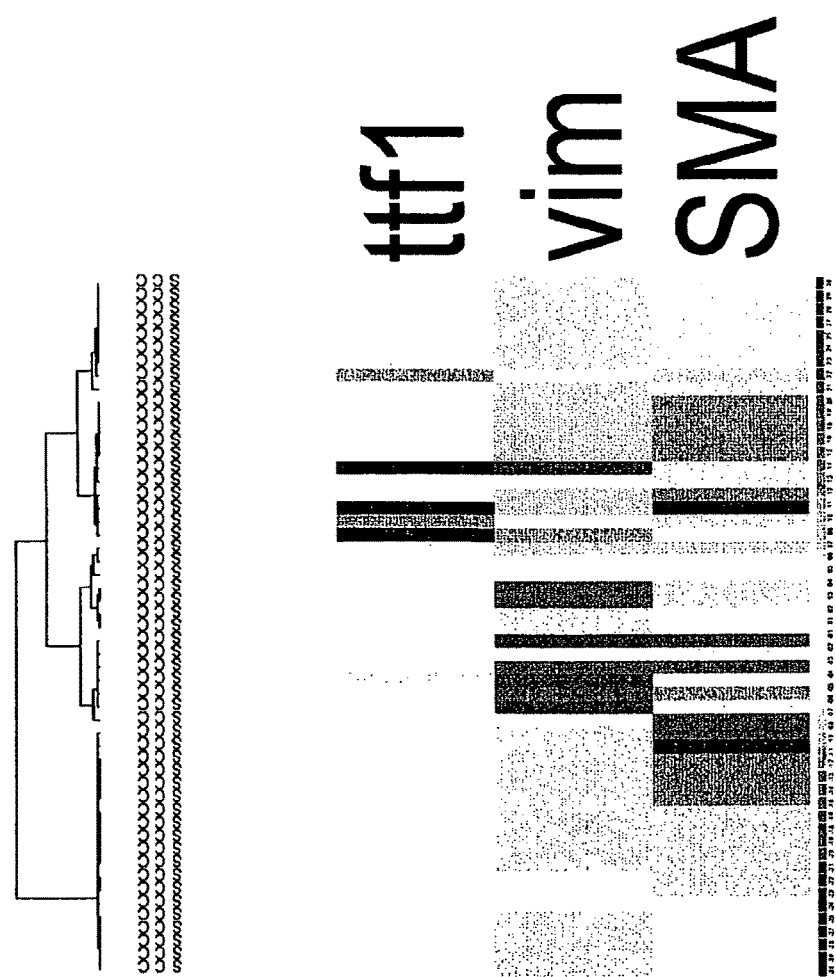
FIG. 3 shows protein clustering of the squamous carcinoma subset (n=53).

Immunoreactivities for each of the three proteins were clustered for the histologically diagnosed squamous carcinomas (n=53), and show three major clusters (FIG. 3).

In recent experiments (data not shown), there is good correlation between TTF-1 mRNA abundance and protein abundance.

Conclusions

1. The rational antibody selection process described here was successful at leveraging existing antibody resources for novel genomic analysis.
2. The first hypothesis of antibody selection clearly distinguished 3 groups of lung adenocarcinomas, as expected based on the genomic results.
3. The genomic analysis is useful for predicting the clinical outcomes of these adenocarcinoma subtypes.

REFERENCES

1. D N Hayes et al. Gene expression profiling reveals reproducible human lung adenocarcinoma subtypes in multiple independent patient cohorts. J Clin One 24:5079, 2006.
2. A Bhattacharjee et al. Classification of human lung carcinomas by mRNA expression profiling reveals distinct adenocarcinoma subclasses. PNAS 98:13790, 2001.
3. M E Garber et al. Diversity of gene expression in adenocacnoma of the lung. PNAS 98-13784, 2001.
4. D G Beer et al. Gene-expression profiles predict survival of patients with lung adenocarcinoma. Nat Med 8:816, 2002.
5. A C Borczuk, C A Powell. Expression profiling and lung cancer development. Proc Am Thor Soc 4:127, 2007.
6. T A D'Amico et al. A biologic risk model for stage 1 lung cancer: Immunohistochemical analysis of 408 patients with the use of ten molecular markers. J Thorac Cardiovasc Surg 117:736, 1999.

Example 2. Subtypes of Lung Adenocarcinoma Derived from Gene Expression Patterns are Recapitulated Using a Tissue Microarray System and Immunohistochemistry Background Messenger RNA abundance studies using nucleic acid microarrays allow cluster separation of morphologically similar diseases into molecular subsets. Outcome studies in breast carcinomas and diffuse large cell lymphomas show the relevance of this approach. In the field of lung cancer, multiple groups have shown that differences in mRNA abundance distinguish the morphologic variants, including squamous cell carcinoma, small cell carcinoma, and adenocarcinoma. More recently, lung adenocarcinomas have been subdivided at the mRNA cluster level into magnoid, squamoid, and bronchioid types using gene expression array-based technology (Hayes et al. J Clin One 24:5079, 2006). The goal was to translate these findings into more conventional paraffin-based diagnostic tests.

The purpose of this project was to pick single representative markers from each cluster, and to screen for distinct clustering at the protein level within a set of lung adenocarcinomas. The goal was to identify the three distinct mRNA clusters in a set of paraffin-embedded adenocarcinomas which would not otherwise be subdivided in routine clinical practice. The clinical phenotypes and survival outcomes of these molecular subtypes are also reported.

Finally, another goal was to expedite marker identification, using existing immunohistochemical reagents. It was determined that clinically useful subtypes of lung adenocarcinomas previously identified using gene expression can also be identified using immunohistochemistry (IHC) in clinically obtained paraffin specimens.

Methods

Duplicate-core tissue microarrays were manufactured from 187 surgically resected primary NSCLC. Only adenocarcinoma histology was considered for the current study. Cases were unselected for morphology, stage, demographics, risk factors, or outcomes. Screening markers were selected using a rational approach based on gene expression profiling and only commercially available reagents were considered using the following approach. A list of all commercially available antibodies for which protocols are established was prepared (approximately 120). The gene targets of these antibodies were identified using data provided by the NCBI and Genbank. Existing gene expression data from the published record was reviewed for those genes which distinguish established lung adenocarcinoma subtypes, and cross-referenced with the available antibody list.

Approximately 50 genes with antibodies readily available were also statistically associated with one or more of the adenocarcinoma subtypes. From the set of 50 likely candidates, 3 markers were selected (one for each of the subtypes—bronchioid, magnoid, and squamoid) based on the area under the receiver operator characteristic curve (ROC) (see Results). Experience with the antibodies was further considered to aid in those most likely to be useful. Thyroid transcription factor 1 (TTF-1) was chosen to represent the "bronchioid" cluster, and was detected with Ventana clone 867G34-1 after EDTA pH8 HIER. Smooth muscle actin (SMA) was chosen to represent the "squamoid" cluster, and was detected with Ventana clone 1A4 after EDTA pH8 HIER. Vimentin was chosen to represent the "magnoid" cluster, and was detected with Ventana clone V9 after EDTA pH8 HIER. Stained sections were scored for average signal strength (0-3+) and percentage of tumor cells which were positive to any degree. Data from each of two cores were collated, and the % positivity data were averaged. Sample data were included if cores stained for at least one of the markers in >10% of the tumor cells. If neither replicate sample stained for any of the 3 markers, it was excluded. The gene-protein concordance of the targets was evaluated in an unbiased manner using the integrative correlations method (IC). Clinical histories were abstracted from the medical record including staging, surgical treatment, survival, and site of relapse.

Results 152 of 187 samples were evaluable. 16 samples were excluded because the tumor or the core was absent, and 19 were excluded due to <10% cells staining for the marker. Of the 152 evaluable samples, 85 were adenocarcinoma. The staining patterns of the 85 samples are ordered by hierarchical agglomerative clustering, and show distinct clustering into three groups (FIG. 4). The Chi square test p value for this distribution of staining is p<2.2×10-16.

Approximately 125 antibodies were screened and associated with approximately 200 transcripts from the gene expression array repository. Of these, 35% were statistically significantly associated with at least one tumor subtype in keeping with previous reports. The following targets each demonstrated area under the ROC>0.9 for distinguishing adenocarcinoma subtypes and were selected for IHC confirmation in the clinical TMA system: vimentin—magnoid subtype; SMA—squamoid subtype; and TTF1—bronchioid subtype.

TABLE 2

Patient Characteristics by Molecular Subtype of Adenocarcinoma
The p value for the IC coefficient for each of these 3 markers was <0.001 suggesting that the IHC markers were reliable representations the gene expression. Importantly, staining positive for one marker was associated with negative staining for the others (chi squared p value <0.02).

|  | TTF1/ Bronchioid | Vimentin/ Magnoid | SMA/ Squamoid |
|---|---|---|---|
| N = 85 | 45(53%) | 13(15%) | 27(32%) |
| Smoking status |  |  |  |
| Current | 20 | 3 | 9 |
| Former | 19 | 10 | 9 |
| Never | 2 | 0 | 2 |
| Unknown | 4 | 0 | 7 |
| Gender |  |  |  |
| Male | 22 | 7 | 12 |
| Female | 23 | 6 | 15 |
| Race |  |  |  |
| African American | 14 | 4 | 1 |
| Caucasian | 30 | 9 | 26 |
| Grade |  |  |  |
| Unknown | 4 | 0 | 1 |
| Well | 5 | 1 | 5 |
| Well-Moderate | 4 | 0 | 2 |
| Moderate | 21 | 4 | 9 |
| Moderate-Poor | 9 | 1 | 2 |
| Poor | 5 | 5 | 7 |
| Bronchioalveolar Morphology | 3 | 2 | 0 |
| Clinical Stage |  |  |  |
| IA | 16 | 7 | 13 |
| IB | 11 | 4 | 6 |
| IIA | 0 | 0 | 1 |
| IIB | 5 | 0 | 2 |
| IIIA | 4 | 0 | 0 |

TABLE 2-continued

Patient Characteristics by Molecular Subtype of Adenocarcinoma
The p value for the IC coefficient for each of these 3 markers was <0.001 suggesting that the IHC markers were reliable representations the gene expression. Importantly, staining positive for one marker was associated with negative staining for the others (chi squared p value <0.02).

|  | TTF1/ Bronchioid | Vimentin/ Magnoid | SMA/ Squamoid |
|---|---|---|---|
| IIIB | 0 | 1 | 0 |
| UNK | 9 | 1 | 5 |
| Pathologic Stage |  |  |  |
| IA | 18 | 5 | 14 |
| IB | 5 | 2 | 4 |
| IIA | 3 | 1 | 0 |
| IIB | 8 | 1 | 6 |
| IIIA | 8 | 2 | 1 |
| IIIB | 0 | 1 | 0 |
| UNK | 3 | 1 | 2 |
| Site of 1st recurrence 26(31%) with metastasis in study period | 12(26%) | 5(38%) | 9(33%) |
| Bone | 3 | 0 | 0 |
| Brain | 3 | 3 | 4 |
| Lung | 6 | 2 | 4 |
| Node | 0 | 0 | 1 |

The clinical phenotype associated with the 3 molecular subtypes of lung adenocarcinoma reproduces previous work. Most notably, there are clear differences in the frequency and pattern of recurrence (Table 2) by tumor subtype and survival. FIG. 5 demonstrates the survival by tumor subtype.

Conclusions

1. The rational antibody selection process described here was successful at leveraging existing antibody resources for novel genomic analysis.
2. The first hypothesis of antibody selection clearly distinguished 3 groups of lung adenocarcinomas, as expected based on the genomic results.
3. Dramatic patterns of tumor behavior were observed that were associated with tumor subtypes potentially vital to patients and clinicians. These include differences in the frequency and pattern of relapse which may allow targeted interventions.

Example 3. Paraffin-Based Molecular Diagnosis of Lung Cancer Reproduces Morphologic and Molecular Subtypes of Lung Cancer Background Gene expression classifications of lung cancer by microarray have shown potential for guiding therapy (1-2). However, high-quality RNA from fresh tissue for microarray is generally unavailable in clinical practice. A real-time quantitative reverse transcription PCR (qRT-PCR) assay and analytic method for identifying morphological subtypes of lung cancer from clinically obtained formalin-fixed, paraffin-embedded (FFPE) tissues are introduced.

Methods

Approximately 700 DNA microarrays were analyzed to select genes distinguishing the major histological variants of NSCLC carcinoma and SCLC carcinoma. Previous work has shown that NSCLC is a molecularly diverse group, especially among adenocarcinomas (AC)(3). A 57-gene qRT-PCR assay (52 classifiers and 5 control genes) that molecularly identifies histological subtypes of lung cancer and molecular subtypes of adenocarcinoma (FIG. 6) was developed. This assay was used to profile RNA extracted from a cohort of 257 surgically treated NSCLC patients (Table 3) and 2 SCLC cell cultures. Samples were procured as fresh frozen (FF) and FFPE tissues archived between 1-15 years.

Results

The cohort profiled by this qRT-PCR assay of 52 classifiers and 5 control (i.e. housekeeper) genes (Table 1) contained a broad spectrum of tumors in proportions consistent with clinical practice (Table 3). Gene amplification was successful in 238 of 257 (92.6%) lung cancer, normal, and cell culture samples. Matched FF and FFPE had Pearson correlations of approximately 70%. Linear discriminant analysis of gene expression data agreed with morphologic classification by light microscopy with accuracies of 94-100% (Table 3). More importantly, the method successfully re-identified molecular subtypes of lung cancer using a FFPE tissue assay (FIG. 7). Clinical outcomes previously associated with molecular tumor subtypes, including differential survival, were again seen in this cohort (FIG. 8).

TABLE 3

Clinical and pathological parameters of lung samples used in qRT-PCR.

|  | HCI FF | HCI FFPE | UNC FFPE | Total |
|---|---|---|---|---|
|  | 29 | 60 | 168 | 257 |
| Gender |  |  |  |  |
| Male | 12 | 21 | 92 | 125 |
| Female | 15 | 37 | 73 | 125 |
| Cell Cx | 2 | 2 | 0 | 4 |
| Age |  |  |  |  |
| <60 | 8 | 18 | 48 | 74 |
| 60-75 | 17 | 35 | 92 | 144 |
| >75 | 2 | 5 | 23 | 30 |
| Race |  |  |  |  |
| Caucasian | 24 | 57 | 128 | 209 |
| African American | 1 | 1 | 37 | 39 |
| Native American | 1 | 1 | 0 | 2 |
| Smoking status |  |  |  |  |
| ≤20 pkyrs | 1 | 5 | 16 | 22 |
| >20 pkyrs | 14 | 30 | 100 | 144 |
| Positive | 4 | 10 | 26 | 40 |
| Negative | 2 | 5 | 7 | 14 |
| Unknown | 6 | 8 | 19 | 33 |
| Grade |  |  |  |  |
| Well | 1 | 2 | 14 | 17 |
| Well-Moderate | 2 | 5 | 8 | 15 |
| Moderate | 5 | 12 | 88 | 105 |
| Moderate-Poor | 6 | 10 | 14 | 30 |
| Poor | 6 | 10 | 33 | 49 |
| Atypical | 4 | 4 | 0 | 8 |
| Typical | 1 | 1 | 0 | 2 |
| Unknown | 2 | 4 | 11 | 17 |
| Histology |  |  |  |  |
| Normal | 0 | 10 | 0 | 10 |
| SCLC | 2 | 2 | 0 | 4 |
| Carcinoid | 7 | 9 | 0 | 16 |
| SCC | 5 | 12 | 63 | 80 |
| AC | 15 | 27 | 105 | 147 |
| Stage |  |  |  |  |
| IA | 11 | 19 | 61 | 91 |
| IB | 3 | 11 | 37 | 51 |
| IIA | 2 | 2 | 4 | 8 |
| IIB | 2 | 3 | 21 | 26 |
| IIIA | 6 | 9 | 12 | 27 |
| IIIB | 2 | 3 | 3 | 8 |
| IV | 1 | 1 | 0 | 2 |
| Unknown | 0 | 0 | 30 | 30 |

| | | qRT-PCR Prediction | | | | | |
|---|---|---|---|---|---|---|---|
| | | ADENO | COID | NRML | SCC | SCLC | TOTAL |
| Histology | ADENO | 130 |  | 1 | 6 |  | 137 |
| | COID |  | 16 | 1 |  |  | 17 |
| | NRML |  |  | 8 |  |  | 8 |

TABLE 3-continued

Clinical and pathological parameters of lung samples used in qRT-PCR.

| | | | | | |
|---|---|---|---|---|---|
| SCC | 6 | | 1 | 67 | 74 |
| SCLC | | | | 2 | 2 |
| TOTAL | 136 | 16 | 11 | 73 | 2 | 238 |

Conclusions

For the first time, a clinically meaningful and robust molecular diagnosis of a cohort of lung cancer patients which is complementary to morphologic cancer diagnosis is described here. This assay is easily implemented using specimens routinely collected in current patient care.

REFERENCES

1) Potti A, Mukherjee S, Petersen R, et al: A Genomic Strategy to Refine Prognosis in Early-Stage Non-Small-Cell Lung Cancer. N Engl J Med 355:570-580, 2006
2) Beer D G, Kardia S L, Huang C C, et al: Gene-expression profiles predict survival of patients with lung adenocarcinoma. Nat Med 8:816-824, 2002
3) Hayes D N, Monti S, Parmigiani G, et al: Gene Expression Profiling Reveals Reproducible Human Lung Adenocarcinoma Subtypes in Multiple Independent Patient Cohorts. J Clin Oncol 24:5079-5090, 2006

Example 4

Although the differentiation of malignant from normal lung tissue is a very reliable diagnostic distinction, the accurate and reproducible classification of variants of lung cancer has never been described. Although over 100 morphologic variants of lung tumors have been described, for all practical purposes only 2 distinctions are generally made with confidence, the distinction of small cell lung cancer from non-small cell lung cancer (a diagnosis of exclusion). The reason for the unreliability of lung cancer diagnosis includes the general small volumes of tissues and intra-tumor morphologic variation.

New and developing technologies such DNA microarrays have demonstrated that gene expression can reliably distinguish known morphologic variants of lung cancer as well as novel subtypes not otherwise distinguished by any clinically available technology. The technologies currently in place are not appropriate for diagnostic and clinical use due to their cost and technical limitations. There is no current technology for making molecular diagnosis of lung cancer morphologic variants using gene expression measures. There is no current technology for diagnosing molecular subtypes of lung cancer.

Provided herein is the first application of a technology capable of diagnosing both commonly accepted morphologic variants of lung tumors, as well as newly described molecular variants and clinically meaningful behavior of lung cancer such as survival. The approach has a number of novel components. Firstly, its application to lung tumors is new. Secondly, the use of paraffin embedded tissues for molecular diagnosis of lung cancer by gene expression is new. Third, a novel and high-throughput approach was used to independently validate the genes in the classifier. Fourth, a robust novel self-normalizing method of classification was used which allows for a modular predictor. In this approach, predictions are made in 2 ways, using a one versus all and all pairwise approach such that many classes can be predicted using small gene cassettes. Since each of the gene cassettes is independent, new cassettes can be added to the existing predictor without changing the overall method of prediction. This allows the user to add new classes as desired. For example, the current predictor distinguished a total of 9 classes and subclasses of lung cancer (FIG. 1). As new groups of lung cancer are described or as new features of tumor behavior are identified, these can be added to the current predictor as cassettes without changing the existing structure of the classifier.

Gene selection for gene cassettes is in the following manner. A set of gene expression cohorts was selected from among all published reports of lung cancers assayed by gene expression data due to their relatively large size and inclusion of a representative spectrum of tumor variants. Expression datasets were transformed using genomic meta-analysis methods that have been previously reported. Briefly, all arrays were evaluated for the quality of the scanned image. Probes were mapped to genes using Unigene identifiers. In cases where multiple probes mapped to the same Unigene identifier, these were averaged. Genes were evaluated for cross-platform reliability using integrative correlations. Genes with integrative correlations twice that observed by random chance were considered reliable and retained across datasets. Reliable genes were then ranked for each gene for their ability to distinguish each of the morphologic variants in both the 1 versus all (i.e. tumor versus normal) and the all-pairwise (i.e. normal versus small cell carcinoma) case. The statistic used for the ranking was the area under the receiver operator characteristic (ROC) curve (a plot of sensitivity versus (1-specificity)). Although genes were evaluated for reliability across datasets, the independent sample sets were not combined for the purposes of the ROC ranking. As a result, multiple independent analyses were performed and obtained multiple independent rankings for each gene's ability to distinguish groups of interest. A gene was considered reliable if its area under the ROC curve was close to 1 for each of the independent datasets. In cases were a gene's ROC was close to 1 in some but not all datasets, the gene's overall reliability as measured by integrative correlations was considered. The gene selection process was pruned to approximately 100 genes based on prior experience that this was the number that could be reliably obtained from paraffin samples using current techniques.

Using previously described techniques, tumors from the existing cohorts were divided into their respective gene expression subtypes (3 subtypes of lung adenocarcinoma). A similar ROC-based approach to that described above was used to select gene cassettes capable of distinguishing these expression subtypes. Additionally, gene cassettes were selected to identify genes associated with survival and metastasis.

Selecting Housekeeper Genes

Housekeeper (HK) genes were used to control for variation in RNA quality and cDNA input. Nine housekeeper genes that had among the highest average signal/noise ratio across histological types in the preliminary microarray data set were selected. The high average signal/noise ratio suggests relatively high levels of expression and lower variation across the lung sample types. After qRT-PCR profiling across these lung samples, five genes were selected (CFL1, EEF1A1, RPL10, RPL28, and RPL37A) as housekeepers using the statistical methods described in previous reports.

Designing Primers

Genbank sequences were downloaded from Ensembl (which can be found on the internet at www.ensembl.org/Homo_sapiens/index.html, release 42—December 2006) into LightTyper Probe Design software (version: 2.0.B.22) (Roche Applied Science, Indianapolis, Ind.). Primer sets were designed and performance was assessed using criteria described elsewhere. Primers were tested on lung cDNA from FFPE tissue prior to utilization for qRT-PCR. Gene references and primer sequences are listed in Table 1.

qRT-PCR

Each 5 µl PCR reaction included 2-fold concentrated LightCycler 480 SYBR Green I Master Mix (Roche Applied Science, Indianapolis, Ind.) and 2.5 ng (1.25 ng/uL) cDNA. Liquid handling for loading 384-well plates was done using the Evolution P3 Precision Pipetting Platform (PerkinElmer Ltd, Shelton, Conn.). Each run contained an internal 10 ng calibrator reference using cDNA made from Human Reference Total RNA (catalogue number #750500; Stratagene, La Jolla, Calif.) and two small cell lung cultures (DMS 53 and DMS 114). Samples and calibrator were present in duplicate.

PCR amplification was performed in the LC480 (Roche Applied Science, Indianapolis, Ind.) using an initial denaturation step (95° C., 8 minutes) followed by 45 cycles of denaturation (95° C., 4 seconds), annealing (56° C., 6 seconds with 2.5° C./s transition), and extension (72° C., 6 seconds with 2° C./sec transition). Fluorescence (530 nm) from the dsDNA dye SYBR Green I was acquired for each cycle after the extension step. The specificity of the PCR was determined by post-amplification melting curve analysis. Reactions were automatically cooled to 65° C. and slowly heated at 2° C./s to 99° C. while continuously monitoring fluorescence (10 acquisitions/1° C.).

Data Analysis for qRT-PCR

Quantification was performed using the LC480 software (version: 1.2.0.169) (Roche Applied Science, Indianapolis, Ind.). Relative copy numbers were calculated by importing an external standard curve made from a serial 10-fold dilution of GAPDH (efficiency 1.8) and correcting to the Cp of the 10 ng calibrator. The copy number for each classifier gene was normalized to the average of all 5 housekeepers. Samples missing more that 10% of genes were excluded from further analysis. Missing data in remaining samples were imputed using k-nearest neighbor.

Lung Sample Class Prediction

Using the genes selected and measured as described above, a robust self-normalizing classifier was used to predict tumor classes and subclasses. Briefly the self normalizing classifier works in the following manner. For each one versus all and each pairwise classification being made, the gene cassette includes genes which are expressed at high levels relative to the alternative class and low levels relative to the alternative class. It is the ratios that are then used to make the class distinctions, as well as the gene expression values themselves. The use of unitless (normalized) ratios is less sensitive to technical artifacts that occur in the measurement of gene expression and allows more reliable classification. A second set of class calls is made for validation purposes using linear discriminant analysis on housekeeper-normalized gene expression data.

In summary, the present invention provides the first paraffin-based gene-expression-based molecular diagnostic for lung cancer capable of distinguishing a range of biologically and phenotypically relevant tumor classes. This real-time qRT-PCR assay for approximately 100 genes is useful for making accurate lung cancer classifications from either formalin-fixed-paraffin-embedded or fresh tumor biopsy specimens. This assay is appropriate either for grossly resected and small volume biopsies such as fine needle aspirates or cytologic specimens. See FIG. 6.

As noted in FIG. 6, in normal tissue the following genes are upregulated: CDH5, CLE3B, and PECAM1; and the following genes are downregulated: PAICS, PAK1, TFAP2A. In small cell lung carcinoma (SCLC) CDKN2C, INSM1, and STMN1 are upregulated and ACVR1, CIB1, and LRP10 are downregulated. In carcinoid cells (COID) CHGA, MAPRE3, and SNAP91 are upregulated and CAPG, LGALS3, and SFN are downregulated. Table 1 lists additional classifier genes according to class and subclass.

Example 5

Background

Lung cancer is the leading cause of cancer deaths both in the United States and worldwide (1, 2). The irony of clinical lung cancer management is that despite major advances in recent years documenting the effectiveness of a host of interventions (adjuvant chemotherapy, combined modality chemotherapy and radiation, palliative chemotherapy, targeted treatments), more than 85% of patients diagnosed with lung cancer will die of their disease, often in less than a year. (3-7). A compelling argument can be made that a single fact explains the striking disconnect between the number of available effective therapies and the poor outcomes for lung cancer patients. There are very limited tools to assist practitioners in matching the correct therapies to the patients likely to benefit from them. In current practice, two pieces of information are generally all that is considered when prescribing therapy to lung cancer patients: small-cell versus non-small cell morphology and clinical stage.

Lung Cancer Genomics

Previous clinical work has demonstrated the probable success in predicting surgically-treated patients at high risk for recurrence and death. The ability of microarrays to reliably distinguish gross histologic subtypes, such as tumor versus normal lung, has been demonstrated by a number of authors (34, 36, 37). Genomic meta-analysis has been developed, documenting for the first time the reproducibility of subtypes of lung adenocarcinoma. Using 5 independent cohorts totaling approximately 500 patients, it has been demonstrated that morphologically indistinguishable tumors not otherwise classifiable by existing diagnostics can be reliably subdivided into 3 subgroups (coined bronchioid, squamoid, and magnoid) based on differences in gene expression (FIG. 9). These differences are not a subtle statistical phenomenon, but involve differential co-expression within the subgroups of as many as ⅓ of all expressed genes in the tumors. Accordingly, these novel adenocarcinoma subtypes appear to account for a host of clinical patterns of lung cancer, including probability of recurrence, survival, and metastatic pattern (43). Although the technologies that allow expression profiling are barely a decade old, findings parallel to those described above have been successfully validated in a range of tumors, perhaps most definitively in breast cancer, lymphoma, and leukemia (45-47).

Squamous Cell Carcinoma

Building on work with adenocarcinomas, risk stratification was also performed for SCC, the other major histological types of NSCLC using expression profiling. There is only one report of different tumor subtypes of SCC by DNA microarrays (44). As with the AD subtypes, the reported subtypes differ dramatically in terms of survival, in this case for 2 subtypes of SCC, with six year survival 80% in the favorable group compared to 40% in the unfavorable (p=01). Hayes et al. have been able to validate the 2 distinct subtypes of SCC based on gene expression patterns (43). Additionally, the magnitude of the survival difference in SCC subtypes has been documented, as in the original report by Inamura, although this did not meet a significance level of p=0.05 due to small numbers (FIG. 10. hazard ratio 0.55 p=0.18, 6 year survival 60% versus 20% p=0.13).

Data Sources

Microarray gene expression data of squamous lung tumors and clinical information corresponding to two independent published studies, referred to as veridex (1) and duke (2), were downloaded from publicly available websites (3, 4). Veridex gene expression data was derived from the Affymetrix U133A array and contains probeset expression values generated by the MAS5 algorithm. Duke gene expression data was derived from the Affymetrix U133 Plus 2 array and provides probe-level expression values in the Affymetrix CEL format. The veridex set consists of 130 squamous lung tumor samples. The duke set consists of 53 squamous samples.

Two-Study Gene Annotation Mapping

For this study, gene annotation space is defined by HUGO gene symbols. Veridex probeset expression values were averaged by their HUGO identifier. For the duke set, a custom probe to probeset mapping (CDF) was built using blat (5) alignment of the probe sequences to mRNA transcript sequences downloaded from the SpliceMiner website (genepattern.broad.mit.edu/gp/pages/index.jsf). This custom CDF was used to create MAS5 gene expression values.

Lung Tumor Squamous Subtypes Defined by Unsupervised Clustering in Independent Data Sets In order to effectively cluster tumor samples, a gene list was constructed on the basis of statistical variability. For this list, genes with a median absolute deviation in the veridex set exceeding and also present in duke set were selected for a total of 2,361 genes. Consensus hierarchical clustering (6, 7) was executed independently for the veridex and duke sets to define the number of lung tumor squamous subtypes. The associated consensus distribution graphs and graphics support 3 distinct clusters in both datasets. Correlations of cluster medoids were calculated to identify corresponding clusters between the data sets. (Table 4) These correlations show a clear one-to-one cluster mapping between the data sets. These correlations show that these clusters are detectable in independent tumor sample sets by different gene expression assays and provide evidence that these clusters are the result of biological processes driving gene expression rather than a result of technical artifacts. In order to refer to these clusters, a name was assigned to each cluster based on manually-selected genes that exhibited differential expression relative to the two other clusters. These clusters are named as the keratin-low subtype, the ms-high subtype, and the mucin-high subtype.

TABLE 4

Correlation of cluster medoids between duke and veridex data sets.

| duke cluster | veridex cluster 1 | 2 | 3 |
|---|---|---|---|
| 1 | 0.65669834 | −0.42840407 | −0.20990321 |
| 2 | 0.18027364 | −0.23557283 | 0.37177577 |
| 3 | −0.39141677 | 0.58898719 | 0.14150200 |

Genes Significantly Associated with Subtype

To identify genes associated with each subtype, the Rank Product method (8) was executed to identify statistically significant genes over-expressed and under-expressed. The top 20 over-expressed and top 20 under-expressed genes as ranked by lowest percent false positive were extracted from the following comparisons: keratin-low versus ras-high and mucin-high; ras-high versus keratin-low and mucin-high; mucin-high versus keratin-low and ras-high). Of these 60 genes, there are non-redundant genes that are associated with these subtypes, which are listed in Table 1 under the subheading "SCC subtype genes."

Survival of Subtypes

Veridex tumor samples were analyzed for survival as a function of subtype. Kaplan-Meier survival curves in the interval 0 to 36 months (FIG. 14) suggest some differences in survival. The mucin-high versus keratin-low and rash-high versus keratin-low survival curves approach statistical significance, with p=0.1485 and p=0.165 respectively.

REFERENCES

1. Raponi, M., et al. (2006) Gene Expression Signatures for Predicting Prognosis of Squamous Cell and Adenocarcinomas of the Lung. Can Res. 66:15.
2. Bild et al. (2005). Oncogenic pathway signatures in human cancers as a guide to targeted therapies. Nature.
3. http://www.ncbi.nlm.nih.gov/geo/query/acc.cgi?acc=GSE4573
4. http://data.genome.duke.edu/oncogene.php
5. Kent, W. J. (2002). BLAT—The BLAST-Like Alignment Tool. Genome Res. 12:4.
6. http://www.tigerteamconsulting.com/SpliceMiner/
7. Monti, S., et al. (2003) Consensus Clustering: A Resampling-Based Method for Class Discovery and Visualization of Gene Expression Microarray Data. Machine Learning. 52:1-2.
8. Breitling, R., et al. (2004) Rank products: a simple, yet powerful, new method to detect differentially regulated genes in replicated microarray experiments. FEBS letters. 573:1-3.

Small Cell Carcinoma

Tumor subtypes have been described for SCLC carcinoma in a single large case series, high-grade neuroendocrine tumors type I and II (HGNET1 and HGNET2) (20). Patients with SCLC rarely undergo surgery, and independent data are too sparse to make confirmatory statements on this finding.

Translation to Clinical Medicine

While the interest in expression profiling both for clinical and research purposes continues to grow, there are limitations which must be addressed to bring the promise of this technology to routine patient care. Chief among these is that, gene expression arrays rely on the availability of relatively large amounts of fresh tissue which is commonly available for patients with lung cancer. While technological advances or changes in clinical practice might ultimately allow expression arrays to enter routine patient care, most agree that an assay targeted to the routinely prepared formalin-fixed paraffin-embedded tissue would be strongly preferred. Methods of real-time PCR techniques for genetic testing and tumor profiling have developed and implemented.

To maximize the chances of success, this project was designed around the concept of genomic classifier validation. A diagnostic test or "classifier" is validated if genes derived from one data set and used for diagnosis or "classification" in an independent data set (Test Set) produce the same results. If a classifier can pass this test, then it is strong enough to be independent of technical peculiarities specific to one platform, or to sampling bias.

Selection of Valid Genes

To ensure that genes selected for the current proposal are most likely to be valid, a cohort was assembled of all available lung cancer arrays (11, 13, 14, 16-18, 20, 31, 32, 34, 35, 59). In all, this totals over 1000 patient samples from diverse backgrounds (ethnicity and geographic location) and different environmental exposures (smokers and non-smokers). These independent cohorts allow pre-selection and validation of genes with properties most favorable for further testing using a PCR-based assay in paraffin samples. Although the focus of the current work is on novel methods of classification of lung cancer, the most conservative approach may be a proof of principle using conventional morphologic classes of lung cancer (i.e. SCC, AD, etc). To accomplish this goal, an independent validation of a classifier that detects the different histological types of lung cancer was performed using methods of combining genomic data which have previously been reported (43). Once the data were merged into a single cohort, samples were divided into the training and testing sets. Genes were selected in the training set that distinguished each morphologic lung cancer class from the others using the relative difference statistic as implemented in the statistical analysis of microarrays algorithm, a method which accounts for the probability of false discovery of spurious associations. Based on experience derived from work in breast cancer, the list of several thousand highly significant candidate genes was culled to the top 500, a group called the Preliminary Data Classifier (PDC). These genes were used to prove an upper bound on the expected performance of a clinical assay. Using a nearest centroid classifier, expression based diagnosis agreed with the pathologist's histological diagnosis in 93% of cases (60, 61). This level of agreement compares very favorably to historic reports of the reliability of lung cancer morphologic classification which can fall between 70-90%, but which generally have been lower (62-64). All of the cases in which there was a disagreement between genomic diagnosis and morphologic diagnosis were reviewed. One-third of discrepant cases were from samples with less that 40% tumor nuclei, and 1/3 cases were poorly differentiated tumors without a consensus of the diagnosis after review by multiple pathologists. In brief, accounting for poor quality samples and samples in which the underlying diagnosis was unclear, the agreement between genomic classifier and morphologic classifier was nearly perfect.

Perfect agreement between "truth" and "prediction" in a genomic study such as this would generally be a sign of data over-fitting and a cause for concern. To evaluate the validity of the 500 gene list, the exact classifier was applied to an independent test set where agreement between genomic prediction and histological diagnosis was 91%. Importantly, all non-neoplastic samples were correctly identified as normal lung by the classifier. Eighty percent of the cases where the classifier was discordant with the histological diagnosis were from small volume samples. Interestingly, the test set contained a set of samples given only nonspecific diagnosis by the pathologist of either NSCLC or simply "carcinoma" where the expression-based classifier was able to make unambiguous calls for >75%.

Use of Paraffin-Embedded Tissue

To test the feasibility of gene expression profiling from paraffin-embedded lung cancer samples, cohort of 157 lung cancer and normal samples was assembled from banked paraffin tissues at the University of North Carolina and the Huntsman Cancer Institute at the University of Utah. From the 500 genes of the PDC, a representative set of 62 genes (8 housekeeper and 54 tumor classifying genes) was selected for PCR analysis using methods previously reported (58). Primer pairs were designed using commercially available software and evaluated using model cell lines representative of the dominant lung cancer morphologic variants. RNA was extracted using the High Pure Paraffin RNA Extraction Kit (Roche) from 4 full face 10 micron sections, PCR amplified and quantified using standard methods. Using a modification of the ΔΔCp method, relative copy number for each gene of interest in these lung cancer samples was calculated. The copy number for each control and test gene in an experimental sample is first normalized to the same genes in a common reference sample. This copy number for each test gene is then corrected for differences in starting material by dividing by the average copy number of several control (housekeeper) genes. The results demonstrate that of the 62 selected targets, 61 primer pairs passed quality control in the cell line system. Fifty-eight genes were successfully amplified in at least 90% of clinical samples. RNA was amplified for 90% of gene targets in 98% of the samples tested. Twenty samples were assayed in duplicate or triplicate with the mean Pearson's correlation coefficient of gene expression data across the replicate pairs of 0.94. Five percent of samples had both frozen and paraffin-embedded tissue for confirmation with mean Pearson's correlation coefficient of >80%. This cohort included patients whose paraffin tumors were banked between 1-15 years ago, with a trend towards more failed amplifications in the oldest samples. Overall, however, the yields were considered good to excellent. To test the ability of these gene expression data to correctly identify the morphologic lung cancer variants, linear discriminant analysis was used and the results are shown in FIG. 11. Remarkably, in 93% of cases, the morphologic diagnosis and gene expression diagnosis agreed. Discordant cases were of 3 varieties: adenocarcinoma called squamous cell carcinoma, squamous cell carcinoma called adenocarcinoma, and tumor identified as normal. Review of the cases where tumor was misidentified as normal revealed samples of either low tumor content or poor RNA amplification.

SUMMARY

The ability to select a robust set of genes which can be profiled using routinely available clinical samples for the purposes of gene expression profiling was successfully demonstrated. In this proof of principle example, it was shown that this system can be used to make clinically meaningful distinctions and open the possibility for a range of novel diagnostics in lung cancer.

Development and Validation of an Expression-Based Classification of Lung Cancer Using Real-Time qRT-PCR from Formalin-Fixed Paraffin-Embedded (FFPE) Tissues Tumor Subtypes and Sample Selection The only current means of distinguishing subtypes of lung AD, SCC, and SCLC is through the use of gene expression arrays. Therefore, in order to assess the accuracy of the paraffin assay described herein, a set of lung cancer samples is assayed in the following parallel manner: fresh frozen tissue is hybridized against gene expression arrays and FFPE tissue is assayed using real-time qRT-PCR. Additionally, as part of the quality control evaluation of gene targets, real-time qRT-PCR on RNA isolated from fresh tissue taken in parallel with matched FFPE tissue is performed. To ensure sufficient power to validate the diagnostic ability of this assay, a new cohort of lung cancer patients is assembled with both frozen and matched FFPE tissue available, herein referred to as the UNC cohort. Tumors are collected sequentially, and to ensure an appropriate mix of tumors for classification, patients are sampled with the following distribution of morphologic diagnoses: SCLC 15 (50/50), SCC 25 (60/30), AD 40(40/40/20), carcinoid 10, normal lung 10. The values in parentheses represent the relative proportions of tumor subtypes for each morphologic diagnosis based on previous reports. In the case of SCC, the preliminary data suggest either 60/30 or 50/50 split of tumor subtypes. The relative proportions of each tumor type were selected to ensure at least 7 samples per tumor subtype. The selection of 7 as a minimum comes from the experience that multiple existing datasets in this collection contained 7 or fewer small cell carcinomas, yet still provided interpretable data for genomic analysis. The total sample size was estimated based on the finding that agreement between morphologic and molecular diagnosis was 93%, a value at the upper end of that reported for the inter-observer agreement between pathologists (63). Under the null hypothesis of 93% agreement and alternate hypothesis of 85% agreement with power of 80% and alpha of 0.05, a minimum of 90 total samples is required. Therefore, the reproducibility of expression based classification on an order of magnitude that allows comparison to morphologic classification as determined by traditional light microscopy. For the current analysis there is no attempt to differentiate large cell lung cancer (LCLC) as an entity separate from adenocarcinoma. There are few published reports documenting the reliability of a LCLC diagnosis, and in previous publications of microarray data it tended to cluster most closely with a subtype of adenocarcinoma.

Starting with the cohort of 1000 lung cancer microarray samples described above, a process similar to that described in the proof of principle analysis is used. Using the nearest centroid methods, all SCC and AD NSCLC are assigned to their respective tumor subtypes (43, 60). The PDC is reconstructed by first selecting only those genes which are reliably measured across the independent datasets in the cohorts using the integrative correlations method (37). Using only these highly reliable genes, the 500 genes most associated with each of the following categories of tumor are selected: normal lung parenchyma, SCLC, SCC, AD, and carcinoid. The 500 genes will also include a set which distinguishes the 3 known subtypes of AD (bronchioid, squamoid, and magnoid), 2 reported subtypes of SCC (A and B), and the reported subtypes of small cell carcinoma (HGNET1 and HGNET2). Gene pre-selection for the PDC in this rich collection of multiple independent datasets ensure that genes ultimately selected for validation in the following steps are highly likely to be associated with the diagnostic groups of interest and not spurious. The performance of the PDC is evaluated as described in the section tiled selection of valid genes above. Samples from the UNC cohort constitute the test set, and as such, are assigned to tumor subtypes but not used in selection of genes for the PDC.

Gene and Primer Validation

The performance of the PDC is evaluated in the 1000 sample cohort to estimate the upper bound on reliability on tumor classification. The 500 gene PDC is reduced to 100 genes by the nearest shrunken centroid method (65). The 100 most predictive genes, called the calibrated classifier (CC), are then be evaluated for their predictive power in the UNC cohort of expression arrays to estimate the upper limit on the predictive power of the FFPE assay. If the CC underperforms with regard to expected diagnostic power, the PDC is repeated to refine a more predictive gene set. This method allows for the subtle refinement in the training CC without considering genes from the test set (the UNC cohort) where the risk of selecting spurious genes is highest. With the CC calibrated in this manner the real-time qRT-PCR is designed as described above. Briefly, commercial software is used to design the real-time qRT-PCR primer pairs, which are all evaluated for the uniqueness of their targets in the genome by sequence searches. All primer sets are designed to have a Tm≈60° C., GC content≈50% and to generate a PCR amplicon<100 bps. All primer sets are tested using SYBR Green to assess efficiency of PCR and the presence of primer-dimers. Melting curve analysis is used to distinguish primer-dimer formation from specific product. Each new primer set will first be tested for performance using the following criteria: 1) Target Cp<30 using 10 ng reference cDNA, 2) PCR efficiency>1.7, 3) No primer-dimers in presence of template, and 4) No primer-dimers in negative template control before cycle 40.

Each target gene of the CC is evaluated first by real-time qRT-PCR from fresh tissue to ensure good correlation with matched expression measured by DNA microarray. Genes with high correlation between expression array and PCR based quantification are included in the final CC set for evaluation in paraffin. Primers which generate poor correlation between the expression array and real-time qRT-PCR as measured in fresh tissue are replaced. The first attempt considers new primers for the same target. If these fail then a new gene is selected from the PDC. In a similar manner, the correlations of real-time qRT-PCR from paraffin to paired expression from the microarray and real-time qRT-PCR from fresh tissue is performed, replacing any genes with poor overall correlation with alternates from the PDC.

In a final step the CC genes are used to classify the 100 samples with regard to both tumor morphology and tumor subtypes. If there are systematic errors in the classification, this represents an additional opportunity to return to the PDC to select alternate candidates. The design is a 2 stage algorithm in which the first prediction is of morphologic variant followed in a second step by prediction of tumor subtype (FIG. 12).

Assessing Predictive and Prognostic Significance of Molecular Subtypes of Non-Small Cell Lung Cancer:

This step documents the associations between lung cancer subtypes and clinical outcomes including relapse-free survival, overall survival, pattern of recurrence, and response to first line chemotherapy.

Relapse-Free Survival and Overall Survival

Previous reports of AD, SCC, and SCLC tumor subtypes have reported clinically meaningful differences in survival according to tumor subtype as measured by expression microarrays. Both retrospective and prospective cohorts of each of these tumors are assembled to confirm these associations using the qRT-PCR assay. Historical patients are restricted to early stage, surgically treated individuals with 5 years of follow up. Recurrence pattern and dates are recorded in a database. All surgically treated incidental patients are followed prospectively for recurrence and overall survival. Paraffin samples are obtained for both groups and analyzed with the assay developed in specific aim 1. Relapse-free and overall survival are assessed using standard Kaplan-Meier plots as well as Cox proportional hazards modeling.

In samples identified as AD, the hypothesis is based on repeated observation in preliminary data of a 25% absolute improvement in survival at 5 years from 50% to 75% for the bronchioid subtype. To detect this difference at an 80% power with a one-sided alpha of 0.05, 58 samples per class are needed. Since bronchioids and squamoids together comprise 80% of AD (40% each with the remaining 20% being magnoids), a total of 145 AD samples are needed. In samples identified as SCC, the hypothesis is that there is a 30% absolute survival benefit from 80%-50% between the 2 subtypes, with subtype 2 having the favorable prognosis. Assuming the differential survival above, with an alpha of 0.05 and 80% power the total sample size is 76 SCC tumors. To ensure a minimum of 76 SCC and 145 AD from an unselected cohort of NSCLC tumors, the following calculation is made. Approximately 35% of NSCLC are SCC with the remainder assumed to be AD. The maximum of 76/0.35 and 145/0.65 is 223. Therefore 223 NSCLC patients is expected to produce a cohort sufficient to test the hypotheses above. In the case of SCLC preliminary data for the use of tumor subtypes suggests a dramatic survival differential between subtypes of 50%. To detect a 50% difference in survival at 3 years with 80% power and an alpha of 0.05, 28 patients are needed.

Chemotherapy Treatment Response

Most patients treated with chemotherapy are in the setting of advanced and unresectable disease. To evaluate the association between PCR-based diagnosis of tumor subtype and treatment response, the following 2 categories of patients with gross tumor available are used for analysis: (1) recurrence after surgical resection, (2) patients with advanced disease who have gross tumor resected, including mediastinoscopy or other open surgical procedure. Of the 2500 patients with FFPE available in the pathology banks, approximately 750 patients will have recurred and have tissue available in the banks. The majority of these patients will have received platinum-based chemotherapy in the first line setting. Evidence from a variety of sources suggests that patients of the bronchioid subtype are approximately half as likely to respond to platinum-containing regimens, with the best estimate coming from a clinical trial published in the Lancet (66). Based on these data the hypothesized response rate for the bronchioid subtype is 25% compared to 40% for all other NSCLC. With a one-sided alpha of 0.05 and 80% power, 320 patients are required to test this hypothesis.

Pattern of Recurrence

An estimated 30% of the 223 NSCLC patients from the Survival cohort above (n=70) will be diagnosed with metastases by the end of their follow-up. The majority of the 320 patients from Chemotherapy cohort will either have a metastasis present at diagnosis or develop metastasis during follow-up. The association between tumor subtype and specific patterns of recurrence (bone, brain, local, and visceral) is assessed using these two established cohorts as well as the prospective cohort described above using logistic regression models. Of particular interest are the reported association between squamoid adenocarcinoma subtype and brain recurrence, and the overall high rate of metastasis in this subtype relative to the bronchioid subtype.

REFERENCES

1. American Cancer Society, Cancer Facts & Figures; 2005.
2. GLOBOCAN 2000: Cancer Incidence, Mortality and Prevalence Worldwide, Version 1.0, IARC CancerBase No. 5. Lyon: World Health Organization; 2001.
3. Bulzebruck H, Bopp R, Drings P, et al. New aspects in the staging of lung cancer. Prospective validation of the International Union Against Cancer TNM classification. Cancer 1992; 70(5):1102-10.
4. AJCC Cancer Staging Handbook. 6th Edition ed; 2002.
5. Detterbeck F C, Rivera M P, Socinski M A, Rosenman J. Diagnosis and Treatment of Lung Cancer. Philadelphia, Pa.: W.B. Saunders; 2001.
6. Chemotherapy in non-small cell lung cancer: a meta-analysis using updated data on individual patients from 52 randomised clinical trials. Non-small Cell Lung Cancer Collaborative Group. Bmj 1995; 311(7010):899-909.
7. Agra Y, Pelayo M, Sacristan M, Sacristan A, Serra C, Bonfill X. Chemotherapy versus best supportive care for extensive small cell lung cancer. Cochrane Database Syst Rev 2003(4):CD001990.
8. Chen G, Gharib T G, Wang H, et al. Protein profiles associated with survival in lung adenocarcinoma. Proc Natl Acad Sci USA 2003; 100(23):13537-42.
9. Yanagisawa K, Shyr Y, Xu B J, et al. Proteomic patterns of tumour subsets in non-small-cell lung cancer. Lancet 2003; 362(9382):433-9.
10. Zhao X, Weir B A, LaFramboise T, et al. Homozygous deletions and chromosome amplifications in human lung carcinomas revealed by single nucleotide polymorphism array analysis. Cancer Res 2005; 65(13):5561-70.
11. Garber M E, Troyanskaya O G, Schluens K, et al. Diversity of gene expression in adenocarcinoma of the lung. Proc Natl Acad Sci USA 2001; 98(24):13784-9.
12. MacAulay C, Lonergan K, Chi B, et al. Serial analysis of gene expression profiles of developmental stages in non-small cell lung carcinoma. Chest 2004; 125(5 Suppl):97S.
13. Bhattacharjee A, Richards W G, Staunton J, et al. Classification of human lung carcinomas by mRNA expression profiling reveals distinct adenocarcinoma subclasses. Proc Natl Acad Sci USA 2001; 98(24):13790-5.
14. Beer D G, Kardia S L, Huang C C, et al. Gene-expression profiles predict survival of patients with lung adenocarcinoma. Nat Med 2002; 8(8):816-24.
15. Bonner A E, Lemon W J, Devereux T R, Lubet R A, You M. Molecular profiling of mouse lung tumors: association with tumor progression, lung development, and human lung adenocarcinomas. Oncogene 2004; 23(5):1166-76.
16. Borczuk A C, Gorenstein L, Walter K L, Assaad A A, Wang L, Powell C A. Non-small-cell lung cancer molecular signatures recapitulate lung developmental pathways. Am J Pathol 2003; 163(5):1949-60.
17. Borczuk A C, Shah L, Pearson G D, et al. Molecular signatures in biopsy specimens of lung cancer. Am J Respir Crit Care Med 2004; 170(2):167-74.
18. Gordon G J, Jensen R V, Hsiao L L, et al. Using gene expression ratios to predict outcome among patients with mesothelioma. J Natl Cancer Inst 2003; 95(8):598-605.
19. Hoang C D, D'Cunha J, Tawfic S H, Gruessner A C, Kratzke R A, Maddaus M A. Expression profiling of non-small cell lung carcinoma identifies metastatic genotypes based on lymph node tumor burden. J Thorac Cardiovasc Surg 2004; 127(5):1332-41; discussion 42.
20. Jones M H, Virtanen C, Honjoh D, et al. Two prognostically significant subtypes of high-grade lung neuroen- 20. docrine tumours independent of small-cell and large-cell neuroendocrine carcinomas identified by gene expression profiles. Lancet 2004; 363(9411):775-81.
21. Kikuchi T, Daigo Y, Katagiri T, et al. Expression profiles of non-small cell lung cancers on cDNA microarrays: identification of genes for prediction of lymph-node metastasis and sensitivity to anti-cancer drugs. Oncogene 2003; 22(14):2192-205.
22. McDoniels-Silvers A L, Stoner G D, Lubet R A, You M. Differential expression of critical cellular genes in human lung adenocarcinomas and squamous cell carcinomas in comparison to normal lung tissues. Neoplasia 2002; 4(2):141-50.
23. Miura K, Bowman E D, Simon R, et al. Laser capture microdissection and microarray expression analysis of lung adenocarcinoma reveals tobacco smoking- and prognosis-related molecular profiles. Cancer Res 2002; 62(11):3244-50.
24. Nakamura H, Saji H, Ogata A, et al. cDNA microarray analysis of gene expression in pathologic Stage IA nonsmall cell lung carcinomas. Cancer 2003; 97(11):2798-805.
25. Pass H I, Liu Z, Wali A, et al. Gene expression profiles predict survival and progression of pleural mesothelioma. Clin Cancer Res 2004; 10(3):849-59.
26. Pedersen N, Mortensen S, Sorensen S B, et al. Transcriptional gene expression profiling of small cell lung cancer cells. Cancer Res 2003; 63(8):1943-53.
27. Singhal S, Amin K M, Kruklitis R, et al. Alterations in cell cycle genes in early stage lung adenocarcinoma identified by expression profiling. Cancer Biol Ther 2003; 2(3):291-8.
28. Singhal S, Amin K M, Kruklitis R, et al. Differentially expressed apoptotic genes in early stage lung adenocarcinoma predicted by expression profiling. Cancer Biol Ther 2003; 2(5):566-71.
29. Sugita M, Geraci M, Gao B, et al. Combined use of oligonucleotide and tissue microarrays identifies cancer/testis antigens as biomarkers in lung carcinoma. Cancer Res 2002; 62(14):3971-9.
30. Tomida S, Koshikawa K, Yatabe Y, et al. Gene expression-based, individualized outcome prediction for surgically treated lung cancer patients. Oncogene 2004; 23(31):5360-70.
31. Virtanen C, Ishikawa Y, Honjoh D, et al. Integrated classification of lung tumors and cell lines by expression profiling. Proc Natl Acad Sci USA 2002; 99(19):12357-62.
32. Wigle D A, Jurisica I, Radulovich N, et al. Molecular profiling of non-small cell lung cancer and correlation with disease-free survival. Cancer Res 2002; 62(11):3005-8.
33. Wikman H, Kettunen E, Seppanen J K, et al. Identification of differentially expressed genes in pulmonary adenocarcinoma by using cDNA array. Oncogene 2002; 21(37):5804-13.
34. Yamagata N, Shyr Y, Yanagisawa K, et al. A training-testing approach to the molecular classification of resected non-small cell lung cancer. Clin Cancer Res 2003; 9(13):4695-704.
35. Lim E H, Aggarwal A, Agasthian T, et al. Feasibility of using low-volume tissue samples for gene expression profiling of advanced non-small cell lung cancers. Clin Cancer Res 2003; 9(16 Pt 1):5980-7.
36. Jiang H, Deng Y, Chen H S, et al. Joint analysis of two microarray gene-expression data sets to select lung adenocarcinoma marker genes. BMC Bioinformatics 2004; 5:81.
37. Parmigiani G, Garrett-Mayer E S, Anbazhagan R, Gabrielson E. A cross-study comparison of gene expression studies for the molecular classification of lung cancer. Clin Cancer Res 2004; 10(9):2922-7.
38. Xi L, Lyons-Weiler J, Coello M C, et al. Prediction of lymph node metastasis by analysis of gene expression profiles in primary lung adenocarcinomas. Clin Cancer Res 2005; 11(11):4128-35.
39. Endoh H, Tomida S, Yatabe Y, et al. Prognostic model of pulmonary adenocarcinoma by expression profiling of eight genes as determined by quantitative real-time reverse transcriptase polymerase chain reaction. J Clin Oncol 2004; 22(5):811-9.
40. Gordon G J, Richards W G, Sugarbaker D J, Jaklitsch M T, Bueno R. A prognostic test for adenocarcinoma of the lung from gene expression profiling data. Cancer Epidemiol Biomarkers Prev 2003; 12(9):905-10.
41. Chen H Y, Yu S L, Chen C H, et al. A five-gene signature and clinical outcome in non-small-cell lung cancer. N Engl J Med 2007; 356(1):11-20.
42. Potti A, Mukherjee S, Petersen R, et al. A genomic strategy to refine prognosis in early-stage non-small-cell lung cancer. N Engl J Med 2006; 355(6):570-80.
43. Hayes D N, Monti S, Parmigiani G, et al. Gene expression profiling reveals reproducible human lung adenocarcinoma subtypes in multiple independent patient cohorts. J Clin Oncol 2006; 24(31):5079-90.
44. Inamura K, Fujiwara T, Hoshida Y, et al. Two subclasses of lung squamous cell carcinoma with different gene expression profiles and prognosis identified by hierarchical clustering and non-negative matrix factorization. Oncogene 2005; 24(47):7105-13.
45. Bullinger L, Dohner K, Bair E, et al. Use of gene-expression profiling to identify prognostic subclasses in adult acute myeloid leukemia. N Engl J Med 2004; 350(16): 1605-16.
46. Fan C, Oh D S, Wessels L, et al. Concordance among gene-expression-based predictors for breast cancer. N Engl J Med 2006; 355(6):560-9.
47. Lossos I S. Molecular pathogenesis of diffuse large B-cell lymphoma. J Clin Oncol 2005; 23(26):6351-7.
48. Bennett C D, Campbell M N, Cook C J, et al. The LightTyper: high-throughput genotyping using fluorescent melting curve analysis. Biotechniques 2003; 34(6): 1288-92, 94-5.
49. Bernard P S, Wittwer C T. Real-time PCR technology for cancer diagnostics. Clin Chem 2002; 48(8):1178-85.
50. Layfield L J, Bernard P S, Goldstein N S. Color multiplex polymerase chain reaction for quantitative analysis of epidermal growth factor receptor genes in colorectal adenocarcinoma. J Surg Oncol 2003; 83(4):227-31.
51. Lewis T B, Robison J E, Bastion R, et al. Molecular classification of melanoma using real-time quantitative reverse transcriptase-polymerase chain reaction. Cancer 2005; 104(8):1678-86.
52. Millward H, Samowitz W, Wittwer C T, Bernard P S. Homogeneous amplification and mutation scanning of the p53 gene using fluorescent melting curves. Clin Chem 2002; 48(8):1321-8.
53. Bernard P S, Wittwer C T. Homogeneous amplification and variant detection by fluorescent hybridization probes. Clin Chem 2000; 46(2):147-8.

54. Bernard P S, Ajioka R S, Kushner J P, Wittwer C T. Homogeneous multiplex genotyping of hemochromatosis mutations with fluorescent hybridization probes. Am J Pathol 1998; 153(4):1055-61.

55. Bernard P S, Lay M J, Wittwer C T. Integrated amplification and detection of the C677T point mutation in the methylenetetrahydrofolate reductase gene by fluorescence resonance energy transfer and probe melting curves. Anal Biochem 1998; 255(1):101-7.

56. Bernard P S, Pritham G H, Wittwer C T. Color multiplexing hybridization probes using the apolipoprotein E locus as a model system for genotyping. Anal Biochem 1999; 273(2):221-8.

57. Robison J E, Perreard L, Bernard P S. State of the science: molecular classifications of breast cancer for clinical diagnostics. Clin Biochem 2004; 37(7):572-8.

58. Perreard L, Fan C, Quackenbush J F, et al. Classification and risk stratification of invasive breast carcinomas using a real-time quantitative RT-PCR assay. Breast Cancer Res 2006; 8(2):R23.

59. Bild A H, Yao G, Chang J T, et al. Oncogenic pathway signatures in human cancers as a guide to targeted therapies. Nature 2006; 439(7074):353-7.

60. Dabney A R. Classification of microarrays to nearest centroids. Bioinformatics 2005; 21(22):4148-54.

61. Tibshirani R, Hastie T, Narasimhan B, Chu G. Diagnosis of multiple cancer types by shrunken centroids of gene expression. Proc Natl Acad Sci USA 2002; 99(10):6567-72.

62. Burnett R A, Howatson S R, Lang S, et al. Observer variability in histopathological reporting of non-small cell lung carcinoma on bronchial biopsy specimens. J Clin Pathol 1996; 49(2):130-3.

63. Burnett R A, Swanson Beck J, Howatson S R, et al. Observer variability in histopathological reporting of malignant bronchial biopsy specimens. J Clin Pathol 1994; 47(8):711-3.

64. Sorensen J B, Hirsch F R, Gazdar A, Olsen J E. Interobserver variability in histopathologic subtyping and grading of pulmonary adenocarcinoma. Cancer 1993; 71(10):2971-6.

65. Institute of Mathematical Statistics. Statistical science: a review journal of the Institute of Mathematical Statistics. In. [Hayward, Calif.]: The Institute; 1986:v.

66. Georgoulias V, Papadakis E, Alexopoulos A, et al. Platinum-based and non-platinum-based chemotherapy in advanced non-small-cell lung cancer: a randomised multicentre trial. Lancet 2001; 357(9267):1478-84.

Example 6. Molecular Markers Distinguish Patients at Differential Risk of Brain Metastases in Lung Cancer by Immunohistochemistry Background Patients with surgically resected lung cancer, even at the earliest stages of disease still face a risk of recurrence between 30-50%, including a significant number of patients with brain only metastases. Although evidence suggests brain metastases may be preventable through prophylactic cranial radiation (PCR), widespread acceptance of the therapy has not occurred due to patient preference and other factors. Predictors of brain metastasis might promote the use of PCR.

Methods 150 surgically treated lung cancer patients treated at the University of North Carolina were selected for analysis. A tissue microarray was generated from primary tumor material and assayed this using commercially available antibodies for 16 proteins suspected or previously reported to be associated with brain metastases (TTF1, Vimentin, SMA, BCL2, cyclin D1, UPA, AKT, pAKT, ADAM9, ERK, pERK, EGFR, Her-2/neu, Ki67, p53,Rb,). Samples were assayed in triplicate at a minimum and associations with pattern of metastasis were determined.

Results

The cohort contained 85 adenocarcinomas, 59 squamous cell carcinomas, and 6 poorly differentiated carcinomas. There were 58 recurrence in total of which 38 were solitary recurrences (21 lung only, 9 brain only, 5 liver only, 3 misc). A total of 13 brain metastases occurred, 11 of which were in lung adenocarcinoma. The following patterns were observed. Patients who were TTF1 (+) at any level and vimentin (−), had a documented brain metastasis rate of 4%, compared to patients who were TTF1 (+), vimentin (+) where the rate was 17% (p=0.06). All of the remaining patients with brain metastases were negative for both TTF1 and vimentin, but stained at approximately 2 time background for SMA (p<0.05). Additional antibodies correlated with brain metastases were UPA and ADAM9.

Conclusions

Patients at relatively high and low risk of brain metastasis can be identified using a small number of immunohistochemical markers.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

That which is claimed:

1. A method of detecting biomarkers in a lung tissue sample obtained from a human patient, the method comprising measuring an expression level of nucleic acid for every classifier gene in a group of classifier genes consisting of only a.) Cadherin 5 (CDH5), C-Type Lectin Domain Family 3 Member B (CLEC3B), Platelet And Endothelial Cell Adhesion Molecule 1 (PECAM1), Phosphoribosylaminoimidazole Carboxylase And Phosphoribosylaminoimidazolesuccinocarboxamide Synthase (PAICS), P21 (RAC1) Activated Kinase 1 (PAK1), Transcription Factor AP-2 Alpha (TFAP2A), Cyclin Dependent Kinase Inhibitor 2C (CDKN2C), INSM Transcriptional Repressor 1 (INSM1), Stathmin 1 (STMN1), Activin A Receptor Type 1 (ACVR1), Calcium And Integrin Binding 1 (CIB1), LDL Receptor Related Protein 10 (LRP10), Chromogranin A (CHGA), Microtubule Associated Protein RP/EB Family Member 3 (MAPRE3), Synaptosome Associated Protein 91 (SNAP91), Capping Actin Protein, Gelsolin Like (CAPG), Galectin 3 (LGALS3), and Stratifin (SFN);
  b.) the non-redundant squamous cell carcinoma (SCC) genes of Table 1 under the subheading SCC subtype genes; or
  c.) proteasome (prosome, macropain) 26S subunit, non-ATPase, 14 (PSMD14), chromobox homolog 1 (HP1 beta homolog *Drosophila*) (CBX1), nuclear factor, interleukin 3 regulated (NFIL3), stearoyl-CoA desaturase 5 (SCD5), homeobox D1 (HOXD1), intercellular adhesion molecule 5, telencephalin (ICAM5), forkhead box H1 (FOXH1), calcium channel, voltage-dependent, beta 1 subunit (CACNB1), transcription factor 2, hepatic (TCF2); t-complex 1 (TCP1), flap structure-specific endonuclease 1 (FEN1), tubulin, alpha 1 (testis specific) (TUBA1), cytochrome b5 type B (outer mitochondrial membrane) (CYB5B); phosphoinositide-3-kinase, class 2, alpha polypeptide (PIK3C2A), anthrax toxin receptor 1 (ANTXR1), lipase, hormone-sensitive (LIPE), myosin binding protein H (MYBPH), docking protein 1, 62 kDa (downstream of tyrosine kinase 1) (DOK1), seven in absentia homolog 2 (*Drosophila*) (SIAH2), integrin, alpha 6 (ITGA6), islet cell autoantigen 1, 69 kDa (ICA1), thyroid transcription factor 1 (TITF1), hepsin (transmembrane protease, serine 1) (HPN), tripartite motif-containing 29 (TRIM29), desmocollin 3 (DSC3); bone morphogenetic protein 7 (osteogenic protein 1) (BMP7), mahogunin, ring finger 1 (MGRN1), hyaluronoglucosaminidase 2 (HYAL2), myosin VIIA (MYO7A), ATP-binding cassette, sub-family C (CFTR/MRP), member 5 (ABCC5), gap junction protein, beta 5 (connexin 31.1) (GJB5), pleckstrin homology domain containing, family A, member 6 (PLEKHA6), malic enzyme 3, NADP(+)-dependent, mitochondrial (ME3), and aldehyde dehydrogenase 3 family, member B1 (ALDH3B1).

2. The method of claim 1, wherein the lung tissue sample comprises lung cells embedded in paraffin.

3. The method of claim 1, wherein the lung tissue sample is a fresh frozen sample.

4. The method of claim 1, wherein the expression level of each classifier gene of the plurality of classifier genes is measured using an amplification or hybridization assay.

5. The method of claim 4, wherein the hybridization assay is a microarray assay.

6. The method of claim 4, wherein the amplification assay is quantitative RT-PCR (qRT-PCR).

7. The method of claim 1, wherein the group of classifier genes is Cadherin 5 (CDH5), C-Type Lectin Domain Family 3 Member B (CLEC3B), Platelet And Endothelial Cell Adhesion Molecule 1 (PECAM1), Phosphoribosylaminoimidazole Carboxylase And Phosphoribosylaminoimidazolesuccinocarboxamide Synthase (PAICS), P21 (RAC1) Activated Kinase 1 (PAK1), Transcription Factor AP-2 Alpha (TFAP2A), Cyclin Dependent Kinase Inhibitor 2C (CDKN2C), INSM Transcriptional Repressor 1 (INSM1), Stathmin 1 (STMN1), Activin A Receptor Type 1 (ACVR1), Calcium And Integrin Binding 1 (CIB1), LDL Receptor Related Protein 10 (LRP10), Chromogranin A (CHGA), Microtubule Associated Protein RP/EB Family Member 3 (MAPRE3), Synaptosome Associated Protein 91 (SNAP91), Capping Actin Protein, Gelsolin Like (CAPG), Galectin 3 (LGALS3), and Stratifin (SFN).

8. The method of claim 1, further comprising normalizing the expression level of every classifier from group (a), (b) or (c) to an average expression level of a plurality of housekeeping genes.

9. The method of claim 8, wherein the plurality of housekeeping genes are Cofilin 1 (CFL1), Eukaryotic Translation Elongation Factor 1 Alpha 1 (EEF1A1), Ribosomal Protein L10 (RPL10), Ribosomal Protein L28 (RPL28), and Ribosomal Protein L37a (RPL37A).

10. The method of claim 1, wherein the group of classifier genes are the non-redundant squamous cell carcinoma (SCC) genes of Table 1 under the subheading SCC subtype genes.

11. The method of claim 1, wherein the group of classifier genes are proteasome (prosome, macropain) 26S subunit, non-ATPase, 14 (PSMD14), chromobox homolog 1 (HP1 beta homolog *Drosophila*) (CBX1), nuclear factor, interleukin 3 regulated (NFIL3), stearoyl-CoA desaturase 5 (SCD5), homeobox D1 (HOXD1), intercellular adhesion molecule 5, telencephalin (ICAM5), forkhead box H1 (FOXH1), calcium channel, voltage-dependent, beta 1 subunit (CACNB1), transcription factor 2, hepatic (TCF2); t-complex 1 (TCP1), flap structure-specific endonuclease 1 (FEN1), tubulin, alpha 1 (testis specific) (TUBA1), cytochrome b5 type B (outer mitochondrial membrane) (CYB5B); phosphoinositide-3-kinase, class 2, alpha polypeptide (PIK3C2A), anthrax toxin receptor 1 (ANTXR1), lipase, hormone-sensitive (LIPE), myosin binding protein H (MYBPH), docking protein 1, 62 kDa (downstream of tyrosine kinase 1) (DOK1), seven in absentia homolog 2 (*Drosophila*) (SIAH2), integrin, alpha 6 (ITGA6), islet cell autoantigen 1, 69 kDa (ICA1), thyroid transcription factor 1 (TITF1), hepsin (transmembrane protease, serine 1) (HPN), tripartite motif-containing 29 (TRIM29), desmocollin 3 (DSC3); bone morphogenetic protein 7 (osteogenic protein 1) (BMP7), mahogunin, ring finger 1 (MGRN1), hyaluronoglucosaminidase 2 (HYAL2), myosin VILA (MYO7A), ATP-binding cassette, sub-family C (CFTR/MRP), member 5 (ABCC5), gap junction protein, beta 5 (connexin 31.1) (GJB5), pleckstrin homology domain containing, family A, member 6 (PLEKHA6), malic enzyme 3, NADP(+)-dependent, mitochondrial (ME3), and aldehyde dehydrogenase 3 family, member B1 (ALDH3B1).

12. The method of claim 1, further comprising measuring the expression of every classifier gene in group (a), (b) or (c) in a normal sample, a small cell lung cancer (SCLC) sample, a carcinoid sample, an adenocarcinoma sample or a squamous cell carcinoma sample.

\* \* \* \* \*